United States Patent
Nguyen et al.

(10) Patent No.: US 8,828,973 B2
(45) Date of Patent: *Sep. 9, 2014

(54) COMPOUNDS AS RECEPTOR MODULATORS WITH THERAPEUTIC UTILITY

(71) Applicant: Allergan, Inc., Irvine, CA (US)

(72) Inventors: Phong X. Nguyen, Placentia, CA (US); Todd M. Heidelbaugh, Fountain Valley, CA (US); John R. Cappiello, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/218,815

(22) Filed: Mar. 18, 2014

(65) Prior Publication Data

US 2014/0221317 A1     Aug. 7, 2014

Related U.S. Application Data

(63) Continuation of application No. 13/764,407, filed on Feb. 11, 2013, now Pat. No. 8,741,875, which is a continuation-in-part of application No. 12/951,504, filed on Nov. 22, 2010, now Pat. No. 8,440,644.

(60) Provisional application No. 61/264,038, filed on Nov. 24, 2009.

(51) Int. Cl.
| | | |
|---|---|---|
| *A61K 31/675* | (2006.01) | |
| *A61K 31/662* | (2006.01) | |
| *C07F 9/38* | (2006.01) | |
| *A61P 27/02* | (2006.01) | |
| *A61P 3/10* | (2006.01) | |
| *A61P 29/00* | (2006.01) | |
| *A61P 11/00* | (2006.01) | |
| *A61P 1/00* | (2006.01) | |
| *A61P 37/00* | (2006.01) | |
| *A61P 9/00* | (2006.01) | |
| *A61P 17/02* | (2006.01) | |
| *A61P 25/00* | (2006.01) | |
| *C07F 9/6553* | (2006.01) | |
| *C07F 9/6539* | (2006.01) | |
| *C07D 333/22* | (2006.01) | |
| *C07F 9/09* | (2006.01) | |
| *C07D 405/04* | (2006.01) | |
| *C07D 333/20* | (2006.01) | |
| *C07F 9/653* | (2006.01) | |
| *C07F 9/655* | (2006.01) | |
| *C07F 9/6503* | (2006.01) | |

(52) U.S. Cl.
CPC ......... *C07F 9/655345* (2013.01); *C07F 9/6539* (2013.01); *C07D 333/22* (2013.01); *C07F 9/09* (2013.01); *C07D 405/04* (2013.01); *C07D 333/20* (2013.01); *C07F 9/653* (2013.01); *C07F 9/65515* (2013.01); *C07F 9/65037* (2013.01)
USPC .................. 514/89; 514/92; 514/114; 546/22; 548/112; 562/11

(58) Field of Classification Search
None
See application file for complete search history.

(56) References Cited

U.S. PATENT DOCUMENTS

| | | | |
|---|---|---|---|
| 4,952,683 | A | 8/1990 | Tschannen et al. |
| 5,102,901 | A | 4/1992 | van Wijngaarden et al. |

(Continued)

FOREIGN PATENT DOCUMENTS

| | | |
|---|---|---|
| WO | 03-061567 | 7/2003 |
| WO | 03-062248 | 7/2003 |

(Continued)

OTHER PUBLICATIONS

Vippagunta et al. "Crystalline Solids," Advanced Drug Delivery Reviews, 2001, 48, pp. 18.*

(Continued)

*Primary Examiner* — Ernst V Arnold
*Assistant Examiner* — Jianfeng Song
(74) *Attorney, Agent, or Firm* — Doina G. Ene

(57) ABSTRACT

The present invention relates to novel amine derivatives, processes for preparing them, pharmaceutical compositions containing them and their use as pharmaceuticals as modulators of sphingosine-1-phosphate receptors.

12 Claims, 1 Drawing Sheet

Lymphopenia induced by S1P1 agonists in mice: Time course (10 mg/Kg)
[3-({4-[(5-phenylpentyl)oxy]-3-(2-thienyl)benzyl}amino)propyl]phosphonic acid

(56) References Cited

U.S. PATENT DOCUMENTS

| | | | |
|---|---|---|---|
| 5,110,987 A | 5/1992 | Liotta et al. | |
| 5,294,722 A | 3/1994 | Kim | |
| 5,403,851 A | 4/1995 | D'Orlando et al. | |
| 5,580,878 A | 12/1996 | D'Orlando et al. | |
| 6,235,912 B1 | 5/2001 | Takesako et al. | |
| 6,239,297 B1 | 5/2001 | Takesako et al. | |
| 2003/0125371 A1 | 7/2003 | Elokdah et al. | |
| 2009/0074789 A1* | 3/2009 | Sabbadini et al. | 424/155.1 |
| 2009/0312315 A1 | 12/2009 | Yamaguchi | |

FOREIGN PATENT DOCUMENTS

| | | | |
|---|---|---|---|
| WO | WO 03/061567 | | 7/2003 |
| WO | WO03/061567 | | 7/2003 |
| WO | WO03/062248 | | 7/2003 |
| WO | WO 03/062248 | * | 7/2003 |
| WO | WO-03-062248 | * | 7/2003 |
| WO | 2008-030838 | | 3/2008 |
| WO | 2008-030843 | | 3/2008 |
| WO | WO2008/030838 | | 3/2008 |
| WO | WO 2008/030838 | | 3/2008 |
| WO | WO2008/030843 | | 3/2008 |
| WO | WO 2008/030843 | | 3/2008 |

OTHER PUBLICATIONS

Müller, Inorganic Chemistry, p. 14-15, 1993.*

Saag KG, Shane E, Boonen S, et al. (Nov. 2007). "Teriparatide or alendronate in glucocorticoid-induced osteoporosis". The New England Journal of Medicine 357 (20): 2028-39, whole document.*

Muller, Inorganic Chemistry, pp. 14-15, 1993.

Saag, Kenneth, G., et al., "Teriparatide or alendronate in glucocoticoid-induced osteoporosis," (Nov. 2007) N Eng J Med; 357 (20): 2028-39, whole document.

Vippagunta, et al., "Crystalline Solids," Advanced Drug Delivery Review, 2001, 48, p. 18.

Cross, L.C. et al, Rules for the Nomenclature of Organic Chemistry, Section E: Stereochemistry, Pure & Appl. Chem., 1976, 11-30, 45.

Dosa, Peter et al, Solubilized Phenyl-Pyrazole Ureas as Potent, Selective 5-HT2A Inveerse-Agonists and Their Application as Antiplatelet Agents, Bioorganic & Medicinal Chemistry, 2009, 5486-5489, 19.

Jeffrey J. Hale, et al., A Rational Utilization of High-Throughput Screening Affords Selective, Orally Bioavailable 1-Benzyl-3-Carboxyazetidine, Journal of Medicine Chemistry, Jan. 1, 2004, 6662-6665, 45 (27), US.

Stahl, Heinrich et al., Handbook of Pharmaceutical Salts, Vertag Helvetica Chimica Acta—Zurich, 2002, 329-345.

Xiong, Yifeng et al, Discovery and Structure-Activity Relationship of 3-Methoxy-N-(3-(1-methyl-1H-pyrazol-5-yl)-4-(2-morpholinoethoxy)phenyl)benzamide (APD791): A Highly Selective 5-Hydroxotryptamine2A Receptor Inverse Agonist for the Treatment of Arterial Thrombosis, J. Med. Chem., 2010, 4412-4421, 53.

Patent Cooperation Treaty, Notification of Trasmittal of the International Search Report and the Written Opinion of the International Searching Authority, or the Declaration, Form PCT/ISA/220, Int. App. No. PCT/US2010/057361, Apr. 14, 2011.

Patent Coopration Treaty, Notification of Transmittal of the International Search Report and the Written Opinion of the International Searchin Authority, or the Declaration, Form PCT/ISA/220, Int. App. No. PCT/US2010/057336, Apr. 14, 2011.

Cross, L.C., et al., "Rules for the Nonmenclature of Organic Chemistry," Section E: Stereochemistry, Pure & Appl. Chem., 1976, 45, pp. 11-30.

Dosa, Peter; "Solubilized Phenyl-pyrazole ureas as potent, selective 5-HT2A inverse-agonists and their application as antiplatelet agents"; Bioorganic & Medicinal Chemistry Letters 19 (2009) 5486-5489.

Hale, Jeffrey J., et al., "A Rational Utilization of High-Throughput Screening Affords Selective, ORally Bioavailable 1-Benzyl-3-carboxyazetidine Sphingosine-1- phosphate -1 Receptor Agonists," Journal of Medicinal Chemistry, American Chemical Society, vol. 47, No. 27, Jan. 1, 2004.

Saag, Jenneth G., et al., "Teriparatide or alendronate in glucocorticoid-induced osteoporosis," (Nov. 2007) N Eng H Med; 357 (20): 2028-39, whole document.

Stahl, P. Heinrich, et al., Handbook of Pharmaceutical Salts, Verlag Helvetica Chemica Acta-Zurich, 2002, pp. 329-345.

Vippagunta, et al., "Crystalline Solids," Advanced Drug Delivery Reviews, 2001, 48, pp. 18.

Xiong, Yifeng; et al., "Discovery and Structure-activity Relationship of 3-Methoxy-N-(3-(1-methyl-1H-pyrazol-5-yl)-4-(2-morpholinoethoxy)phenyl)benzamide (APD791): A Highly Selctive 5-Hydroxytryptamine2A Receptor Inverse Agonist for the Treatment of Arterial Thrombosis"; Journal of Medicial Chemistry 2010, 53, 4412-4421.

International Search Report for PCT/US2010/057336, Apr. 14, 2011.
International Search Report for PCT/US2010/507361, Apr. 14, 2011.

Hale Jeffrey J et al: "A Rational Utilization of High-Throughout Screening Affords Selective, ORally Bioavailable 1-Benzyl-3-carboxyazetidine Sphingosine-1- phosphate -1 Receptor Agonists", Journal of Medicinal Chemistry, American Chemical Society; vol. 47, No. 27, Jan. 1, 2004.

Yifeng Xiong; "Discovery and Structure-Activity Relationship of 3-Methoxy-N-(3-(1-methyl-1H-pyrazol-5-yl)-4-(2morpholinoethoxy)phenyl)benzamide (APD791): A Highly Selective 5-Hydroxytryptamine2A Receptor Inverse Agonist for the Treatment of Arterial Thrombosis"; Journal of Medicinal Chemistry 2010, 53, 4412-4421.

Peter Dosa; "Solubilized phenyl-pyrazole ureas as potent, selective 5-HT2A inverse-agonists and their application as antiplatelet agents"; Bioorganic & Medicinal Chemistry Letters 19 (2009) 5486-5489.

* cited by examiner

Lymphopenia induced by S1P1 agonists in mice: Time course (10 mg/Kg)
[3-({4-[(5-phenylpentyl)oxy]-3-(2-thienyl)benzyl}amino)propyl]phosphonic acid
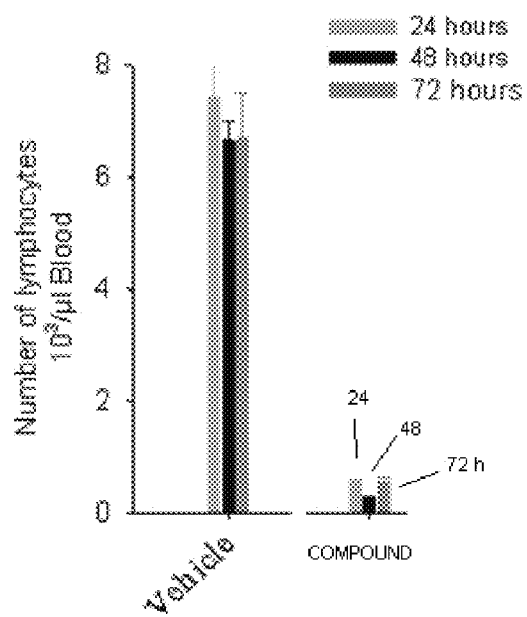

COMPOUNDS AS RECEPTOR MODULATORS WITH THERAPEUTIC UTILITY

CROSS REFERENCE TO RELATED APPLICATIONS

This application is a continuation of U.S. patent application Ser. No. 13/764,407, filed Feb. 11, 2013, which is a continuation-in-part of U.S. patent application Ser. No. 12/951,504, filed Nov. 22, 2010, which claims the benefit of U.S. Provisional Application Ser. No. 61/264,038, filed Nov. 24, 2009, which are hereby incorporated by reference in their entirety.

FIELD OF THE INVENTION

The present invention relates to novel amine derivatives, processes for preparing them, pharmaceutical compositions containing them and their use as pharmaceuticals as modulators of sphingosine-1-phosphate receptors. The invention relates specifically to the use of these compounds and their pharmaceutical compositions to treat disorders associated with sphingosine-1-phosphate (S1P) receptor modulation.

BACKGROUND OF THE INVENTION

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular diseases. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

Journal of Medicinal Chemistry 2010, 53, 4412-4421 and Bioorganic & Medicinal Chemistry Letters 19 (2009) 5486-5489, describe phenyl-pyrazole derivatives as 5-HT$_{2A}$ receptor antagoinists.

Patent Application US2009312315 describes phenyl-substituted carboxylic acid derivatives as PAI-1 inhibitors.

SUMMARY OF THE INVENTION

We have now discovered a group of novel compounds which are potent and selective sphingosine-1-phosphate modulators. As such, the compounds described herein are useful in treating a wide variety of disorders associated with modulation of sphingosine-1-phosphate receptors. The term "modulator" as used herein, includes but is not limited to: receptor agonist, antagonist, inverse agonist, inverse antagonist, partial agonist, partial antagonist.

This invention describes compounds of Formula I, which have sphingosine-1-phosphate receptor biological activity. The compounds in accordance with the present invention are thus of use in medicine, for example in the treatment of humans with diseases and conditions that are alleviated by S1P modulation.

In one aspect the invention provides a compound represented by Formula I or a pharmaceutically acceptable salt thereof or stereoisomeric forms thereof, or the geometrical isomers, enantiomers, diastereoisomers, tautomers, zwitterions and pharmaceutically acceptable salts thereof:

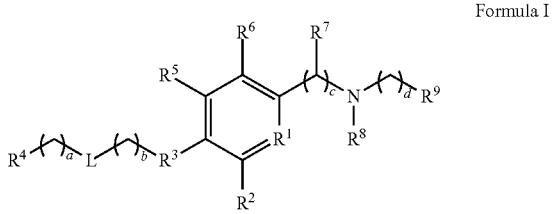

Formula I wherein:
$R^1$ is N or C—$R^{10}$;
$R^2$ is optionally substituted aromatic heterocycle, optionally substituted non-aromatic heterocycle, optionally substituted cycloalkyl, optionally substituted cycloalkenyl or optionally substituted aryl;
$R^3$ is O, N—$R^{11}$, CH—$R^{12}$ or S, —$CR^{13}$=$CR^{14}$—, —C(O) or —C≡O—;
$R^4$ is H, optionally substituted aromatic heterocycle, optionally substituted non-aromatic heterocycle, optionally substituted cycloalkyl, optionally substituted cycloalkenyl or optionally substituted aryl;
$R^5$ is H, halogen, hydroxyl, —$OC_{1-3}$ alkyl, or optionally substituted $C_{1-3}$ alkyl;
$R^6$ is H, optionally substituted $C_{1-3}$ alkyl, halogen, hydroxyl or —$OC_{1-3}$ alkyl;
$R^7$ is H or optionally substituted $C_{1-6}$ alkyl;
$R^8$ is H or optionally substituted $C_{1-6}$ alkyl;
$R^9$ is —$OPO_3H_2$, —COOH, —$P(O)(OH)_2$, optionally substituted $C_{3-6}$ alkyl, —$S(O)_2OH$, —P(O)MeOH, —P(O)(H)OH or —$OR^{15}$;
$R^{10}$ is H, optionally substituted $C_{1-6}$ alkyl, halogen, hydroxyl or —$OC_{1-3}$ alkyl;
$R^{11}$ is H or optionally substituted $C_{1-3}$ alkyl;
$R^{12}$ is H, optionally substituted $C_{1-3}$ alkyl, halogen, hydroxyl, —$OC_{1-3}$alkyl or amino;
$R^{13}$ is H or optionally substituted $C_{1-3}$ alkyl;
$R^{14}$ is H or optionally substituted $C_{1-3}$ alkyl;
$R^{15}$ is H or optionally substituted $C_{1-3}$ alkyl;
L is $CHR^{16}$, O, S, $NR^{17}$ or —C(O)—;
a is 0, 1, 2, 3, 4 or 5;
b is 0, 1, 2, 3, 4 or 5;
c is 0 or 1;
d is 0, 1, 2 or 3;
$R^{16}$ is H, optionally substituted $C_{1-3}$ alkyl, —$OC_{1-3}$ alkyl, halogen, hydroxyl or amino, and
$R^{17}$ is H or optionally substituted $C_{1-3}$ alkyl;
with the provisos:
a). when $R^3$ is O, N—$R^{11}$, or S, and b is 0 or 1 then L is not O, S, or $NR^{17}$; and
b). when $R^9$ is —$OPO_3H_2$, —COOH, —$P(O)(OH)_2$, —$S(O)_2OH$, —P(O)MeOH or —P(O)(H)OH then d is not 0; and c). when $R^9$ is $OR^{15}$ then d is not 0 or 1; and
d). except compound

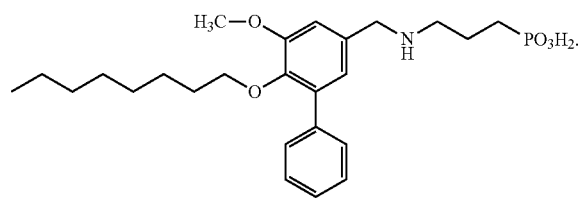

The term "alkyl", as used herein, refers to saturated, monovalent or divalent hydrocarbon moieties having linear or branched moieties or combinations thereof and containing 1-6 carbon atom. One methylene (—$CH_2$—) group, of the alkyl can be replaced by oxygen, sulfur, sulfoxide, nitrogen, carbonyl, carboxyl, sulfonyl, or by a divalent $C_{3-6}$ cycloalkyl. Alkyl groups can be substituted by halogen, hydroxyl, cycloalkyl, amino, non-aromatic heterocycles, carboxylic acid, phosphonic acid groups, sulphonic acid groups, phosphoric acid, nitro groups, amide groups, sulfonamide groups, amino groups.

The term "cycloalkyl", as used herein, refers to a monovalent or divalent group of 3 to 8 carbon atoms, preferably 3 to 5 carbon atoms derived from a saturated cyclic hydrocarbon. Cycloalkyl groups can be monocyclic or polycyclic. Cycloalkyl can be substituted by 1 to 3 $C_{1-3}$ alkyl groups or 1 or 2 halogens. Cycloalkyl group in the present case is cyclopentane.

The term "cycloalkenyl", as used herein, refers to a monovalent or divalent group of 3 to 8 carbon atoms, preferably 3 to 6 carbon atoms derived from a saturated cycloalkyl having one double bond. Cycloalkenyl groups can be monocyclic or polycyclic.

Cycloalkenyl groups can be substituted by 1 to 3 $C_{1-3}$ alkyl groups or 1 or 2 halogens. Cycloalkenyl group in the present case is cyclopentene.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. $C_{2-6}$ alkenyl can be in the E or Z configuration. Alkenyl groups can be substituted by 1 to 2 $C_{1-3}$ alkyl.

The term "alkynyl", as used herein, refers to a monovalent or divalent hydrocarbon radical having 2 to 6 carbon atoms, derived from a saturated alkyl, having at least one triple bond.

The term "heterocycle" as used herein, refers to a 3 to 10 membered ring, which can be aromatic or non-aromatic, saturated or non-saturated, containing at least one heteroatom selected form O or N or S or combinations of at least two thereof, interrupting the carbocyclic ring structure. The heterocyclic ring can be saturated or non-saturated. The heterocyclic ring can be interrupted by a C=O; the S heteroatom can be oxidized. Heterocycles can be monocyclic or polycyclic. Heterocyclic ring moieties can be substituted by halogen atoms, sulfonyl groups, sulfoxide groups, nitro groups, cyano groups, —$OC_{1-6}$ alkyl groups, —$SC_{1-6}$ alkyl groups, —$C_{1-8}$ alkyl groups, —$C_{2-6}$ alkenyl groups, —$C_{2-6}$ alkynyl groups, ketone groups, alkylamino groups, amino groups, aryl groups, $C_{3-8}$ cycloalkyl groups or hydroxyl groups. Usually heterocyclic groups are 5 or 6 membered rings. Usually in the present case heterocyclic groups are pyridine, pyrazol, pyrazolidine, pyrroline, pyrrolidine, imidazoline, pyrazoline, thiazoline, oxazoline, thiophene, dihydrothiophene, furan, dihydrofuran, pyrrole, pyrroline, oxazole, thiazole, imidazole, pyrazole, pyrazoline, isoxazole, isothiazole, tetrazole, oxadiazole, 1,2,5-oxadiazole, thiadiazole, 1,2,3-triazole, 1,2,4-triazole, imidazole, imidazoline, imidazolidine, pyrrolidinone, pyrrol-2(3H)-one, imidazolidin-2-one, or 1,2,4-triazol-5(4H)-one.

The term "aryl" as used herein, refers to an organic moiety derived from an aromatic hydrocarbon consisting of a ring containing 6 to 10 carbon atoms, by removal of one hydrogen atom. Aryl can be substituted by halogen atoms, sulfonyl $C_{1-6}$ alkyl groups, sulfoxide $C_{1-6}$ alkyl groups, sulfonamide groups, carboxcyclic acid groups, $C_{1-6}$ alkyl carboxylates (ester) groups, amide groups, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, aldehydes, alkylamino groups, amino groups, aryl groups, $C_{3-8}$ cycloalkyl groups or hydroxyl groups. Aryls can be monocyclic or polycyclic.

Usually aryl is phenyl.

The group of formula "—$CR^{13}$=$CR^{14}$—", as used herein, represents an alkenyl radical.

The group of formula "—C≡C—", as used herein, represents an alkynyl radical.

The term "hydroxyl" as used herein, represents a group of formula "—OH".

The term "carbonyl" as used herein, represents a group of formula "—C=O".

The term "carboxyl" as used herein, represents a group of formula "—C(O)O—".

The term "sulfonyl" as used herein, represents a group of formula "—$SO_2$".

The term "sulfate" as used herein, represents a group of formula "—O—S(O)$_2$—O—".

The term "carboxylic acid" as used herein, represents a group of formula "—C(O)OH".

The term "sulfoxide" as used herein, represents a group of formula "—S=O".

The term "phosphonic acid" as used herein, represents a group of formula "—P(O)(OH)$_2$".

The term "phosphoric acid" as used herein, represents a group of formula "—(O)P(O)(OH)$_2$".

The term "boronic acid", as used herein, represents a group of formula "—B(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

The term "ketone" as used herein, represents an organic compound having a carbonyl group linked to a carbon atom such as —(CO)$R^x$ wherein $R^x$ can be alkyl, aryl, cycloalkyl, cycloalkenyl, heterocycle as defined above.

The term "amine" as used herein, represents a group of formula "—$NR^xR^y$", wherein $R^x$ and $R^y$ can be the same or independently H, alkyl, aryl, cycloalkyl, cycloalkenyl, heterocycle as defined above.

The term "nitro" as used herein, represents a group of formula "—$NO_2$".

The term "cyano" as used herein, represents a group of formula "—CN".

The term "amide" as used herein, represents a group of formula "—C(O)$NR^xR^y$," wherein $R^x$ and $R^y$ can be the same or independently H, alkyl, aryl, cycloalkyl, cycloalkenyl, heterocycle as defined above.

The term "sulfonamide" as used herein, represents a group of formula "—S(O)$_2$NR$^x$R$^y$" wherein R$^x$ and R$^y$ can be the same or independently H, alkyl, aryl, cycloalkyl, cycloalkenyl, heterocycle as defined above.

Generally R$^1$ is N or C—R$^{10}$.

Generally R$^2$ is optionally substituted aromatic heterocycle, optionally substituted non-aromatic heterocycle, optionally substituted cycloalkyl, optionally substituted cycloalkenyl or optionally substituted aryl. Usually, in the present case, R$^2$ is aromatic heterocycle or cycloalkenyl. Usually aromatic heterocyclic rings are 5 membered rings. Preferred R$^2$ are pyrazole, pyrazolidine, pyrroline, pyrrolidine, imidazoline, pyrazoline, thiazoline, oxazoline, thiophene, dihydrothiophene, furan, dihydrofuran, pyrrole, pyrroline, oxazole, thiazole, imidazole, pyrazole, pyrazoline, isoxazole, isothiazole, tetrazole, oxadiazole, 1,2,5-oxadiazole, thiadiazole, 1,2,3-triazole, 1,2,4-triazole, imidazole, imidazoline, pyrrolidinone, pyrrol-2(3H)-one, imidazolidin-2-one, or 1,2,4-triazol-5(4H)-one.

Generally R$^3$ is O, N—R$^{11}$, CH—R$^{12}$, S, —CR$^{13}$=CR$^{14}$—, —C(O) or —C≡C—. Usually, in the present case, R$^3$ is O, CH—R$^{12}$ or N—R$^{11}$.

Generally R$^4$ is H, optionally substituted aromatic heterocycle, optionally substituted non-aromatic heterocycle, optionally substituted cycloalkyl or optionally substituted aryl. Usually, in the present case, R$^4$ is optionally substituted aryl or H.

Generally R$^5$ is H, halogen, —OC$_{1-3}$ alkyl, hydroxyl or optionally substituted C$_{1-3}$ alky. Usually, in the present case, R$^5$ is H.

Generally R$^6$ is H, optionally substituted C$_{1-3}$ alkyl, halogen, hydroxyl or —OC$_{1-3}$ alkyl. Usually, in the present case, R$^6$ is H or halogen.

Generally R$^7$ is H or optionally substituted C$_{1-6}$ alkyl.

Generally R$^8$ is H or optionally substituted C$_{1-6}$ alkyl. Usually, in the present case, R$^8$ is H.

Generally R$^9$ is OPO$_3$H$_2$, COOH, P(O)(OH)$_2$, optionally substituted C$_{3-6}$ alkyl, —S(O)$_2$OH, —P(O)MeOH, —P(O)(H)OH or —OR$^{15}$. Usually, in the present case, R$^9$ is P(O)(OH)$_2$, or —S(O)$_2$OH or —P(O)MeOH.

Generally R$^{10}$ is H, optionally substituted C$_{1-6}$ alkyl, halogen, hydroxyl or —OC$_{1-3}$ alkyl. Usually, in the present case, R$^{10}$ is H.

Generally R$^{11}$ is H or optionally substituted C$_{1-3}$ alkyl.
Generally R$^{12}$ is H or optionally substituted C$_{1-3}$ alkyl
Generally R$^{13}$ is H or optionally substituted C$_{1-3}$ alkyl.
Generally R$^{14}$ is H or optionally substituted C$_{1-3}$ alkyl.
Generally R$^{15}$ is H or optionally substituted C$_{1-3}$ alkyl.

Generally a is 0, 1, 2, 3, 4 or 5. Usually, in the present case, a is 1, 2, 3, 4 or 5.

Generally b is 0, 1, 2, 3, 4 or 5. Usually, in the present case, b is 1, 2, 3 or 4.

Generally c is 0 or 1. Usually, in the present case, c is 1.

Generally d is 0, 1, 2 or 3. Usually, in the present case, d is 3.

Generally L is CHR$^{17}$, O, S or NR$^{17}$. Usually, in the present case, L is CHR$^{16}$.

Generally R$^{16}$ is H, optionally substituted C$_{1-3}$ alkyl, —OC$_{1-3}$ alkyl, halogen, hydroxyl, amino. Usually, in the present case, R$^{16}$ is H.

Generally R$^{17}$ is H or optionally substituted C$_{1-3}$ alkyl.

In one embodiment of the invention
R$^1$ is N or C—R$^{10}$;
R$^2$ is optionally substituted aromatic heterocycle or optionally substituted cycloalkenyl;
R$^3$ is O, N—R$^{11}$, CH—R$^{12}$ or S, —CR$^{13}$=CR$^{14}$—, —C(O) or —C≡C—;
R$^4$ is H, optionally substituted aromatic heterocycle, optionally substituted non-aromatic heterocycle, optionally substituted cycloalkyl, optionally substituted cycloalkenyl or optionally substituted aryl;
R$^5$ is H, halogen, hydroxyl, —OC$_{1-3}$ alkyl, or optionally substituted C$_{1-3}$ alkyl;
R$^6$ is H, optionally substituted C$_{1-3}$ alkyl, halogen, hydroxyl or —OC$_{1-3}$ alkyl;
R$^7$ is H or optionally substituted C$_{1-6}$ alkyl;
R$^8$ is H or optionally substituted C$_{1-6}$ alkyl;
R$^9$ is —OPO$_3$H$_2$, —COOH, —P(O)(OH)$_2$, optionally substituted C$_{3-6}$ alkyl, —S(O)$_2$OH, —P(O)MeOH, —P(O)(H)OH or —OR$^{15}$;
R$^{10}$ is H, optionally substituted C$_{1-6}$ alkyl, halogen, hydroxyl or —OC$_{1-3}$ alkyl;
R$^{11}$ is H or optionally substituted C$_{1-3}$ alkyl;
R$^{12}$ is H, optionally substituted C$_{1-3}$ alkyl, halogen, hydroxyl, —OC$_{1-3}$alkyl or amino;
R$^{13}$ is H or optionally substituted C$_{1-3}$ alkyl;
R$^{14}$ is H or optionally substituted C$_{1-3}$ alkyl;
R$^{15}$ is H or optionally substituted C$_{1-3}$ alkyl;
L is CHR$^{16}$, O, S, NR$^{17}$ or —C(O)—;
a is 0, 1, 2, 3, 4 or 5;
b is 0, 1, 2, 3, 4 or 5;
c is 0 or 1;
d is 0, 1, 2 or 3;
R$^{16}$ is H, optionally substituted C$_{1-3}$ alkyl, —OC$_{1-3}$ alkyl, halogen, hydroxyl or amino; and
R$^{17}$ is H or optionally substituted C$_{1-3}$ alkyl;
with the provisos
when R$^3$ is O, N—R$^{11}$, or S, and b is 0 or 1 then L is not O, S, or NR$^{17}$; and
when R$^9$ is —OPO$_3$H$_2$, —COOH, —P(O)(OH)$_2$, —S(O)$_2$OH, —P(O)MeOH or —P(O)(H)OH then d is not 0; and
when R$^9$ is —OR$^{15}$ then d is not 0 or 1.

In another embodiment of the invention
R$^1$ is N or C—R$^{10}$;
R$^2$ is optionally substituted 5-member aromatic heterocycle or optionally substituted cycloalkenyl;
R$^3$ is O, N—R$^{11}$, CH—R$^{12}$ or S, —CR$^{13}$=CR$^{14}$—, —C(O) or —C≡C—;
R$^4$ is H, optionally substituted aromatic heterocycle, optionally substituted non-aromatic heterocycle, optionally substituted cycloalkyl, optionally substituted cycloalkenyl or optionally substituted aryl;
R$^5$ is H, halogen, hydroxyl, —OC$_{1-3}$ alkyl, or optionally substituted C$_{-3}$ alkyl;
R$^6$ is H, C$_{1-3}$ alkyl, halogen, hydroxyl or —OC$_{1-3}$ alkyl;
R$^7$ is H or C$_{1-6}$ alkyl;
R$^8$ is H or C$_{1-6}$ alkyl;
R$^9$ is —OPO$_3$H$_2$, —COOH, —P(O)(OH)$_2$, optionally substituted C$_{3-6}$ alkyl, —S(O)$_2$OH, —P(O)MeOH, —P(O)(H)OH or —OR$^{15}$;
R$^{10}$ is H, optionally substituted C$_{1-6}$ alkyl, halogen, hydroxyl or —OC$_{1-3}$ alkyl;
R$^{11}$ is H or optionally substituted C$_{1-3}$ alkyl;
R$^{12}$ is H, optionally substituted C$_{1-3}$ alkyl, halogen, hydroxyl, —OC$_{1-3}$alkyl or amino;
R$^{13}$ is H or optionally substituted C$_{1-3}$ alkyl;
R$^{14}$ is H or optionally substituted C$_{1-3}$ alkyl;
R$^{15}$ is H or optionally substituted C$_{1-3}$ alkyl;
L is CHR$^{18}$, O, S, NR$^{17}$ or —C(O)—;
a is 0, 1, 2, 3, 4 or 5;
b is 0, 1, 2, 3, 4 or 5;
c is 0 or 1;
d is 0, 1, 2 or 3;

$R^{16}$ is H, optionally substituted $C_{1-3}$ alkyl, —$OC_{1-3}$ alkyl, halogen, hydroxyl or amino, and
$R^{17}$ is H or optionally substituted $C_{1-3}$ alkyl;
with the provisos:
when $R^3$ is O, N—$R^{11}$, or S, and b is 0 or 1 then L is not O, S, or $NR^{17}$; and
when $R^9$ is —$OPO_3H_2$, —COOH, —$P(O)(OH)_2$, —$S(O)_2OH$, —P(O)MeOH or —P(O)(H)OH then d is not 0; and
when $R^9$ is —$OR^{15}$ then d is not 0 or 1.

In another embodiment of the invention
$R^1$ is N or C—$R^{10}$;
$R^2$ is cyclopentane, cyclopentene, pyrazolidine, pyrroline, pyrrolidine, imidazoline, pyrazoline, thiazoline, oxazoline, thiophene, dihydrothiophene, furan, dihydrofuran, pyrrole, pyrroline, pyrrolidine, oxazole, oxazoline, thiazole, imidazole, pyrazole, pyrazoline, isoxazole, isothiazole, tetrazole, oxadiazole, 1,2,5-oxadiazole, thiadiazole, 1,2,3-triazole, 1,2,4-triazole, imidazole, imidazoline, pyrrolidinone, pyrrol-2(3H)-one, imidazolidin-2-one, or 1,2,4-triazol-5(4H)-one;
$R^3$ is O, N—$R^{11}$, CH—$R^{12}$ or S, —$CR^{13}$=$CR^{14}$—, —C(O) or —C≡C—;
$R^4$ is H, optionally substituted aromatic heterocycle, optionally substituted non-aromatic heterocycle, optionally substituted cycloalkyl, optionally substituted cycloalkenyl or optionally substituted aryl;
$R^5$ is H, halogen, hydroxyl, —$OC_{1-3}$ alkyl, or optionally substituted $C_{1-3}$ alkyl;
$R^6$ is H, optionally substituted $C_{1-3}$ alkyl, halogen, hydroxyl or —$OC_{1-3}$ alkyl;
$R^7$ is H or optionally substituted $C_{1-6}$ alkyl;
$R^8$ is H or optionally substituted $C_{1-6}$ alkyl;
$R^9$ is —$OPO_3H_2$, —COOH, —$P(O)(OH)_2$, —$C_{3-6}$ alkyl, —$S(O)_2OH$, —P(O)MeOH, —P(O)(H)OH or —$OR^{15}$;
$R^{10}$ is H, optionally substituted $C_{1-6}$ alkyl, halogen, hydroxyl or —$OC_{1-3}$ alkyl;
$R^{11}$ is H or optionally substituted $C_{1-3}$ alkyl;
$R^{12}$ is H, optionally substituted $C_{1-3}$ alkyl, halogen, hydroxyl, —$OC_{1-3}$alkyl or amino;
$R^{13}$ is H or optionally substituted $C_{1-3}$ alkyl;
$R^{14}$ is H or optionally substituted $C_{1-3}$ alkyl;
$R^{15}$ is H or optionally substituted $C_{1-3}$ alkyl;
L is $CHR^{16}$, O, S, $NR^{17}$ or —C(O)—;
a is 0, 1, 2, 3, 4 or 5;
b is 0, 1, 2, 3, 4 or 5;
c is 0 or 1;
d is 0, 1, 2 or 3;
$R^{16}$ is H, $C_{1-3}$ alkyl, —$OC_{1-3}$ alkyl, halogen, hydroxyl or amino, and
$R^{17}$ is H or $C_{1-3}$ alkyl;
with the provisos:
when $R^3$ is O, N—$R^{11}$, or S, and b is 0 or 1 then L is not O, S, or $NR^{17}$; and
when $R^9$ is —$OPO_3H_2$, —COOH, —$P(O)(OH)_2$, —$S(O)_2OH$, —P(O)MeOH or —P(O)(H)OH then d is not 0; and
when $R^9$ is —$OR^{15}$ then d is not 0 or 1.

In another embodiment of the invention
$R^1$ is N or C—$R^{10}$;
$R^2$ is optionally substituted 5-member aromatic heterocycle or cycloalkenyl;
$R^3$ is O, N—$R^{11}$, CH—$R^{12}$ or S, —$CR^{13}$=$CR^{14}$—, —C(O) or —C≡C—;
$R^4$ is H, aromatic heterocycle, non-aromatic heterocycle, cycloalkyl, cycloalkenyl or optionally substituted aryl;
$R^5$ is H, halogen, hydroxyl, —$OC_{1-3}$ alkyl, or $C_{1-3}$ alkyl;
$R^6$ is H, $C_{1-3}$ alkyl, halogen, hydroxyl or —$OC_{1-3}$ alkyl;
$R^7$ is H or $C_{1-6}$ alkyl;
$R^8$ is H or $C_{1-6}$ alkyl;
$R^9$ is —$OPO_3H_2$, or —$OR^{15}$;
$R^{10}$ is H, $C_{1-6}$ alkyl, halogen, hydroxyl or —$OC_{1-3}$ alkyl;
$R^{11}$ is H or $C_{1-3}$ alkyl;
$R^{12}$ is H, $C_{1-3}$ alkyl, halogen, hydroxyl, —$OC_{1-3}$alkyl or amino;
$R^{13}$ is H or $C_{1-3}$ alkyl;
$R^{14}$ is H or $C_{1-3}$ alkyl;
$R^{15}$ is H or $C_{1-3}$ alkyl;
L is $CHR^{16}$, O, S, $NR^{17}$ or —C(O)—;
a is 0, 1, 2, 3, 4 or 5;
b is 0, 1, 2, 3, 4 or 5;
c is 0 or 1;
d is 1, 2 or 3;
$R^{16}$ is H, $C_{1-3}$ alkyl, —$OC_{1-3}$ alkyl, halogen, hydroxyl or amino, and
$R^{17}$ is H or $C_{1-3}$ alkyl;
with the provisos:
when $R^3$ is O, N—$R^{11}$, or S, and b is 0 or 1 then L is not O, S, or $NR^{17}$; and
when $R^9$ is —$OR^{15}$ then d is not 1.

In another embodiment of the invention
$R^1$ is N or C—$R^{10}$;
$R^2$ is optionally substituted 5-member aromatic heterocycle or cycloalkenyl;
$R^3$ is O, N—$R^{11}$, CH—$R^{12}$ or S, —$CR^{13}$=$CR^{14}$—, —C(O) or —C≡C—;
$R^4$ is H, aromatic heterocycle, non-aromatic heterocycle, cycloalkyl, cycloalkenyl or optionally substituted aryl;
$R^5$ is H, halogen, hydroxyl, —$OC_{1-3}$ alkyl, or $C_{1-3}$ alkyl;
$R^6$ is H, $C_{1-3}$ alkyl, halogen, hydroxyl or —$OC_{1-3}$ alkyl;
$R^7$ is H or $C_{1-6}$ alkyl;
$R^8$ is H or $C_{1-6}$ alkyl;
$R^9$ is —$P(O)(OH)_2$, —P(O)MeOH, or —P(O)(H)OH;
$R^{10}$ is H, $C_{1-6}$ alkyl, halogen, hydroxyl or —$OC_{1-3}$ alkyl;
$R^{11}$ is H or $C_{1-3}$ alkyl;
$R^{12}$ is H, $C_{1-3}$ alkyl, halogen, hydroxyl, —$OC_{1-3}$alkyl or amino;
$R^{13}$ is H or $C_{1-3}$ alkyl;
$R^{14}$ is H or $C_{1-3}$ alkyl;
$R^{15}$ is H or $C_{1-3}$ alkyl;
L is $CHR^{16}$, O, S, $NR^{17}$ or —C(O)—;
a is 0, 1, 2, 3, 4 or 5;
b is 0, 1, 2, 3, 4 or 5;
c is 0 or 1;
d is 1, 2 or 3;
$R^{16}$ is H, $C_{1-3}$ alkyl, —$OC_{1-3}$ alkyl, halogen, hydroxyl or amino, and
$R^{17}$ is H or $C_{1-3}$ alkyl;
with the proviso:
when $R^3$ is O, N—$R^{11}$, or S, and b is 0 or 1 then L is not O, S, or $NR^{17}$.

In another embodiment of the invention
$R^1$ is N or C—$R^{10}$;
$R^2$ is 5-member aromatic heterocycle or cycloalkenyl;
$R^3$ is O, N—$R^{11}$, CH—$R^{12}$ or S, —$CR^{13}$=$CR^{14}$—, —C(O) or —C≡C—;
$R^4$ is H, aromatic heterocycle, non-aromatic heterocycle, cycloalkyl, cycloalkenyl or aryl;
$R^5$ is H, halogen, hydroxyl, —$OC_{1-3}$ alkyl, or $C_{1-3}$ alkyl;
$R^6$ is H, $C_{1-3}$ alkyl, halogen, hydroxyl or —$OC_{1-3}$ alkyl;
$R^7$ is H or $C_{1-6}$ alkyl;
$R^8$ is H or $C_{1-6}$ alkyl;
$R^9$ is —COOH, —$S(O)_2OH$ or —$C_m$ alkyl;
$R^{10}$ is H, $C_{1-6}$ alkyl, halogen, hydroxyl or —$OC_{1-3}$ alkyl;
$R^{11}$ is H or $C_{1-3}$ alkyl;

$R^{12}$ is H, $C_{1-3}$ alkyl, halogen, hydroxyl, —$OC_{1-3}$alkyl or amino;
$R^{13}$ is H or $C_{1-3}$ alkyl;
$R^{14}$ is H or $C_{1-3}$ alkyl;
$R^{15}$ is H or $C_{1-3}$ alkyl;
L is $CHR^{16}$, O, S, $NR^{17}$ or —C(O)—;
a is 0, 1, 2, 3, 4 or 5;
b is 0, 1, 2, 3, 4 or 5;
c is 0 or 1;
d is 1, 2 or 3;
$R^{16}$ is H, $C_{1-3}$ alkyl, —$OC_{1-3}$ alkyl, halogen, hydroxyl or amino, and
$R^{17}$ is H or $C_{1-3}$ alkyl;
with the proviso:
when $R^3$ is O, N—$R^{11}$, or S, and b is 0 or 1 then L is not O, S, or $NR^{17}$.

In another embodiment of the invention
$R^1$ is N or C—$R^{10}$; and
$R^2$ is optionally substituted aromatic heterocycle, optionally substituted non-aromatic heterocycle or cycloalkenyl; and
$R^3$ is O; and
$R^4$ is optionally substituted aryl or H; and
$R^5$ is H; and
$R^6$ is H; and
$R^7$ is H; and
$R^8$ is H; and
$R^9$ is $P(O)(OH)_2$; and
$R^{10}$ is H; and
a is 1, 2, 4 or 5; and
b is 1, 2 or 4; and
c is 1; and
d is 3; and
L is $CHR^{16}$; and
$R^{16}$ is H.

In another embodiment of the invention $R^1$ is N or C—$R^{10}$; and
$R^2$ is optionally substituted aromatic heterocycle, optionally substituted non-aromatic heterocycle or cycloalkenyl; and
$R^3$ is O; and
$R^4$ is optionally substituted aryl; and
$R^5$ is H; and
$R^6$ is H; and
$R^7$ is H; and
$R^8$ is H; and
$R^9$ is $P(O)(OH)_2$; and
$R^{10}$ is H; and
a is 1 or 2; and
b is 1 or 2; and
c is 1; and
d is 3; and
L is $CHR^{16}$; and
$R^{16}$ is H.

In another embodiment of the invention
$R^1$ is N; and
$R^2$ is optionally substituted aromatic heterocycle, optionally substituted non-aromatic heterocycle or cycloalkenyl; and
$R^3$ is O; and
$R^4$ is optionally substituted aryl; and
$R^5$ is H; and
$R^6$ is H; and
$R^7$ is H; and
$R^8$ is H; and
$R^9$ is $P(O)(OH)_2$; and
a is 1 or 2; and
b is 1 or 2; and
c is 1; and
d is 3; and
L is $CHR^{16}$; and
$R^{16}$ is H.

In another embodiment of the invention
$R^1$ is C—$R^{10}$; and
$R^2$ is optionally substituted aromatic heterocycle, optionally substituted non-aromatic heterocycle or cycloalkenyl; and
$R^3$ is O; and
$R^4$ is H; and
$R^5$ is H; and
$R^6$ is H; and
$R^7$ is H; and
$R^8$ is H; and
$R^9$ is $P(O)(OH)_2$; and
$R^{10}$ is H; and
a is 2, 3, 4 or 5; and
b is 2, 3, 4 or 5; and
c is 1; and
d is 3; and
L is $CHR^{16}$; and
$R^{16}$ is H.

In another embodiment of the invention
$R^1$ is N or C—$R^{10}$;
$R^2$ is optionally substituted 5-member aromatic heterocycle, optionally substituted non-aromatic heterocycle or cycloalkenyl or cycloalkenyl;
$R^3$ is O, N—$R^{11}$ or CH—$R^{12}$;
$R^4$ is H or optionally substituted aryl;
$R^5$ is H, halogen, hydroxyl, —$OC_{1-3}$ alkyl, or $C_{1-3}$ alkyl;
$R^6$ is H, $C_{1-3}$ alkyl, halogen, hydroxyl or —$OC_{1-3}$ alkyl;
$R^7$ is H or $C_{1-6}$ alkyl;
$R^8$ is H;
$R^9$ is —$OPO_3H_2$, —$P(O)(OH)_2$, optionally substituted $C_{3-6}$ alkyl, —$S(O)_2OH$ or —$P(O)MeOH$;
$R^{10}$ is H;
$R^{11}$ is H;
$R^{12}$ is H;
L is $CHR^{16}$;
a is 2, 3, 4 or 5;
b is 1, 2, 3, 4 or 5;
c is 1;
d is 1, 2 or 3;
$R^{16}$ is H.

In another embodiment of the invention
$R^1$ is N;
$R^2$ is optionally substituted 5-member aromatic heterocycle, optionally substituted non-aromatic heterocycle or cycloalkenyl or cycloalkenyl;
$R^3$ is O, N—$R^{11}$ or CH—$R^{12}$;
$R^4$ is H or optionally substituted aryl;
$R^5$ is H, halogen, hydroxyl, —$OC_{1-3}$ alkyl, or $C_{1-3}$ alkyl;
$R^6$ is H, $C_{1-3}$ alkyl, halogen, hydroxyl or —$OC_{1-3}$ alkyl;
$R^7$ is H or $C_{1-6}$ alkyl;
$R^8$ is H;
$R^9$ is —$OPO_3H_2$, —$P(O)(OH)_2$, optionally substituted $C_{3-6}$ alkyl, —$S(O)_2OH$ or —$P(O)MeOH$;
$R^{10}$ is H;
$R^{11}$ is H;
$R^{12}$ is H;
L is $CHR^{16}$;
a is 2, 3, 4 or 5;
b is 1, 2, 3, 4 or 5;
c is 1;
d is 1, 2 or 3;
$R^{16}$ is H.

In another embodiment of the invention
$R^1$ is C—$R^{10}$;
$R^2$ is optionally substituted 5-member aromatic heterocycle, optionally substituted non-aromatic heterocycle or cycloalkenyl or cycloalkenyl;

$R^3$ is O, N—$R^{11}$ or CH—$R^{12}$;
$R^4$ is H or optionally substituted aryl;
$R^5$ is H, halogen, hydroxyl, —$OC_{1-3}$ alkyl, or $C_{1-3}$ alkyl;
$R^6$ is H, $C_{1-3}$ alkyl, halogen, hydroxyl or —$OC_{1-3}$ alkyl;
$R^7$ is H or $C_{1-6}$ alkyl;
$R^8$ is H;
$R^9$ is —$OPO_3H_2$, —$P(O)(OH)_2$, optionally substituted $C_{3-6}$ alkyl, —$S(O)_2OH$ or —$P(O)MeOH$;
$R^{10}$ is H;
$R^{11}$ is H;
$R^{12}$ is H;
L is $CHR^{16}$;
a is 2, 3, 4 or 5;
b is 1, 2, 3, 4 or 5;
c is 1;
d is 1, 2 or 3;
$R^{16}$ is H.
In another embodiment of the invention
$R^1$ is C—$R^{10}$;
$R^2$ is optionally substituted 5-member aromatic heterocycle, optionally substituted 5-member non-aromatic heterocycle or cycloalkenyl or cycloalkenyl;
$R^3$ is O;
$R^4$ is H or optionally substituted aryl;
$R^5$ is H, halogen, hydroxyl, —$OC_{1-3}$ alkyl, or $C_{1-3}$ alkyl;
$R^6$ is H, $C_{1-3}$ alkyl, halogen, hydroxyl or —$OC_{1-3}$ alkyl;
$R^7$ is H or $C_{1-6}$ alkyl;
$R^8$ is H;
$R^9$ is —$OPO_3H_2$, —$P(O)(OH)_2$, optionally substituted $C_{3-6}$ alkyl, —$S(O)_2OH$ or —$P(O)MeOH$;
$R^{10}$ is H;
L is $CHR^{16}$;
a is 2, 3, 4 or 5;
b is 1, 2, 3, 4 or 5;
c is 1;
d is 1, 2 or 3;
$R^{16}$ is H.
In another embodiment of the invention
$R^1$ is C—$R^{10}$;
$R^2$ is optionally substituted 5-member aromatic heterocycle, optionally substituted non-aromatic 5-member heterocycle or cycloalkenyl or cycloalkenyl;
$R^3$ is N—$R^{11}$;
$R^4$ is H or optionally substituted aryl;
$R^5$ is H, halogen, hydroxyl, —$OC_{1-3}$ alkyl, or $C_{1-3}$ alkyl;
$R^6$ is H, $C_{1-3}$ alkyl, halogen, hydroxyl or —$OC_{1-3}$ alkyl;
$R^7$ is H or $C_{1-6}$ alkyl;
$R^8$ is H;
$R^9$ is —$OPO_3H_2$, —$P(O)(OH)_2$, optionally substituted $C_{3-6}$ alkyl, —$S(O)_2OH$ or —$P(O)MeOH$;
$R^{10}$ is H;
$R^{11}$ is H;
L is $CHR^{16}$;
a is 2, 3, 4 or 5;
b is 1, 2, 3, 4 or 5;
c is 1;
d is 1, 2 or 3;
$R^{16}$ is H.
In another embodiment of the invention
$R^1$ is C—$R^{10}$;
$R^2$ is optionally substituted 5-member aromatic heterocycle, optionally substituted non-aromatic heterocycle or cycloalkenyl or cycloalkenyl;
$R^3$ is CH—$R^{12}$;
$R^4$ is H or optionally substituted aryl;
$R^5$ is H, halogen, hydroxyl, —$OC_{1-3}$ alkyl, or $C_{1-3}$ alkyl;
$R^6$ is H, $C_{1-3}$ alkyl, halogen, hydroxyl or —$OC_{1-3}$ alkyl;
$R^7$ is H or $C_{1-6}$ alkyl;
$R^8$ is H;
$R^9$ is —$OPO_3H_2$, —$P(O)(OH)_2$, optionally substituted $C_{3-6}$ alkyl, —$S(O)_2OH$ or —$P(O)MeOH$;
$R^{10}$ is H;
$R^{12}$ is H;
L is $CHR^{16}$;
a is 2, 3, 4 or 5;
b is 1, 2, 3, 4 or 5;
c is 1;
d is 1, 2 or 3;
$R^{16}$ is H.
Compounds of the invention are:
[3-({3-(2-furyl)-4-[(5-phenylpentyl)oxy]benzyl}amino)propyl]phosphonic acid;
[3-({3-(1,3-oxazol-2-yl)-4-[(5-phenylpentyl)oxy]benzyl}amino)propyl]phosphonic acid;
[3-({4-[(5-phenylpentyl)oxy]-3-(1,3-thiazol-2-yl)benzyl}amino)propyl]phosphonic acid;
[3-({3-(3-furyl)-4-[(5-phenylpentyl)oxy]benzyl}amino)propyl]phosphonic acid;
[3-({4-[(5-phenylpentyl)oxy]-3-(3-thienyl)benzyl}amino)propyl]phosphonic acid;
[3-({4-[(5-phenylpentyl)oxy]-3-(2-thienyl)benzyl}amino)propyl]phosphonic acid;
[3-({4-[3-(4-isobutylphenyl)propoxy]-3-(2-thienyl)benzyl}amino)propyl]phosphonic acid;
[3-({3-cyclopent-1-en-1-yl-4-[(5-phenylpentyl)oxy]benzyl}amino)propyl]phosphonic acid;
2-({4-[(5-phenylpentyl)oxy]-3-(2-thienyl)benzyl}amino)ethyl dihydrogen phosphate;
3-({4-[(5-phenylpentyl)oxy]-3-(2-thienyl)benzyl}amino)propane-1-sulfonic acid;
methyl[3-({4-[(5-phenylpentyl)oxy]-3-(2-thienyl)benzyl}amino)propyl]phosphinic acid;
2-({4-[(5-phenylpentyl)oxy]-3-(2-thienyl)benzyl}amino)propan-1-ol;
2-({4-[(5-phenylpentyl)oxy]-3-(2-thienyl)benzyl}amino)propane-1,3-diol;
{3-[({6-(3-furyl)-5-[(5-phenylpentyl)oxy]pyridin-2-yl}methyl)amino]propyl}phosphonic acid;
{3-[({5-[(5-phenylpentyl)oxy]-6-(2-thienyl)pyridin-2-yl}methyl)amino]propyl}phosphonic acid;
(3-{[4-(nonyloxy)-3-(2-thienyl)benzyl]amino}propyl)phosphonic acid;
(3-{[4-(decyloxy)-3-(2-thienyl)benzyl]amino}propyl)phosphonic acid;
3-({3-(5-fluoro-2-thienyl)-4-[(5-phenylpentyl)oxy]benzyl}amino)propyl]phosphonic acid;
(3-{[4-{[5-(3-methoxyphenyl)pentyl]oxy}-3-(2-thienyl)benzyl]amino}propyl)phosphonic acid;
(3-{[4-{[5-(4-methoxyphenyl)pentyl]oxy}-3-(2-thienyl)benzyl]amino}propyl)phosphonic acid;
(3-{[4-{[5-(4-fluorophenyl)pentyl]oxy}-3-(2-thienyl)benzyl]amino}propyl)phosphonic acid;
(3-{[3-(2-furyl)-4-({5-[3-(trifluoromethyl)phenyl]pentyl}oxy)benzyl]amino}propyl)phosphonic acid;
(3-{[3-(2-furyl)-4-{[5-(3-methoxyphenyl)pentyl]oxy}benzyl]amino}propyl)phosphonic acid
(3-{[4-{[5-(4-fluorophenyl)pentyl]oxy}-3-(2-furyl)benzyl]amino}propyl)phosphonic acid;
[3-({4-[4-(4-fluorophenyl)butoxy]-3-(2-thienyl)benzyl}amino)propyl]phosphonic acid;
[3-({4-[4-(4-fluorophenyl)butoxy]-3-(2-furyl)benzyl}amino)propyl]phosphonic acid;
(3-{[4-{[5-(3-fluoro-4-methoxyphenyl)pentyl]oxy}-3-(2-furyl)benzyl]amino}propyl)phosphonic acid;

(3-{[4-{[5-(3-fluoro-4-methoxyphenyl)pentyl]oxy}-3-(2-thienyl)benzyl]amino}propyl)phosphonic acid;
(3-{[4-{[5-(4-chlorophenyl)pentyl]oxy}-3-(2-furyl)benzyl]amino}propyl)phosphonic acid;
(3-{[4-{[5-(4-chlorophenyl)pentyl]oxy}-3-(2-thienyl)benzyl]amino}propyl)phosphonic acid;
(3-{[4-{[5-(3-chloro-4-methoxyphenyl)pentyl]oxy}-3-(2-furyl)benzyl]amino}propyl)phosphonic acid;
(3-{[4-{[5-(3-chloro-4-methoxyphenyl)pentyl]oxy}-3-(2-thienyl)benzyl]amino}propyl)phosphonic acid;
(3-{[3-(2-furyl)-4-{[5-(4-methoxyphenyl)pentyl]oxy}benzyl]amino}propyl)phosphonic acid;
(3-{[3-(3-furyl)-4-{[5-(3-methoxyphenyl)pentyl]oxy}benzyl]amino}propyl)phosphonic acid;
[3-({3-(1,3-oxazol-4-yl)-4-[(5-phenylpentyl)oxy]benzyl}amino)propyl]phosphonic acid;
[3-({3-(2-furyl)-4-[(5-phenylpentyl)oxy]benzyl}amino)-1-methylpropyl]phosphonic acid;
[3-({4-[(5-phenylpentyl)oxy]-3-(2-thienyl)benzyl}amino)propyl]phosphinic acid;
[3-({3-(5-fluoro-2-furyl)-4-[(5-phenylpentyl)oxy]benzyl}amino)propyl]phosphonic acid;
(3-{[4-{[5-(3-chlorophenyl)pentyl]oxy}-3-(2-furyl)benzyl]amino}propyl)phosphonic acid;
(3-{[3-(2-furyl)-4-{[5-(3-methylphenyl)pentyl]oxy}benzyl]amino}propyl)phosphonic acid;
[1,1-difluoro-3-({3-(5-fluoro-2-furyl)-4-[(5-phenylpentyl)oxy]benzyl}amino)propyl]phosphonic acid;
{3-[(1-{4-[(5-phenylpentyl)oxy]-3-(2-thienyl)phenyl}ethyl)amino]propyl}phosphonic acid;
[3-({4-[(5-phenylpentyl)oxy]-3-(1H-pyrazol-1-yl)benzyl}amino)propyl]phosphonic acid;
[3-({4-[(5-phenylpentyl)oxy]-3-(1H-pyrrol-1-yl)benzyl}amino)propyl]phosphonic acid;
[3-({3-(2-furyl)-4-[(5-phenylpentyl)oxy]benzyl}amino)propyl]phosphonic acid-d_2_;
[3-({3-(2-furyl)-4-[(5-phenylpentyl)amino]benzyl}amino)propyl]phosphonic acid;
[3-({3-(1,3-oxazol-2-yl)-4-[(5-phenylpentyl)amino]benzyl}amino)propyl]phosphonic acid;
[3-({4-[(5-phenylpentyl)amino]-3-(1,3-thiazol-2-yl)benzyl}amino)propyl]phosphonic acid;
(3-{[4-{[5-(2-fluorophenyl)pentyl]oxy}-3-(2-furyl)benzyl]amino}propyl)phosphonic acid;
(3-{[4-{[5-(2-fluorophenyl)pentyl]oxy}-3-(3-furyl)benzyl]amino}propyl)phosphonic acid;
[3-({2-fluoro-5-(2-furyl)-4-[(5-phenylpentyl)oxy]benzyl}amino)propyl]phosphonic acid;
(3-((4-((3-(3-bromo-4-isopropoxyphenyl)propyl)amino)-3-(furan-3-yl)benzyl)amino) propyl)phosphonic acid;
(3-((4-((3-(3-chloro-4-isobutylphenyl)propyl)amino)-3-(furan-3-yl)benzyl)amino)propyl)phosphonic acid;
(3-((4-((3-(3-chloro-4-isopropoxyphenyl)propyl)amino)-3-(furan-3-yl)benzyl)amino) propyl)phosphonic acid;
(3-((2-fluoro-4-((5-(4-fluorophenyl)pentyl)oxy)-5-(furan-2-yl)benzyl)amino) propyl)phosphonic acid;
(3-((2-fluoro-4-((5-(2-fluorophenyl)pentyl)oxy)-5-(furan-2-yl)benzyl)amino) propyl)phosphonic acid;
(3-((2-fluoro-4-((5-(4-fluorophenyl)pentyl)oxy)-5-(furan-3-yl)benzyl)amino) propyl)phosphonic acid;
(3-((2-fluoro-4-((5-(2-fluorophenyl)pentyl)oxy)-5-(furan-3-yl)benzyl)amino) propyl)phosphonic acid;
(3-((2-fluoro-4-((5-(4-fluorophenyl)pentyl)amino)-5-(furan-2-yl)benzyl)amino) propyl)phosphonic acid;
(3-((2-fluoro-4-((5-(2-fluorophenyl)pentyl)amino)-5-(furan-2-yl)benzyl)amino) propyl)phosphonic acid;
(3-((2-fluoro-4-((5-(4-fluorophenyl)pentyl)amino)-5-(furan-3-yl)benzyl)amino)propyl)phosphonic acid;
(3-((2-fluoro-4-((5-(2-fluorophenyl)pentyl)amino)-5-(furan-3-yl)benzyl)amino) propyl)phosphonic acid;
(3-((3-(furan-2-yl)-4-(3-(4-isobutylphenyl)propoxy)benzyl)amino)propyl)phosphonic acid;
(3-((4-(3-(3-cyano-4-isobutylphenyl)propoxy)-3-(furan-2-yl)benzyl)amino) propyl)phosphonic acid;
(3-((4-(3-(3-cyano-4-isopropoxyphenyl)propoxy)-3-(furan-2-yl)benzyl)amino) propyl)phosphonic acid;
(3-((4-(3-(3-cyano-4-isobutylphenyl)propoxy)-3-(thiophen-2-yl)benzyl)amino) propyl)phosphonic acid;
(3-((4-(3-(3-cyano-4-isopropoxyphenyl)propoxy)-3-(thiophen-2-yl)benzyl)amino) propyl)phosphonic acid;
(3-((3-(furan-3-yl)-4-(3-(4-isobutyl-3-(trifluoromethyl)phenyl)propoxy)benzyl)amino)propyl)phosphonic acid;
(3-((3-(furan-3-yl)-4-(3-(4-isopropoxy-3-(trifluoromethyl)phenyl)propoxy)benzyl)amino)propyl)phosphonic acid;
(3-((4-(3-(3-bromo-4-isobutylphenyl)propoxy)-3-(furan-3-yl)benzyl)amino)propyl)phosphonic acid;
(3-((4-(3-(3-bromo-4-isopropoxyphenyl)propoxy)-3-(furan-3-yl)benzyl)amino)propyl)phosphonic acid;
(3-((4-(3-(3-chloro-4-isobutylphenyl)propoxy)-3-(furan-3-yl)benzyl)amino)propyl)phosphonic acid;
(3-((4-(3-(3-chloro-4-isopropoxyphenyl)propoxy)-3-(furan-3-yl)benzyl)amino)propyl)phosphonic acid;
(3-((4-(3-(3-fluoro-4-isobutylphenyl)propoxy)-3-(furan-3-yl)benzyl)amino)propyl)phosphonic acid;
(3-((4-(3-(3-fluoro-4-isopropoxyphenyl)propoxy)-3-(furan-3-yl)benzyl)amino)propyl)phosphonic acid;
(3-((4-(3-(3-cyano-4-isobutylphenyl)propoxy)-3-(furan-3-yl)benzyl)amino)propyl)phosphonic acid;
(3-((4-(3-(3-cyano-4-isopropoxyphenyl)propoxy)-3-(furan-3-yl)benzyl)amino)propyl)phosphonic acid;
(3-((3-(furan-2-yl)-4-((3-(4-isobutylphenyl)propyl)amino)benzyl)amino)propyl)phosphonic acid;
(3-((3-(furan-2-yl)-4-((3-(4-isopropoxyphenyl)propyl)amino)benzyl)amino)propyl)phosphonic acid;
(3-((4-((3-(3-fluoro-4-isobutylphenyl)propyl)amino)-3-(furan-2-yl)benzyl)amino)propyl)phosphonic acid;
(3-((4-(3-(3-fluoro-4-isopropoxyphenyl)propoxy)-3-(thiophen-2-yl)benzyl)amino)propyl)phosphonic acid;
(3-((4-((3-(3-fluoro-4-isopropoxyphenyl)propyl)amino)-3-(furan-2-yl)benzyl)amino) propyl)phosphonic acid;
(3-((3-(furan-2-yl)-4-(3-(4-isobutyl-3-(trifluoromethyl)phenyl)propoxy)benzyl)amino)propyl)phosphonic acid;
(3-((4-(3-(4-isobutyl-3-(trifluoromethyl)phenyl)propoxy)-3-(thiophen-2-yl)benzyl)amino) propyl)phosphonic acid;
(3-((4-(3-(4-isopropoxy-3-(trifluoromethyl)phenyl)propoxy)-3-(thiophen-2-yl)benzyl)amino)propyl)phosphonic acid;
(3-((4-(3-(3-bromo-4-isobutylphenyl)propoxy)-3-(furan-2-yl)benzyl)amino)propyl)phosphonic acid;
(3-((4-(3-(3-bromo-4-isopropoxyphenyl)propoxy)-3-(furan-2-yl)benzyl)amino)propyl)phosphonic acid;
(3-((4-(3-(3-bromo-4-isobutylphenyl)propoxy)-3-(thiophen-2-yl)benzyl)amino)propyl)phosphonic acid;
(3-((4-(3-(3-bromo-4-isopropoxyphenyl)propoxy)-3-(thiophen-2-yl)benzyl)amino)propyl)phosphonic acid;
(3-((4-(3-(3-chloro-4-isobutylphenyl)propoxy)-3-(furan-2-yl)benzyl)amino)propyl)phosphonic acid;
(3-((4-(3-(3-chloro-4-isopropoxyphenyl)propoxy)-3-(furan-2-yl)benzyl)amino)propyl)phosphonic acid;
(3-((4-(3-(3-chloro-4-isobutylphenyl)propoxy)-3-(thiophen-2-yl)benzyl)amino)propyl)phosphonic acid;
(3-((4-(3-(3-chloro-4-isopropoxyphenyl)propoxy)-3-(thiophen-2-yl)benzyl)amino)propyl)phosphonic acid;

(3-((4-(3-(3-fluoro-4-isobutylphenyl)propoxy)-3-(furan-2-yl)benzyl)amino)propyl)phosphonic acid;
(3-((4-(3-(3-fluoro-4-isopropoxyphenyl)propoxy)-3-(furan-2-yl)benzyl)amino)propyl)phosphonic acid;
(3-((4-(3-(3-fluoro-4-isobutylphenyl)propoxy)-3-(thiophen-2-yl)benzyl)amino)propyl)phosphonic acid;
(3-((3-(furan-3-yl)-4-((3-(4-isopropoxy-3-(trifluoromethyl)phenyl)propyl)amino)benzyl)amino)propyl)phosphonic acid;
(3-((4-((3-(3-bromo-4-isobutylphenyl)propyl)amino)-3-(furan-3-yl)benzyl)amino)propyl)phosphonic acid;
(3-((3-(furan-3-yl)-4-((3-(4-isopropoxyphenyl)propyl)amino)benzyl)amino) propyl)phosphonic acid;
(3-((4-((3-(3-fluoro-4-isobutylphenyl)propyl)amino)-3-(furan-3-yl)benzyl)amino)propyl)phosphonic acid;
(3-((4-((3-(3-fluoro-4-isopropoxyphenyl)propyl)amino)-3-(furan-3-yl)benzyl)amino)propyl)phosphonic acid;
(3-((4-((3-(3-cyano-4-isobutylphenyl)propyl)amino)-3-(furan-3-yl)benzyl)amino)propyl)phosphonic acid;
(3-((4-((3-(3-cyano-4-isopropoxyphenyl)propyl)amino)-3-(furan-3-yl)benzyl)amino) propyl)phosphonic acid;
(3-((3-(furan-3-yl)-4-(3-(4-isobutyl-3-(trifluoromethyl)phenyl)propyl)amino)benzyl)amino)propyl)phosphonic acid;
(3-((4-((3-(3-cyano-4-isobutylphenyl)propyl)amino)-3-(furan-2-yl)benzyl)amino)propyl)phosphonic acid;
(3-((4-((3-(3-cyano-4-isopropoxyphenyl)propyl)amino)-3-(furan-2-yl)benzyl)amino) propyl)phosphonic acid;
(3-((3-(furan-2-yl)-4-(3-(4-isobutyl-3-(trifluoromethyl)phenyl)propyl)amino)benzyl)amino)propyl)phosphonic acid;
(3-((3-(furan-2-yl)-4-(3-(4-isopropoxy-3-(trifluoromethyl)phenyl)propyl)amino)benzyl)amino)propyl)phosphonic acid;
(3-((4-((3-(3-bromo-4-isobutylphenyl)propyl)amino)-3-(furan-2-yl)benzyl)amino) propyl)phosphonic acid;
(3-((4-((3-(3-bromo-4-isopropoxyphenyl)propyl)amino)-3-(furan-2-yl)benzyl)amino) propyl)phosphonic acid;
(3-((4-((3-(3-chloro-4-isobutylphenyl)propyl)amino)-3-(furan-2-yl)benzyl)amino) propyl)phosphonic acid;
(3-((4-((3-(3-chloro-4-isopropoxyphenyl)propyl)amino)-3-(furan-2-yl)benzyl)amino) propyl)phosphonic acid;
(3-((3-(furan-3-yl)-4-((3-(4-isobutylphenyl)propyl)amino)benzyl)amino)propyl)phosphonic acid;
(3-((2-fluoro-4-(6-(2-fluorophenyl)hexyl)-5-(furan-3-yl)benzyl)amino)propyl)phosphonic acid;
(3-((2-fluoro-4-(6-(2-fluorophenyl)hexyl)-5-(furan-2-yl)benzyl)amino)propyl)phosphonic acid;
(3-((2-fluoro-4-(6-(4-fluorophenyl)hexyl)-5-(furan-3-yl)benzyl)amino)propyl)phosphonic acid;
(3-((2-fluoro-4-(6-(4-fluorophenyl)hexyl)-5-(furan-2-yl)benzyl)amino)propyl)phosphonic acid;
(3-((3-(furan-2-yl)-4-(6-phenylhexyl)benzyl)amino)propyl) phosphonic acid.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, a hydrohalic acid such as hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahal & Camille G. Wermuth (Eds), Verlag Helvetica Chemica Acta—Zürich, 2002, 329-345). Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically. Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the sphingosine-1-phosphate receptors.

In another embodiment, there are provided pharmaceutical compositions including at least one compound of the invention in a pharmaceutically acceptable carrier.

In a further embodiment of the invention, there are provided methods for treating disorders associated with modulation of sphingosine-1-phosphate receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by S1P modulation: not limited to the treatment of diabetic retinopathy, other retinal degenerative conditions, dry eye, angiogenesis and wounds.

Therapeutic utilities of S1P modulators are ocular diseases, such as but not limited to: wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases such as but not limited to: various inflammatory diseases, including acute lung injury, its prevention, sepsis, tumor metastasis, atherosclerosis, pulmonary edemas, and ventilation-induced lung injury; or autoimmune diseases and immunosuppression such as but not limited to: rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermitatis, and organ transplantation; or allergies and other inflammatory diseases such as but not limited to: urticaria, bronchial asthma, and other airway inflammations including pulmonary emphysema and chronic obstructive pulmonary diseases; or cardiac protection such as but not limited to: ischemia reperfusion injury and atherosclerosis; or wound healing such as but not limited to: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation such as but not limited to: treatment of osteoporosis and various bone fractures including hip and ankles; or anti-nociceptive activity such as but not limited to: visceral pain, pain associated with diabetic neuropathy, rheumatoid arthritis, chronic knee and joint pain, tendonitis, osteoarthritis, neuropathic pains; or central nervous system neuronal activity in Alzheimer's disease, age-related neuronal injuries; or in organ transplant such as renal, corneal, cardiac or adipose tissue transplant.

In still another embodiment of the invention, there are provided methods for treating disorders associated with modulation of sphingosine-1-phosphate receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of ocular disease, wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases, various inflammatory diseases, including acute lung injury, its prevention, sepsis, tumor metastasis, atherosclerosis, pulmonary edemas, and ventilation-induced lung injury; or autoimmune diseases and immunosuppression, rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermititis, and organ transplantation; or allergies and other inflammatory diseases, urticaria, bronchial asthma, and other airway inflammations including pulmonary emphysema and chronic obstructive pulmonary diseases; or cardiac protection, ischemia reperfusion injury and atherosclerosis; or wound healing, scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation, treatment of osteoporosis and various bone fractures including hip and ankles; or anti-nociceptive activity, visceral pain, pain associated with diabetic neuropathy, rheumatoid arthritis, chronic knee and joint pain, tendonitis, osteoarthritis, neuropathic pains; or central nervous system neuronal activity in Alzheimer's disease, age-related neuronal injuries; or in organ transplant such as renal, corneal, cardiac or adipose tissue transplant.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier therefore. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and or alleviations of conditions which are responsive to treatment by agonists or functional antagonists of sphingosine-1-phosphate receptors. Thus, in further embodiments of the invention, there are provided methods for treating a disorder associated with modulation of sphingosine-1-phosphate receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of formula I according to the invention can be prepared analogously to conventional methods as understood by the person skilled in the art of synthetic organic chemistry. The synthetic schemes set forth below, illustrate how compounds according to the invention can be made. Those skilled in the art will be able to routinely modify and/or adapt the following scheme to synthesize any compounds of the invention covered by Formula I.

In Scheme 1, hydroxybenzaldehydes react with hydroxylated compounds in the presence of triphenylphosphine and diethyl azodicarboxylate to give the corresponding ether intermediate. This intermediate is coupled with the boronic acid or the stannate of the corresponding $R^2$ group to give the corresponding intermediate. This intermediate reacts with 3-aminopropylphosphonic acid to give a derivative of Formula I.

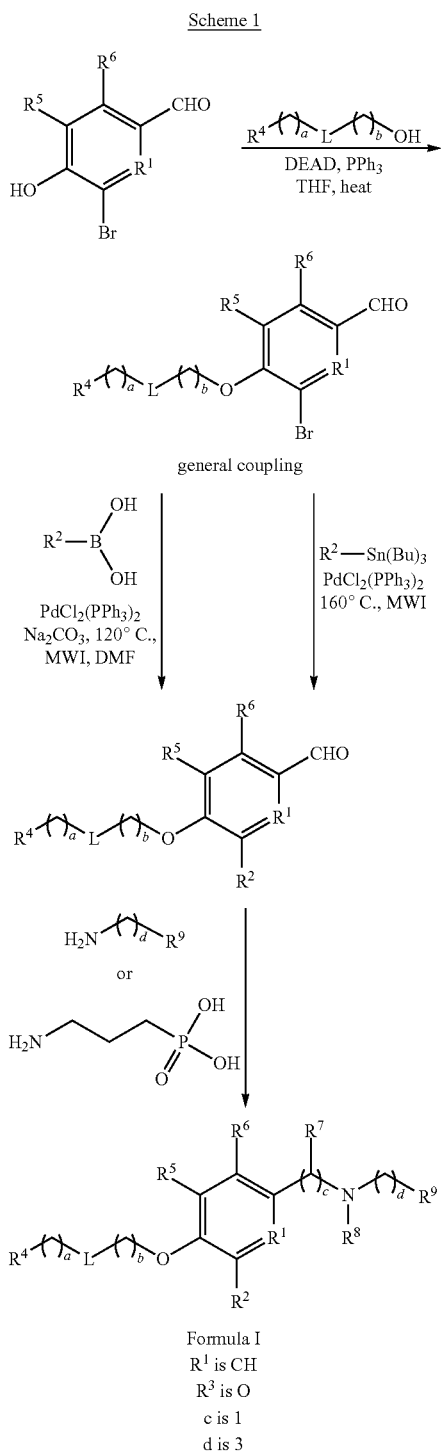

In Scheme 2, picolinaldehydes react with brominated compounds in the presence of potassium carbonate to give the corresponding intermediate. This intermediate is coupled with the boronic acid of the corresponding $R^2$ group to give the corresponding intermediate, which reacts with 3-aminopropylphosphonic acid to give a derivative of Formula I.

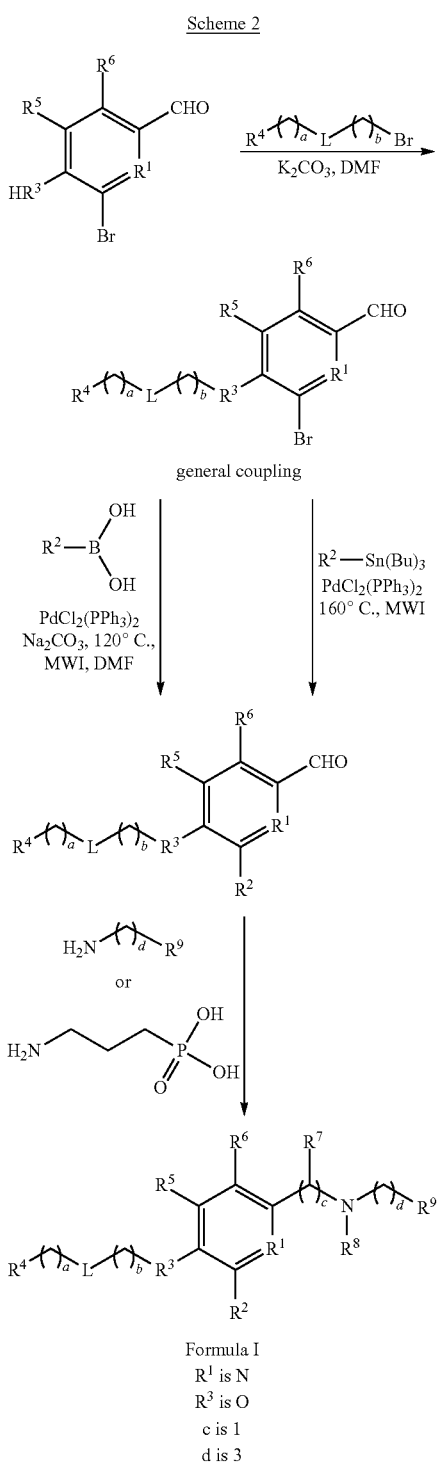

Scheme 2

Formula I
R¹ is N
R³ is O
c is 1
d is 3

BRIEF DESCRIPTION OF THE DRAWINGS

FIG. 1 shows the results of Compound 6, [3-({4-[(5-phenylpentyl)oxy]-3-(2-thienyl)benzyl}amino)propyl]phosphonic acid, in the Lymphopenia Assay in Mice. Lymphopenia was induced by S1P1 agonist, Compound 6, (10 mg/kg) in mice (24, 48, 72 Hours).

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of protium $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diasteroisomeric isomers, chromatographic separation may be employed.

Compound names were generated with ACD version 12.00 or 8.00; and Intermediates and reagent names used in the examples were generated with software such as Chem Bio Draw Ultra version 12.0 or Auto Nom 2000 from MDL ISIS Draw 2.5 SP1.

In general, characterization of the compounds is performed according to the following methods:

NMR spectra were recorded on 300 and/or 600 MHz Varian and acquired at room temperature. Chemical shifts in ppm were referenced either to internal TMS or to the solvent signal. Some proton NMR (nuclear magnetic resonance) spectra were taken either at 60 MHz on a Varian T-60 spectrometer or at 300 MHz on a Varian Inova system or 400 MHz Bruker. The spectra of all products were consistent with their structures.

All the reagents, solvents, catalysts for which the synthesis was not described are purchased from chemical vendors such as Sigma Aldrich, Fluka, Bio-Blocks, Combi-blocks, TCI, VWR, Lancaster, Oakwood, Trans World Chemical, Alfa, AscentScientific LLC., Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by column chromatography (Auto-column) on an Teledyne-ISCO CombiFlash with a silica column, unless noted otherwise.

The following abbreviations are used in the examples:

| | |
|---|---|
| s, m, h, d | second, minute, hour, day |
| psi | pound per square inch |
| $CH_2Cl_2$ | dichloromethane |
| DMF | N,N-dimethylformamide |
| NaOH | sodium hydroxide |
| MeOH | methanol |
| $CD_3OD$ | deuterated methanol |
| HCl | hydrochloric acid |
| $Na_2SO_4$ | sodium sulfate |
| rt | room temperature |
| $MgSO_4$ | magnesium sulfate |
| EtOAc | ethyl acetate |
| $CDCl_3$ | deuterated chloroform |
| DMSO-$d_6$ | deuterated dimethyl sulfoxide |
| Auto-column | automated flash liquid chromatography |
| TFA | trifluoroacetic acid |
| THF | tetrahydrofuran |
| HMPA | hexamethylphosphoramide |
| DEAD | diethyl azodicarboxylate |
| $Na_2CO_3$ | sodium carbonate |
| $Cs_2CO_3$ | cesium carbonate |
| M | molar |
| $PdCl_2(PPh_3)_2$ | bis(triphenylphosphine)palladium(II) chloride |
| $Pd(PPh_3)_4$ | tetrakis(triphenylphosphine)palladium(0) |
| AcOH | acetic acid |
| $K_2CO_3$ | potassium carbonate |
| CuI | copper iodide |
| $MnO_2$ | manganese oxide |
| $MgCl_2$ | magnesium chloride |
| NaCl | sodium chloride |
| MeMgBr | methylmagnesium bromide |
| $CHCl_3$ | chloroform |
| TBAH | tetrabutylammonium hydroxide |
| IPA | isopropyl alcohol |
| $CH_3CN$ | acetonitrile |
| NBS | N-Bromosuccinimide |

The following synthetic schemes illustrate how compounds according to the invention can be made. Those skilled in the art will be routinely able to modify and/or adapt the following schemes to synthesize any compound of the invention covered by Formula I. Some compounds of this invention can generally be prepared in one step from commercially available or literature starting materials.

Example 1

Intermediate 1

3-bromo-4-(5-phenyl-pentyloxy)-benzldehyde

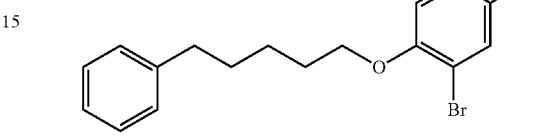

A solution of 5-phenyl-pentan-1-ol [CAS 10521-91-2] (4.50 mL, 26.6 mmol), 3-bromo-4-hydroxybenzaldehyde [CAS 2973-78-6] (5.36 g, 26.7 mmol), triphenylphosphine (9.1 g, 34.6 mmol) and DEAD, (14.5 mL, 40% in toluene, ~1.2 eqv) in THF (100 mL) was reacted at rt for 1 h, followed by heating to 60° C. for 2 days. Silica gel was added and the solvents were removed under vacuum. Auto-column: chromatography on a Teledyne-ISCO CombiFlash with a silica column with 9.5 hexane/0.5 EtOAc to 9 Hexanes/1 EtOAc gave Intermediate 1 as a clear oil that solidified upon standing, 5.38 g (58%).

$^1$H NMR (300 MHz, $CDCl_3$): δ 9.83 (s, 1H), 8.07 (d, J=2.1 Hz, 1H), 7.78 (dd, J=8.7, 2.1 Hz, 1H), 7.28-7.18 (m, 5H), 6.96 (d, J=8.4 Hz, 1H), 4.11 (t, J=6.3 Hz, 2H), 2.67 (t, J=7.2 Hz, 2H), 1.92-1.55 (m, 6H).

Intermediates 11 through 17, 20, 62, 67 and 68 were prepared from the corresponding alcohol and benzaldehyde in a similar manner to the procedure described in Example 1 for Intermediate 1. The starting materials used and the results are described below in Table 1.1.

TABLE 1.1

| Interm. No. | IUPAC name Structure | Starting materials | $^1$H NMR δ (ppm) for Intermediate |
|---|---|---|---|
| 11 | 3-bromo-4-{[5-(4-fluorophenyl)pentyl]oxy}benzaldehyde | 5-(4-fluorophenyl)pentan-1-ol [158429-64-2] 3-bromo-4-hydroxybenzaldehyde [2973-78-6] | (300 MHz, DMSO-$d_6$) δ: 9.84 (s, 1 H), 8.08 (d, J = 2.0 Hz, 1 H), 7.90 (dd, J = 8.5, 2.0 Hz, 1 H), 7.29 (d, J = 8.6 Hz, 1 H), 7.25-7.09 (m, 2 H), 7.07 (t, J = 8.9 Hz, 2 H), 4.17 (t, J = 6.4 Hz, 2 H), 2.59 (t, J = 7.6 Hz, 2 H), 1.83-1.76 (m, 2 H), 1.63 (quin, J = 7.6 Hz, 2 H), 1.46 (quin, J = 7.6 Hz, 2 H). |
| 12 | 3-bromo-4-{[5-(4-chlorophenyl)pentyl]oxy}benzaldehyde | 5-(4-chlorophenyl)pentan-1-ol [14469-86-4] 3-bromo-4-hydroxybenzaldehyde [2973-78-6] | (600 MHz, DMSO-$d_6$) δ: 9.84 (s, 1 H), 8.09 (d, J = 2.0 Hz, 1 H), 7.90 (dd, J = 8.5, 2.0 Hz, 1 H), 7.33-7.27 (m, 3 H), 7.23 (d, J = 8.4 Hz, 2 H), 4.17 (t, J = 6.4 Hz, 2 H), 2.59 (t, J = 7.6 Hz, 2 H), 1.84-1.74 (m, 2 H), 1.64 (quin, J = 7.6 Hz, 2 H), 1.46 (quin, J = 7.6 Hz, 2 H). |

TABLE 1.1-continued

| Interm. No. | IUPAC name Structure | Starting materials | $^1$H NMR δ (ppm) for Intermediate |
|---|---|---|---|
| 13 | 3-bromo-4-{[5-(3-fluoro-4-methoxyphenyl)pentyl]oxy}benzaldehyde | 5-(3-fluoro-4-methoxyphenyl)pentan-1-ol [1216172-07-4] 3-bromo-4-hydroxy-benzaldehyde [2973-78-6] | (300 MHz, DMSO-$d_6$) δ: 9.84 (s, 1 H), 8.09 (d, J = 2.0 Hz, 1 H), 7.90 (dd, J = 8.5, 2.0 Hz, 1 H), 7.30 (d, J = 8.5 Hz, 1 H), 7.00-7.09 (m, 2 H), 6.95 (m, 1 H), 4.17 (t, J = 6.4 Hz, 2 H), 3.79 (s, 3 H), 2.51-2.58 (m, 2 H), 1.79 (m, 2 H), 1.62 (m, 2 H), 1.45 (m, 2 H). |
| 14 | 3-bromo-4-{[5-(3-chloro-4-methoxyphenyl)pentyl]oxy}benzaldehyde | 5-(3-chloro-4-methoxyphenyl)pentan-1-ol [1216171-69-5] 3-bromo-4-hydroxy-benzaldehyde [2973-78-6] | (600 MHz, DMSO-$d_6$) δ: 9.84 (s, 1 H), 8.08 (d, J = 2.0 Hz, 1 H), 7.90 (dd, J = 8.5, 2.0 Hz, 1 H), 7.29 (d, J = 8.6 Hz, 1 H), 7.25 (d, J = 2.0 Hz, 1 H), 7.12 (dd, J = 8.4, 2.0 Hz, 1 H), 7.03 (d, J = 8.4 Hz, 1 H), 4.17 (t, J = 6.4 Hz, 2 H), 3.81 (s, 3 H), 2.54 (t, J = 7.6 Hz, 2 H), 1.83-1.76 (m, 2 H), 1.62 (quin, J = 7.6 Hz, 2 H), 1.45 (quin, J = 7.6 Hz, 2 H). |
| 15 | 3-bromo-4-({5-[3-(trifluoromethyl)phenyl]pentyl}oxy)benzaldehyde | 5-[3-(trifluoromethyl)phenyl]pentan-1-ol [1005407-83-9] 3-bromo-4-hydroxy-benzaldehyde [2973-78-6] | (300 MHz, DMSO-$d_6$) δ: 9.90-9.79 (m, 1 H), 8.09 (dd, J = 4.7, 2.0 Hz, 1 H), 7.92 (ddd, J = 11.7, 8.5, 2.0 Hz, 1 H), 7.58-7.49 (m, 3 H), 7.31 (t, J = 8.1 Hz, 2 H), 4.18 (t, J = 6.3 Hz, 2 H), 2.71 (t, J = 7.6 Hz, 2 H), 1.81 (m, 2 H), 1.68 (m, 2 H), 1.49 (m, 2 H). |
| 16 | 3-bromo-4-[4-(4-fluorophenyl)butoxy]benzaldehyde | 4-(4-fluorophenyl)butan-1-ol [40283-05-4] 3-bromo-4-hydroxy-benzaldehyde [2973-78-6] | (300 MHz, DMSO-$d_6$) δ: 9.85 (s, 1 H), 8.09 (d, J = 2.0 Hz, 1 H), 7.90 (dd, J = 8.5, 2.0 Hz, 1 H), 7.30 (d, J = 8.5 Hz, 1 H), 7.25 (m, 2 H), 7.13-7.05 (m, 2 H), 4.24-4.17 (m, 2 H), 2.66 (t, J = 6.9 Hz, 2 H), 1.81-1.72 (m, 4 H). |
| 17 | 3-bromo-4-{[5-(3-methoxyphenyl)pentyl]oxy}benzaldehyde | 5-(3-methoxyphenyl)pentan-1-ol [66004-20-4] 3-bromo-4-hydroxy-benzaldehyde [2973-78-6] | (300 MHz, DMSO-$d_6$) δ: 9.84 (s, 1H), 8.09 (d, J = 2.1 Hz, 1H), 7.90 (dd, J = 8.5, 2.1 Hz, 1H), 7.30 (d, J = 8.6 Hz, 1H), 7.17 (t, J = 8.0 Hz, 1H), 6.82-6.68 (m, 3H), 4.18 (t, J = 6.4 Hz, 2H), 3.72 (s, 3H), 2.57 (t, J = 7.6 Hz, 2H), 1.87-1.71 (m, 2H), 1.65 (m, 2H), 1.47 (m, 2H). |
| 20 | 3-bromo-4-[(5-phenylpentyl)oxy]benzaldehyde-d2 | 5-phenylpentan-1-ol-d2 Intermediate 22 3-bromo-4-hydroxy-benzaldehyde [2973-78-6] | (300 MHz, CDCl$_3$) δ: 9.83 (s, 1H), 8.07 (d, J = 1.8 Hz, 1H), 7.78 (dd, J = 8.4, 2.1 Hz, 1H), 7.28-7.18 (m, 5H), 6.95 (d, J = 8.4 Hz, 1H), 2.67 (J = 7.5 Hz, 2H), 1.90-1.57 (series of m, 6H). |

TABLE 1.1-continued

| Interm. No. | IUPAC name Structure | Starting materials | $^1$H NMR δ (ppm) for Intermediate |
|---|---|---|---|
| 62 | 3-bromo-4-{[5-(2-fluorophenyl)pentyl]oxy}benzaldehyde | 4-(2-fluorophenyl)pentan-1-ol Intermediate 61 3-bromo-4-hydroxy-benzaldehyde [2973-78-6] | (300 MHz, DMSO-d$_6$) δ: 9.85 (s, 1H), 8.09 (d, J = 2.1 Hz, 1H), 7.90 (dd, J = 8.5, 2.1 Hz, 1H), 7.34-7.26 (m, 2H), 7.23 (m, 1H), 7.16-7.07 (m, 2H), 4.18 (t, J = 6.4 Hz, 2H), 2.00 (t, J = 7.5 Hz, 2H), 1.81 (m, 2H), 1.63 (m, 2H), 1.49 (m, 2H). |
| 67 | 3-bromo-4-((5-(m-tolyl)pentyl)oxy)benzaldehyde | 5-(m-tolyl)pentan-1-ol (from reduction of 3-methyl-benzenepentanoic acid [105401-68-1] with borane dimethyl sulfide complex) 3-bromo-4-hydroxybenzaldehyde [2973-78-6] | (300 MHz, CDCl$_3$) δ: 7.20-6.97 (s of m, 4H), 3.64 (t, J = 6.9 Hz, 2H), 2.59 (t, J = 7.2 Hz, 2H), 2.33 (s, 3H), 1.68-1.46 (ser. of m, 6H). |
| 68 | 3-bromo-4-((5-(3-chlorophenyl)pentyl)oxy)benzaldehyde | 5-(3-chlorophenyl)pentan-1-ol (prepared by reduction of 3-chlorobenzenepentanoic acid [625129-63-7] with borane dimethyl sulfide complex [13292-87-0]) 3-bromo-4-hydroxy-benzaldehyde [2973-78-6] | (300 MHz, CDCl$_3$) δ: 7.17-7.01 (series of m, 4H), 3.64 (t, J = 6.6 Hz, 2H), 2.60 (t, J = 7.2 Hz, 2H), 1.64-1.39 (series of m, 6H). |

Example 2

Intermediate 4

6-bromo-5-hydroxypicolinaldehyde

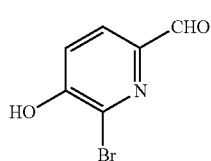

A solution of 2-bromo-6-(hydroxymethyl)pyridin-3-ol [CAS 168015-04-1](~1 g, ~5 mmol) in dioxane (100 mL) was treated with MnO$_2$ (3.0 g, 29.3 mmol, 85%) at 100° C. for 16-18 h. The mixture was filtered, and concentrated onto silica gel. Auto-column (7:3 hexane/EtOAc gave Intermediate 4 as a solid 0.6 g (60%).

$^1$H NMR (300 MHz, CDCl$_3$): δ 9.91 (s, 1H), 7.92 (d, 4.2 Hz, 1H), 7.43 (d, 4.2 Hz, 1H)

Example 3

Intermediate 5

6-bromo-5-(5-phenylpentyloxy)picolinaldehyde

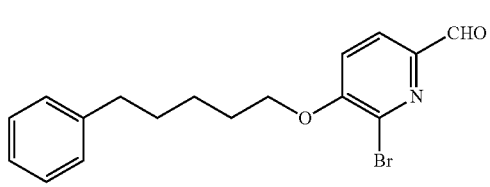 [SMILES: O=Cc1ccc(OCCCCCc2ccccc2)c(Br)n1]

Reaction of Intermediate 4 (0.59 g, 2.92 mmol), (5-bromopentyl)benzene [CAS 14469-83-1] (0.80 g, 3.52 mmol) and K$_2$CO$_3$ (0.8 g, 5.79 mmol) in DMF (15 mL) at 100° C. for 4 h followed by a standard aqueous work-up and auto-column purification gave the product Intermediate 5: as a clear oil (0.67 g, 66%).

¹H NMR (300 MHz, CDCl₃): δ 9.93 (s, 1H), 7.92 9 s, J=8.1 Hz, 1H), 7.28-7.18 (m, 6H), 4.12 (t, J=6.0 Hz, 2H), 2.67 (t, J=7.2 Hz, 2H), 1.93-1.55 (series of m, 6H).

Intermediates 19 and 65 were prepared from the corresponding alkylbromide and benzaldehyde in a similar manner to the procedure described in Example 3 for Intermediate 5. The starting materials used and the results are described below in Table 1.2.

treated with silica gel (24 g) and PCC (14.9 g, 69 mmol) at rt for ~18 h. The mixture was concentrated, and purified by chromatography on silica gel (ethyl acetate-hexane) to give 3-bromo-4-((5-phenylpentyl)amino)benzaldehyde Intermediate-21 (3.5 g, 44%).

(400 MHz, DMSO-d₆) δ: 9.63 (s, 1H), 7.91 (s, 1H), 7.70-7.69 (m, 1H), 7.20-7.10 (m, 5H), 6.82-6.80 (m, 1H), 6.29-

TABLE 1.2

| Interm. No. | IUPAC name Structure | Starting materials | ¹H NMR δ (ppm) for Intermediate |
|---|---|---|---|
| 19 | 3-bromo-4-{[5-(4-methoxyphenyl)pentyl]oxy}benzaldehyde | See Example-3: 1-(5-bromophenyl)-4-methoxy benzene [14469-84-2] 3-bromo-4-hydroxybenzaldehyde [2973-78-6] | (300 MHz, DMSO-d₆) δ: 9.84 (s, 1 H), 8.09 (d, J = 2.0 Hz, 1 H), 7.90 (dd, J = 8.5, 2.0 Hz, 1 H), 7.30 (d, J = 8.5 Hz, 1 H), 7.14-7.05 (m, 2 H), 6.82 (d, J = 8.7 Hz, 2 H), 4.17 (t, J = 6.4 Hz, 2 H), 3.71 (s, 3 H), 2.53 (t, J = 6.8 Hz, 2 H), 1.79 (m, 2 H), 1.61 (m, 2 H), 1.46 (m, 2 H). |
| 65 | 5-bromo-2-fluoro-4-((5-phenylpentyl)oxy)benzaldehyde | See Example 3: (5-bromopentyl) benzene [CAS14469-83-1] 5-Bromo-2-fluoro-4-hydroxybenzaldehyde [914397-21-0] | (400 MHz, CDCl₃) δ: 10.20 (s, 1H), 8.10-8.08 (m, 1 H), 7.53-7.50 (m, 5 H), 7.65-7.55 (m, 1H), 4.10-4.05 (m, 2H), 2.70-2.65 (m, 2H), 2.00-1.50 (ser. or m, 6H). |

Example 4

Intermediate 21

(3-bromo-4-((5-phenylpentyl)amino)phenyl)methanol

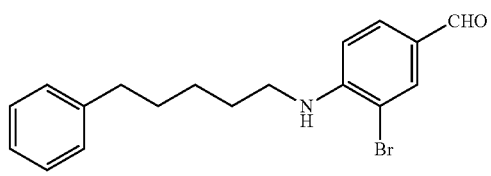 [SMILES: O=Cc1ccc(NCCCCCc2ccccc2)c(Br)c1]

A solution of 5-bromopentylbenzene [14469-83-1] (4 g, 17.6 mmol) in HMPA (55 g) was treated with 4-amino-3-bromobenzemethanol [146019-46-7] and dry K₂CO₃ (4.87 g, 35.2 mmol) for ~18 h at 120° C. The mixture was cooled to rt, poured onto water (600 mL) and extracted with ethyl acetate (200 mL). The organic phase was washed with water (200 mL), dried over Na₂SO₄, concentrated, and purified by chromatography (ethyl acetate/hexane) to give (3-bromo-4-((5-phenylpentyl)amino)phenyl)methanol (2.24 g, 37%). A solution of (3-bromo-4-((5-phenylpentyl)amino)phenyl) methanol (8.0 g, 23 mmol) in dichloromethane (160 mL) was 6.27 (m, 1H), 3.28-3.24 (m, 2H), 2.52-2.50 (m, 2H), 1.60-1.58 (m, 4H), 1.36-1.33 (m, 2H).

Example 5

Intermediate 22

5-phenylpentan-1-ol-d2

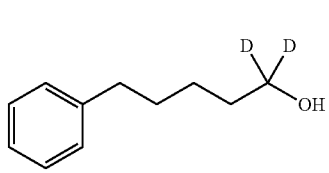 [SMILES: [2H]C([2H])(O)CCCCc1ccccc1]

A mixture of benzenepentanoic acid [2270-20-4] (2.0 g, 11.1 mmol) in THF (15 mL) at 0° C. was treated with LiAlD₄ (1.7 mL, 1.5H in THF). The solution was stirred at rt for ~18 h, and quenched with Rochelle's salt solution and stirred for 1 h at rt. The organic was extracted with 1:1 hexane:ethyl acetate (200 mL). The pooled organic layers were dried over MgSO₄, filtered, and evaporated to give a crude residue. The residue was purified on auto-column (silica gel 8:2 hexane: ethyl acetate) to give Intermediate 22.

(300 MHz, CDCl$_3$) δ: 7.28-7.16 (m, 5H), 2.63 (t, J=6.6 Hz, 2H), 1.70-1.57 (m, 4H), 1.43-1.50 (m, 2H).

Example 6

Intermediate 23

Diethyl 3-tosyloxy-1,1-difluoro-propylphosphonate

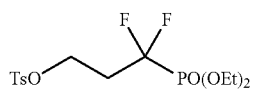

Diethyl 3-hydroxy-1,1-difluoro-propylphosphonate [1225194-19-3] (4.4 g, 0.019 mol) was dissolved in CH$_2$Cl$_2$ (20 mL) and triethylamine (7.7 g) and treated with TsCl (5.4 g, 0.029 mol) followed by DMAP (0.23 g, 0.0019 mol) at rt for 2 h. After 2 h, an additional portion of TsCl (0.6 g) was added. After 30 m, the reaction mixture was partitioned between water and CH$_2$Cl$_2$. The organic layer was filtered and concentrated in vacuo. The residue was dissolved in 1:1 hexanes:CH$_2$Cl$_2$ (100 mL) and applied to 85 g flash silica gel (topped with Na$_2$SO$_4$ and equilibrated with hexanes). The column was eluted with hexanes-ethyl acetate. Intermediate 23 weighed 6.3 g (94%). $^1$H NMR (CDCl$_3$) 7.2-7.8 (AB, 4H); 3.9-4.4 (m, 6H); 2.0-3.0 (m, 5H), 1.4 (t, 6H).

Example 7

Intermediate 24

Ethyl hydrogen 3-azido-1,1-difluoro-propylphosphonate

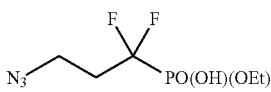

Intermediate 23 (16 g, 0.046 mol) was mixed with NaN$_3$ (6.0 g, 0.092 mol) and DMF (100 mL) and the mixture was stirred 1 week. The solvent was removed at high vacuum, and the residue was taken up in water (100 mL) and washed with ethyl acetate (100 mL). The aqueous layer was mixed with 1 M HCl (130 mL) and washed with CH$_2$Cl$_2$ (4×100 mL). The aqueous was concentrated to 100 mL volume, and stirred with EtOH (150 mL). The solid was filtered away, and the filtrate was concentrated to 50 mL and stirred with EtOH (100 mL). The solid was filtered away, and the filtrate was concentrated and dried at high vacuum. The 15 g residue was taken on to the next step.

Example 8

Intermediate 25

Ethyl hydrogen 3-amino-1,1-difluoro-propylphosphonate

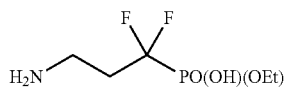

Intermediate 24 was mixed with 10% Pd[C] (1.4 g) and EtOH (100 mL), and hydrogenated overnight at 60 psi H$_2$. The mixture was filtered, and the residue was triturated with ether (2×100 mL) to leave 14.1 g.

Example 9

Intermediate 26

(3-Amino-1,1-difluoro-propyl)-phosphonic acid

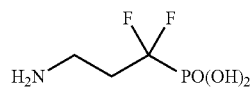

Intermediate 25 was mixed with 6 M aq. HCl (250 mL) in a flask equipped with a reflux condenser. The mixture was heated overnight at 115° C. and concentrated in vacuo. The residue was reconcentrated twice from water (50 mL) and twice from EtOH (100 mL). The oily residue was triturated with THF. The combined triturates were concentrated and set aside. The residue was stirred with IPA until a free-flowing solid had formed. The solid was collected to yield 4.2 g of Intermediate 26. $^1$H NMR (D$_2$O) 4.7 (s, 2.3H, —NH$_2$, —OH); 3.2 (t, 2H); 2.2-2.5 (m, 2H).

Example 22

Intermediate 60

5-(2-fluorophenyl)pent-4-yn-1-ol

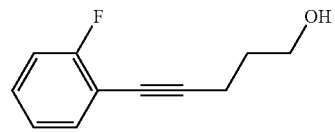 [SMILES: OCCCC#Cc1ccccc1F]

1-Bromo-2-fluorobenzene [1072-85-1] (3.0 g, 17 mmol, 1.0 equiv) and pent-4-yn-1-ol [5390-04-5] (2.3 mL, 25 mmol, 1.5 equiv) were dissolved in acetonitrile (40 mL). CuI (0.13 g, 0.68 mmol, 0.04 equiv) and TEA (3.4 mL, 25 mmol, 1.5 equiv) was added to the stirred solution followed by tetrakis (triphenylphosphine)palladium(0) (0.39 g, 0.34 mmol, 0.02 equiv). The solution was heated at reflux for 16 hours. The solution was cooled, filtered through Celite, the Celite pad rinsed with EtOAc and the solvent removed by rotoevaporation. Column chromatography (9:1 hexanes:ethyl acetate) of the residue afforded pure 5-(2-fluorophenyl)pent-4-yn-1-ol Intermediate 60 (1.3 g, 43%).

$^1$H NMR (600 MHz, DMSO-d$_6$) δ: 7.42 (t, J=7.48 Hz, 1H), 7.38-7.32 (m, 1H), 7.22 (t, J=9.10 Hz, 1H), 7.14 (t, J=7.56 Hz, 1H), 4.50 (t, J=5.21 Hz, 1H), 3.49 (q, J=5.92 Hz, 2H), 2.47 (t, J=7.12 Hz, 2H), 1.66 (quin, J=6.68 Hz, 2H).

Example 23

Intermediate 61

5-(2-fluorophenyl)pentan-1-ol

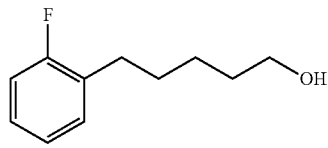 [SMILES: OCCCCCc1ccccc1F]

5-(2-Fluorophenyl)pent-4-yn-1-ol Intermediate 60 was dissolved in anhydrous EtOH (100 mL) and Pd(C) (0.22 g) was added to the stirred solution. A balloon of H$_2$ was affixed to the reaction vessel and the solution hydrogenated overnight. The solution was filtered through Celite, the Celite pad rinsed with EtOAc and the solvent removed by rotoevaporation. The residue was a mix of alkenyl isomers. Therefore, it was redissolved in EtOH and Pd (C) (0.22 g) added. A balloon of H$_2$ was affixed to the reaction vessel and the solution hydrogenated overnight. The solution was filtered through Celite, the Celite pad rinsed with EtOAc and the solvent removed by rotoevaporation. Column chromatography (45:1 hexanes:ethyl acetate) of the residue afforded pure 4-(2-fluorophenyl)pentan-1-ol Intermediate 61 (1.6 g, 73%).

$^1$H NMR (300 MHz, DMSO-d$_6$) δ: 7.33-7.18 (m, 2H), 7.16-7.05 (m, 2H), 4.33 (t, J=5.13 Hz, 1H), 3.42-3.33 (m, 2H), 2.59 (t, J=7.55 Hz, 2H), 1.55 (quin, J=7.55 Hz, 2H), 1.49-1.37 (m, 2H), 1.37-1.24 (m, 2H).

Example 10

Intermediate 2

3-furan-2-yl-4-(5-phenyl-pentyloxy)-benzaldehyde

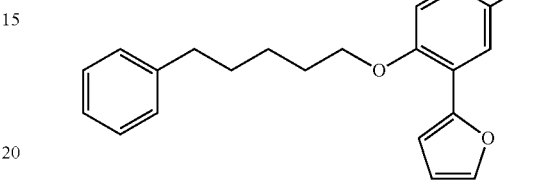

Intermediate 1 (0.65 g, 1.87 mmol) in DMF (14 mL) was reacted with tributyl(furan-2-yl)stannane [CAS 118486-94-5] (1.2 mL, 3.70 mmol) and PdCl$_2$(PPh$_3$)$_2$ (0.197 g, ~15 mol %) at 160° C. for 15 m with MWI (microwave irradiation: Biotage Initiator 2.5). The reaction mixture was diluted with 2:1 EtOAc/Hexanes (~150 mL), washed with water (3×), and dried over MgSO$_4$, filtered and concentrated onto silica gel. Auto-column (9.5 hexane/0.5 EtOAc) gave Intermediate 2: as a white solid, 0.44 g (70%).

$^1$H NMR (300 MHz, CDCl$_3$): δ 9.94 (s, 1H), 8.37 (d, J=2.1 Hz, 1H), 7.77-7.74 (m, 1H), 7.49 (d, J=1.2 Hz, 1H), 7.30-7.10 (m, 5H), 7.04-6.90 (m, 2H), 6.50 (brs, 1H), 4.21-4.05 (m, 2H), 2.70-2.60 (m, 2H), 2.10-1.50 (series m, 6H).

Intermediates 27 through 49, 51, 53, 63, 64 and 66 were prepared from the corresponding bromo-aldehyde and appropriate reagents in a similar manner to the procedure described in Example 10 for Intermediate 2. The reagents used and the results are described below in Table 2.

Intermediate 7 was prepared in a similar manner to the procedure described in Example 11.

TABLE 2

| Interm. No. | IUPAC name Structure | Starting materials | $^1$H NMR δ (ppm) for Intermediate |
|---|---|---|---|
| 7 | 4-((5-phenylpentyl)oxy)-3-(thiophen-2-yl)benzaldehyde | Intermediate 1 as Example 11 thiophen-2-yl boronic acid, [13331-23-2] | (300 MHz, CDCl$_3$) δ: 9.92 (s, 1H), 8.17 (d, J = 2.1 Hz, 1H), 7.75 (dd, J = 2.1, 8.4 Hz, 1H), 7.56 (dd, J = 1.2, 3.9 Hz, 1H), 7.36 (dd, J = 1.2, 5.4 Hz, 1H), 7.30-7.24 (m, 2H), 7.20-7.17 (m, 3H), 7.10 (dd, J = 3.9, 5.4 Hz, 1H), 7.04 (d, J = 8.4 Hz, 1H), 4.16 (t, J = 6.6 Hz, 2H), 2.66 (t, J = 7.2 Hz, 2H), 2.01-1.91 (m, 2H), 1.78-1.68 (m, 2H), 1.64-1.54 (m, 2H). |

TABLE 2-continued

| Interm. No. | IUPAC name Structure | Starting materials | $^1$H NMR δ (ppm) for Intermediate |
|---|---|---|---|
| 27 | 3-(2-furyl)-4-[(5-phenylpentyl)oxy]benzaldehyde-d² 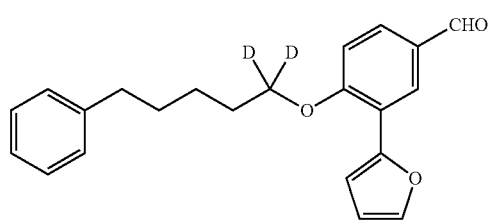 [SMILES: O=Cc1ccc(OCCCCCc2ccccc2)c(-c2ccco2)c1] | Intermediate 20 tributyl(furan-2-yl)stannane [118486-94-5] | (600 MHz, CDCl$_3$) δ: 9.94 (s, 1H), 8.37 (d, J = 1.8 Hz, 1H), 7.76 (dd, J = 9.0, 1.8 Hz, 1H), 7.49 (s, 1H), 7.28-7.17 (m, 5H), 7.02 (d, J = 8.4 Hz, 1H), 6.95 (d, J = 3.6 Hz, 1H), 6.49-6.48 (m, 1H), 2.66 (t, J = 7.8 Hz, 2H), 1.95 (J = 7.2 Hz, 2H), 1.76-1.71 (m, 2H), 1.60-1.53 (m, 2H). |
| 28 | 4-{[5-(4-fluorophenyl)pentyl]oxy}-3-(2-thienyl)benzaldehyde 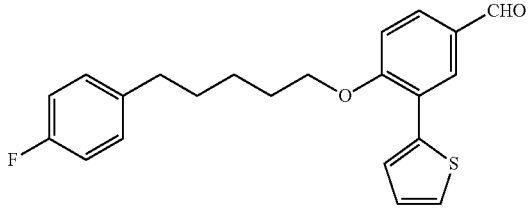 | Intermediate 11 2-(tributylstannyl) thiophene [54663-78-4] | (600 MHz, DMSO-d$_6$) δ: 9.93 (s, 1 H), 8.25 (d, J = 2.1 Hz, 1 H), 7.84 (dd, J = 2.1, 8.5 Hz, 1 H), 7.68 (dd, J = 1.2, 3.8 Hz, 1 H), 7.60 (dd, J = 1.0, 5.1 Hz, 1 H), 7.33 (d, J = 8.8 Hz, 1 H), 7.25-7.20 (m, 2 H), 7.15 (dd, J = 3.8, 5.3 Hz, 1 H), 7.10-7.05 (m, 2 H), 4.24 (t, J = 6.3 Hz, 2 H), 2.60 (t, J = 7.6 Hz, 2 H), 1.93-1.84 (m, 2 H), 1.69-1.61 (m, 2 H), 1.56-1.47 (m, 2 H). |
| 29 | 4-{[5-(3-methoxyphenyl)pentyl]oxy}-3-(2-thienyl)benzaldehyde 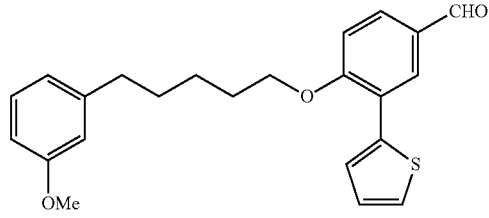 | Intermediate 17 2-(tributylstannyl) thiophene [54663-78-4] | (600 MHz, DMSO-d$_6$) δ: 9.93 (s, 1 H), 8.25 (d, J = 2.1 Hz, 1 H), 7.83 (dd, J = 2.1, 8.5 Hz, 1 H), 7.70-7.67 (m, 1 H), 7.60 (d, J = 4.7 Hz, 1 H), 7.33 (d, J = 8.5 Hz, 1 H), 7.19-7.13 (m, 2 H), 6.79-6.75 (m, 2 H), 6.75-6.71 (m, 1 H), 4.25 (t, J = 6.3 Hz, 2 H), 3.31 (s, 3 H), 2.58 (t, J = 7.6 Hz, 2 H), 1.94-1.84 (m, 2 H), 1.72-1.62 (m, 2 H), 1.57-1.47 (m, 2 H). |
| 30 | 3-(2-Furyl)-4-{[5-(3-methoxyphenyl)pentyl]oxy}benzaldehyde 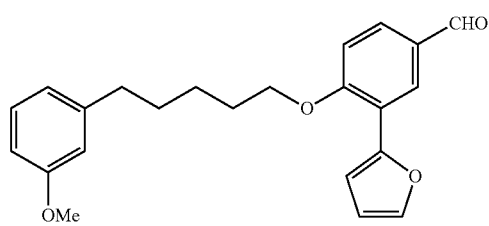 | Intermediate 17 2-(tributylstannyl) furan [118486-94-5] | (600 MHz, DMSO-d$_6$) δ: 9.94 (s, 1 H), 8.26 (d, J = 2.1 Hz, 1 H), 7.85-7.82 (m, 1 H), 7.81-7.79 (m, 1 H), 7.33 (d, J = 8.8 Hz, 1 H), 7.19-7.15 (m, 1 H), 6.95-6.93 (m, 1 H), 6.79-6.75 (m, 2 H), 6.75-6.71 (m, 1 H), 6.61 (dd, J = 1.9, 3.4 Hz, 1 H), 4.24 (t, J = 6.3 Hz, 2 H), 3.72 (s, 3 H), 2.59 (t, J = 7.6 Hz, 2 H), 1.93-1.86 (m, 2 H), 1.72-1.64 (m, 2 H), 1.54-1.46 (m, 2 H). |
| 31 | 4-{[5-(4-fluorophenyl)pentyl]oxy}-3-(2-furyl)benzaldehyde 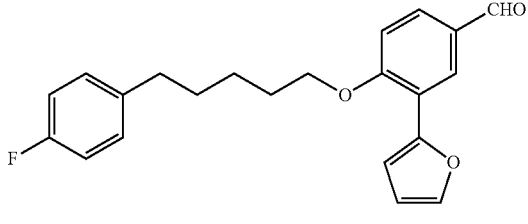 | Intermediate 11 2-(tributylstannyl) furan [118486-94-5] | (600 MHz, DMSO-d$_6$) δ: 9.94 (s, 1 H), 8.26 (d, J = 2.1 Hz, 1 H), 7.84 (dd, J = 2.3, 8.5 Hz, 1 H), 7.81-7.80 (m, 1 H), 7.33 (d, J = 8.5 Hz, 1 H), 7.25-7.20 (m, 2 H), 7.10-7.04 (m, 2 H), 6.94-6.90 (m, 1 H), 6.61 (dd, J = 1.8, 3.2 Hz, 1 H), 4.24 (t, J = 6.3 Hz, 2 H), 2.61 (t, J = 7.5 Hz, 2 H), 1.93-1.86 (m, 2 H), 1.70-1.63 (m, 2 H), 1.52-1.45 (m, 2 H). |

TABLE 2-continued

| Interm. No. | IUPAC name Structure | Starting materials | $^1$H NMR δ (ppm) for Intermediate |
|---|---|---|---|
| 32 | 4-{[5-(4-chlorophenyl)pentyl]oxy}-3-(2-furyl)benzaldehyde | Intermediate 12 2-(tributylstannyl) furan [118486-94-5] | (600 MHz, DMSO-d$_6$) δ: 9.94 (s, 1 H), 8.27 (d, J = 2.1 Hz, 1 H), 7.84 (dd, J = 2.2, 8.7 Hz, 1 H), 7.81 (d, J = 1.8 Hz, 1 H), 7.35-7.29 (m, 3 H), 7.27-7.21 (m, 2 H), 6.92 (d, J = 3.2 Hz, 1 H), 6.61 (dd, J = 1.9, 3.4 Hz, 1 H), 4.24 (t, J = 6.3 Hz, 2 H), 2.62 (t, J = 7.6 Hz, 2 H), 1.93-1.86 (m, 2 H), 1.71-1.63 (m, 2 H), 1.53-1.45 (m, 2 H). |
| 33 | 4-{[5-(3-chloro-4-methoxyphenyl)pentyl]oxy}-3-(2-furyl)benzaldehyde | Intermediate 14 2-(tributylstannyl) furan [118486-94-5] | (600 MHz, DMSO-d$_6$) δ: 9.94 (s, 1 H), 8.26 (d, J = 2.1 Hz, 1 H), 7.84 (dd, J = 1.6, 8.7 Hz, 1 H), 7.81 (d, J = 1.5 Hz, 1 H), 7.33 (d, J = 8.8 Hz, 1 H), 7.26 (d, J = 1.5 Hz, 1 H), 7.13 (d, J = 8.5 Hz, 1 H), 7.02 (d, J = 8.5 Hz, 1 H), 6.92 (d, J = 3.2 Hz, 1 H), 6.60 (dd, J = 1.8, 3.2 Hz, 1 H), 4.24 (t, J = 6.2 Hz, 2 H), 3.31 (s, 3 H), 2.56 (t, J = 7.5 Hz, 2 H), 1.93-1.84 (m, 2 H), 1.69-1.61 (m, 2 H), 1.52-1.43 (m, 2 H). |
| 34 | 4-{[5-(3-fluoro-4-methoxyphenyl)pentyl]oxy}-3-(2-thienyl)benzaldehyde | Intermediate 13 2-(tributylstannyl) thiophene [54663-78-4] | (600 MHz, DMSO-d$_6$) δ: 9.93 (s, 1 H), 8.25 (d, J = 2.1 Hz, 1 H), 7.84 (dd, J = 2.1, 8.5 Hz, 1 H), 7.68 (dd, J = 1.2, 3.5 Hz, 1 H), 7.61-7.57 (m, 1 H), 7.33 (d, J = 8.5 Hz, 1 H), 7.15 (dd, J = 3.7, 5.1 Hz, 1 H), 7.08-7.00 (m, 2 H), 6.94 (d, J = 7.9 Hz, 1 H), 4.24 (t, J = 6.3 Hz, 2 H), 3.79 (s, 3 H), 2.55 (t, J = 7.6 Hz, 2 H), 1.92-1.84 (m, 2 H), 1.68-1.61 (m, 2 H), 1.55-1.47 (m, 2 H). |
| 35 | 4-{[5-(3-chloro-4-methoxyphenyl)pentyl]oxy}-3-(2-thienyl)benzaldehyde | Intermediate 14 2-(tributylstannyl) thiophene [54663-78-4] | (600 MHz, DMSO-d$_6$) δ: 9.93 (s, 1 H), 8.25 (d, J = 2.1 Hz, 1 H), 7.84 (dd, J = 2.1, 8.5 Hz, 1 H), 7.68 (dd, J = 1.2, 3.5 Hz, 1 H), 7.60-7.57 (m, 1 H), 7.33 (d, J = 8.8 Hz, 1 H), 7.26 (d, J = 2.1 Hz, 1 H), 7.17-7.10 (m, 2 H), 7.02 (d, J = 8.5 Hz, 1 H), 4.24 (t, J = 6.3 Hz, 2 H), 3.80 (s, 3 H), 2.55 (t, J = 7.5 Hz, 2 H), 1.91-1.84 (m, 2 H), 1.68-1.60 (m, 2 H), 1.54-1.47 (m, 2 H). |
| 36 | 4-{[5-(4-methoxyphenyl)pentyl]oxy}-3-(2-thienyl)benzaldehyde | Intermediate 19 2-(tributylstannyl) thiophene [54663-78-4] | (600 MHz, DMSO-d$_6$) δ: 9.93 (s, 1 H), 8.25 (d, J = 2.1 Hz, 1 H), 7.83 (dd, J = 2.1, 8.5 Hz, 1 H), 7.70-7.66 (m, 1 H), 7.60 (dd, J = 1.2, 5.0 Hz, 1 H), 7.33 (d, J = 8.5 Hz, 1 H), 7.15 (dd, J = 3.7, 5.1 Hz, 1 H), 7.12-7.07 (m, 2 H), 6.85-6.79 (m, 2 H), 4.24 (t, J = 6.3 Hz, 2 H), 3.71 (s, 3 H), 2.54 (t, J = 7.5 Hz, 2 H), 1.91-1.84 (m, 2 H), 1.68-1.59 (m, 2 H), 1.56-1.47 (m, 2 H). |

TABLE 2-continued

| Interm. No. | IUPAC name Structure | Starting materials | $^1$H NMR δ (ppm) for Intermediate |
|---|---|---|---|
| 37 | 3-(2-furyl)-4-({5-[3-(trifluoromethyl)phenyl]pentyl}oxy)benzaldehyde | Intermediate 15 2-(tributylstannyl)furan [118486-94-5] | (600 MHz, DMSO-$d_6$) δ: 9.94 (s, 1 H), 8.26 (d, J = 2.1 Hz, 1 H), 7.84 (dd, J = 2.1, 8.5 Hz, 1 H), 7.80 (d, J = 1.8 Hz, 1 H), 7.57 (s, 1 H), 7.55-7.48 (m, 3 H), 7.33 (d, J = 8.5 Hz, 1 H), 6.93 (d, J = 3.2 Hz, 1 H), 6.60 (dd, J = 1.9, 3.4 Hz, 1 H), 4.25 (t, J = 6.5 Hz, 2 H), 2.72 (t, J = 7.6 Hz, 2 H), 1.96-1.87 (m, 2 H), 1.75-1.67 (m, 2 H), 1.57-1.47 (m, 2 H). |
| 38 | 4-[4-(4-fluorophenyl)butoxy]-3-(2-thienyl)benzaldehyde | Intermediate 16 2-(tributylstannyl)thiophene [54663-78-4] | (600 MHz, DMSO-$d_6$) δ: 9.94 (s, 1 H), 8.26 (d, J = 2.1 Hz, 1 H), 7.84 (dd, J = 2.1, 8.5 Hz, 1 H), 7.70 (dd, J = 1.2, 3.8 Hz, 1 H), 7.63 (dd, J = 1.2, 5.0 Hz, 1 H), 7.33 (d, J = 8.8 Hz, 1 H), 7.26-7.21 (m, 2 H), 7.16 (dd, J = 3.7, 5.1 Hz, 1 H), 7.13-7.07 (m, 2 H), 4.27 (t, J = 6.0 Hz, 2 H), 2.67 (t, J = 7.3 Hz, 2 H) 1.93-1.73 (m, 4 H). |
| 39 | 4-[4-(4-fluorophenyl)butoxy]-3-(2-furyl)benzaldehyde | Intermediate 16 2-(tributylstannyl)furan [118486-94-5] | (600 MHz, DMSO-$d_6$) δ: 9.94 (s, 1 H), 8.26 (d, J = 2.1 Hz, 1 H), 7.84 (dd, J = 2.1, 8.5 Hz, 1 H), 7.82-7.80 (m, 1 H), 7.32 (d, J = 8.5 Hz, 1 H), 7.28-7.22 (m, 2 H), 7.15-7.08 (m, 2 H), 6.93 (d, J = 3.5 Hz, 1 H), 6.64 (dd, J = 1.8, 3.2 Hz, 1 H), 4.27 (t, J = 6.3 Hz, 2 H), 2.67 (t, J = 7.5 Hz, 2 H), 1.91-1.83 (m, 2 H), 1.83-1.74 (m, 2 H). |
| 40 | 3-(2-furyl)-4-{[5-(4-methoxyphenyl)pentyl]oxy}benzaldehyde | Intermediate 19 2-(tributylstannyl)furan [118486-94-5] | (600 MHz, DMSO-$d_6$) δ: 9.94 (s, 1 H), 8.26 (d, J = 2.3 Hz, 1 H), 7.83 (dd, J = 2.1, 8.5 Hz, 1 H), 7.81 (d, J = 1.2 Hz, 1 H), 7.33 (d, J = 8.5 Hz, 1 H), 7.11 (d, J = 8.5 Hz, 2 H), 6.92 (d, J = 3.2 Hz, 1 H), 6.82 (d, J = 8.5 Hz, 2 H), 6.61 (dd, J = 1.9, 3.4 Hz, 1 H), 4.24 (t, J = 6.5 Hz, 2 H), 3.71 (s, 3 H), 2.55 (t, J = 7.6 Hz, 2 H), 1.92-1.85 (m, 2 H), 1.68-1.61 (m, 2 H), 1.53-1.44 (m, 2 H). |
| 41 | 3-(3-furyl)-4-{[5-(3-methoxphenyl)pentyl]oxy}benzaldehyde | Intermediate 17 tributyl(furan-3-yl)stannane [87453-06-3] | (600 MHz, DMSO-$d_6$) δ: 9.92 (s, 1 H), 8.15-8.12 (m, 2 H), 7.81 (dd, J = 2.2, 8.7 Hz, 1 H), 7.77 (t, J = 1.8 Hz, 1 H), 7.30 (d, J = 8.5 Hz, 1 H), 7.71 (t, J = 7.9 Hz, 1 H), 7.09-7.06 (m, 1 H), 6.78-6.75 (m, 2 H), 6.74-6.71 (m, 1 H), 4.22 (t, J = 6.5 Hz, 2 H), 3.31 (s, 3 H), 2.58 (t, J = 7.6 Hz, 2 H), 1.93-1.85 (m, 2 H), 1.71-1.62 (m, 2 H), 1.52-1.43 (m, 2 H). |

TABLE 2-continued

| Interm. No. | IUPAC name Structure | Starting materials | $^1$H NMR δ (ppm) for Intermediate |
|---|---|---|---|
| 42 | 4-{[5-(3-fluoro-4-methoxyphenyl)pentyl]oxy}-3-(2-furyl)benzaldehyde | Intermediate 13 2-(tributylstannyl) furan [118486-94-5] | (600 MHz, DMSO-d$_6$) δ: 9.94 (s, 1 H), 8.26 (d, J = 2.3 Hz, 1 H), 7.84 (dd, J = 2.1, 8.5 Hz, 1 H), 7.81 (d, J = 1.2 Hz, 1 H), 7.33 (d, J = 8.5 Hz, 1 H), 7.08-7.01 (m, 2 H), 6.95 (d, J = 7.9 Hz, 1 H), 6.92 (d, J = 3.5 Hz, 1 H), 6.60 (dd, J = 1.8, 3.2 Hz, 1 H), 4.24 (t, J = 6.3 Hz, 2 H), 3.79 (s, 3 H), 2.56 (t, J = 7.5 Hz, 2 H), 1.94-1.84 (m, 2 H), 1.71-1.60 (m, 2 H), 1.53-1.42 (m, 2 H). |
| 43 | 4-{[5-(4-chlorophenyl)pentyl]oxy}-3-(2-thienyl)benzaldehyde | Intermediate 12 2-(tributylstannyl) thiophene [54663-78-4] | |
| 45 | 3-(5-fluorofuran-2-yl)-4-((5-phenylpentyl)oxy)benzaldehyde | Intermediate 1 tributyl(5-fluoro-2-furanyl)-stannane [616874-33-0] | (300 MHz, CDCl$_3$) δ: 9.93 (s, 1H), 8.20 (d, J = 2.4 Hz, 1H), 7.73 (dd, J = 6.3, 2.1 Hz, 1H), 7.29-7.17 (m, 5H), 7.02 (d, J = 8.7 Hz, 1H), 6.82 (d, J = 3.3 Hz, 1H), 5.51 (dd, J = 3.3, 3.6 Hz, 1H), 4.17 (t, J = 6.3 Hz, 2H), 2.671 (t, J = 7.5 Hz, 2H), 1.99-1.56 (series of m, 5H). |
| 46 | 4-((5-(3-chlorophenyl)pentyl)oxy)-3-(furan-2-yl)benzaldehyde | Intermediate 68 tributyl(furan-2-yl)stannane [118486-94-5] | (300 MHz, CDCl$_3$) δ: 9.95 (s, 1H), 8.38 (d, J = 2.4 Hz, 1H), 7.80-7.78 (m, 1H), 7.51-7.49 (m, 1H), 7.18-6.94 (m, 6H), 6.51-6.49 (m, 1H), 4.18 (t, 6.6 Hz, 2H), 2.64 (t, J = 7.8 Hz, 2H), 2.00-1.55 (m, 6H). |
| 47 | 3-(furan-2-yl)-4-((5-phenylpentyl)amino)benzaldehyde | Intermediate 21 2-(tributylstannyl) furan [118486-94-5] | (300 MHz, CDCl$_3$) δ: 9.77 (s, 1H), 7.91 (d, J = 1.8 Hz, 1H), 7.70 (dd, J = 8.7, 2.1 Hz, 1H), 7.49 (dd, J = 1.5, 0.3 Hz, 1 H), 7.31-7.16 (series of m, 5H), 6.72 (d, J = 8.7 Hz, 1H), 6.60 (dd, J = 3.0, 0.9 Hz, 1H), 6.53 (dd, J = 1.5, 2.1 Hz, 1H), 3.25 (t, J = 7.5 Hz, 2H), 2.65 (t, J = 7.5 Hz, 2H), 1.79-1.24 (series of m, 4H), 0.98-0.84 (m, 2H). |

TABLE 2-continued

| Interm. No. | IUPAC name Structure | Starting materials | $^1$H NMR δ (ppm) for Intermediate |
|---|---|---|---|
| 48 | 3-(oxazol-2-yl)-4-((5-phenylpentyl)amino)benzaldehyde | Intermediate 21 2-(tributylstannyl)- oxazole [145214-05-7] | (300 MHz, CDCl$_3$) δ: 9.78 (s, 1H), 8.40 (d, J = 2.1 Hz, 1H), 7.80 (dd, J = 1.8, 9.0 Hz, 1H), 7.68 (s, 1H), 7.28-7.17 (m, 6H), 6.78 (dd, J = 8.7 Hz, 1H), 3.35 (t, J = 7.2 Hz, 2H), 6.66 (t, J = 7.5 Hz, 2H), 1.83-1.52 (series of m, 6H). |
| 49 | 4-((5-phenylpentyl)amino)-3-(thiazol-2-yl)benzaldehyde | Intermediate 21 2-(tributylstannyl)- thiazole [121359-48-6] | (300 MHz, CDCl$_3$) δ: 9.76 (s, 1H), 8.18 (d, J = 1.8 Hz, 1H), 7.76-7.73 (m, 2H), 7.28-7.16 (m, 6H), 6.78 (d, J = 8.7 Hz, 1H), 3.34 (t, J = 7.2 Hz, 2H), 2.66 (t, J = 7.5 Hz, 2H), 1.80-1.52 (series of m, 6H). |
| 51 | 3-(furan-2-yl)-4-((5-(m-tolyl)pentyl)oxy)benzaldehyde | Intermediate 67 tributyl(furan-2- yl)stannane [CAS 118486-94- 5] | (300 MHz, CDCl$_3$) δ: 9.95 (s, 1H), 8.38 (d, J = 2.4 Hz, 1H), 7.77 (dd, J = 8.7, 2.1 Hz, 1H), 7.50 (dd, J = 1.2, 0.9 Hz, 1H), 7.20-6.96 (series of m, 6H), 6.50 (dd, J = 1.8, 1.8 Hz, 1H), 4.18 (t, J = 6.6 Hzm 2H), 2.63 (t, J = 7.5 Hz, 2H), 2.32 (s, 3H), 2.04-1.24 (series of m, 6H). |
| 53 | 3-(1-ethoxyvinyl)-4-((5-phenylpentyl)oxy)benzaldehyde | Intermediate 1 tributyl(1- ethoxyethenyl)- stannane [97674-02-7] | |
| 63 | 4-{[5-(2-fluorophenyl)pentyl]oxy}-3-(2-furyl)benaldehyde | Intermediate 62 tributyl(furan-2- yl)stannane [118486-94-5] | (300 MHz, DMSO-d$_6$) δ: 9.95 (s, 1 H), 8.28 (d, J = 2.1 Hz, 1 H), 7.86 (d, J = 1.8 Hz, 1 H), 7.83 (m, 1 H), 7.34 (d, J = 8.8 Hz, 1 H), 7.32-7.19 (m, 2 H), 7.18-7.07 (m, 2 H), 6.95 (d, J = 3.2 Hz, 1 H), 6.66-6.59 (m, 1 H), 4.26 (t, J = 6.4 Hz, 2 H), 2.66 (t, J = 7.2 Hz, 2 H), 1.98-1.84 (m, 2 H), 1.77-1.59 (m, 2 H), 1.61-1.42 (m, 2 H). |
| 64 | 4-{[5-(2-fluorophenyl)pentyl]oxy}-3-(3-furyl)benzaldehyde | Intermediate 62 tributyl(furan-3- yl)stannane [87453-06-3] | (600 MHz, DMSO-d$_6$) δ: 9.92 (s, 1 H), 8.14 (d, J = 2.1 Hz, 1 H), 8.13-8.12 (m, 1 H), 7.81 (dd, J = 2.3, 8.5 Hz, 1 H), 7.77 (t, J = 1.8 Hz, 1 H), 7.30 (d, J = 8.8 Hz, 2 H), 7.25-7.20 (m, 1 H), 7.14-7.09 (m, 2 H), 7.07 (dd, J = 0.7, 1.9 Hz, 1 H), 4.22 (t, J = 6.5 Hz, 2 H), 2.64 (t, J = 7.5 Hz, 2 H), 1.94-1.83 (m, 2 H), 1.71-1.61 (m, 2 H), 1.56-1.42 (m, 2 H). |

TABLE 2-continued

| Interm. No. | IUPAC name Structure | Starting materials | ¹H NMR δ (ppm) for Intermediate |
|---|---|---|---|
| 66 | 2-fluoro-5-(furan-2-yl)-4-((5-phenylpentyl)oxy)benzaldehyde | Intermediate 65 2-(tributylstannyl) furan [118486-94-5] | (600 MHz, CDCl₃) δ: 10.24 (s, 1H), 8.35 (d, J = 8.4 Hz, 1H), 7.48-7.47 (m, 1H), 7.30-7.18 (ser of m, 5H), 6.86-6.85 (m, 1H), 6.68 (d, J = 12.0 Hzm 1H), 6.47 (dd, J = 3.6, 3.0 Hz, 1H), 4.13 (t, J = 6.6 hz, 2H), 2.67 (t, J = 7.8 hz, 2H), 2.00-1.95 (m, 2H), 1.77-1.72 (m, 2H), 1.61-1.57 (m, 2H). |

Example 11

Intermediate 3

3-(furan-3-yl)-4-((5-phenylpentyl)oxy)benzaldehyde

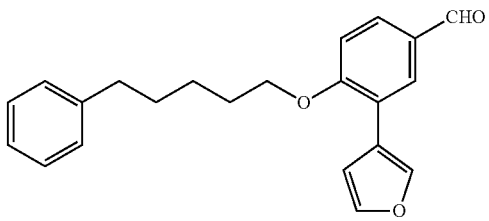 [SMILES: O=Cc1ccc(OCCCCCc2ccccc2)c(-c2ccoc2)c1]

A mixture of Intermediate 1 (290 mg, 0.87 mmol) in DMF (12 mL) was reacted with furan-3-yl boronic acid [CAS 5552-70-0] (195 mg, 1.74 mmol) Na₂CO₃ (2.8 mL, 2M) and PdCl₂(PPh₃)₂ (69 mg, ~11 mol %) at 120° C. for 20 m with MWI (microwave irradiation: Biotage Initiator 2.5). The reaction mixture was diluted with water, and extracted (two times) with 1:1 EtOAc:hexanes (200 mL). The organic layers were washed with water (three times), dried over MgSO₄, filtered and concentrated onto silica gel. Auto-column (9 hexane/1 EtOAc) gave Intermediate 3 230 mg (29%).
¹H NMR (300 MHz, CDCl₃): δ 9.92 (s, 1H), 8.03 (d, J=2.4 Hz, 1H), 7.75-7.72 (m, 1H), 7.48 (s, 1H), 7.30-7.16 (m, 3H), 7.19-7.16 (m, 3H), 7.02 (d, J=8.7 Hz, 1H), 6.85 (d, J=1.2 Hz, 1H), 4.14 (t, J=6.3 Hz, 2H), 2.70-2.60 (m, 2H), 2.01-1.50 (series of m, 6H).

Example 12

Intermediate 6

6-(furan-3-yl)-5-((5-phenylpentyl)oxy)picolinaldehyde

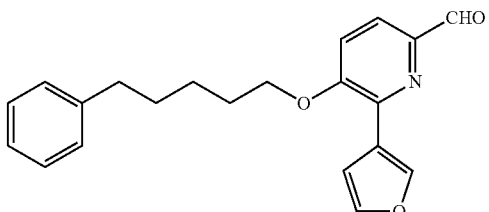

Intermediate 5 (0.335 g, 0.96 mmol) and furan-3-yl boronic acid [CAS 5552-70-0] (0.215 g, 1.92 mmol), Na₂CO₃ (2.8 mL, 2M) in DMF (12 mL) with PdCl₂(PPh₃)₂ (74 mg, ~11 mol %) at 120° C. for 20 m with MWI (microwave irradiation: Biotage Initiator 2.5). The reaction mixture was diluted with water, and extracted (2×) with 1:1 EtOAc:hexanes. The organic layers were washed (3×) with water, dried over MgSO₄, filtered and concentrated onto silica gel. Auto-column (9 hexane/1 EtOAc) gave Intermediate 6.
¹H NMR (300 MHz, CDCl₃): δ 10.0 (s, 1H), 8.21 (s, 1H), 7.84 (d, J=8.4 Hz, 1H), 7.50 (brs, 1H), 7.28-7.17 (series of m, 7H), 4.16 (t, J=6.3 Hz, 2H), 2.67 (t, J=9.0 Hz, 2H), 1.99-1.55 (series of m, 6H).

Example 13

Intermediate 8

4,4,5,5-tetramethyl-2-(44(5-phenylpentyl)oxy)-3-(thiophen-2-yl)phenyl)-1,3-dioxolane

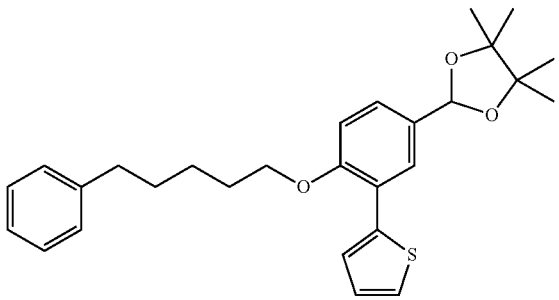 [SMILES: CC1(C)OC(c2ccc(OCCCCCc3ccccc3)c(-c3cccs3)c2)OC1(C)C]

In a 500 mL 3-necked flask equipped with a stir-bar and condenser was placed Intermediate 7 (4.9 g, 1.4 mmol), pinacol (6.6 g, 5.6 mol) and p-toluenesulfonic acid (0.8 g, 4.2 mmol) in benzene (125 mL). The resulting mixture was refluxed for 1 h. The reaction was cooled to room temperature, washed with saturated NaHCO₃ (2×75 mL), brine (1×75 mL), filtered through 1PS filter paper and concentrated under reduced pressure to give a brown oil. The oil was chromatographed over silica gel (100 g) with anhydrous sodium sulfate (20 g) on top packed with hexane. The column was eluted with 12×50 mL of 15% EtOAc in hexane. The product was eluted to give 5.1 g (81%) as a yellow oil.
¹H NMR (CDCl₃) δ 7.8 (s, 1H), 7.55 (d, 1H), 7.1-7.4 (m, 8H), 6.95 (d, 1H), 6.0 (s, 1H), 4.1 (t, 2H), 2.7 (t, 2H), 1.95 (m, 2H), 1.7 (m, 2H), 1.6 (m, 2H), 1.35 (d, 12H).

Example 14

Intermediate 9

2-(3-(5-fluorothiophen-2-yl)-4-((5-phenylpentyl)oxy)phenyl)-4,4,5,5-tetramethyl-1,3-dioxolane

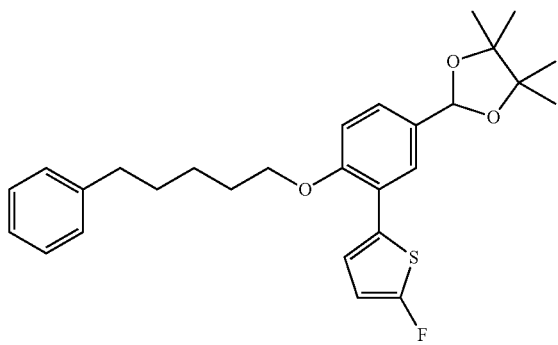 [SMILES: CC1(C)OC(c2ccc(OCCCCCc3ccccc3)c(-c3ccc(F)s3)c2)OC1(C)C]

In a 500 mL 3-necked flask equipped with a stir-bar, dropping funnel, and thermometer was placed Intermediate 8 (4.95 g, 1.1 mmol) in THF (100 mL) under argon. The resulting solution was cooled to −78° C. n-BuLi (8.8 mL, 2.2 mmol of 2.5 M in hexane) was added over 30 min. The mixture was stirred for 90 m and then N-fluorobenzenesulfonimide (7.5 g, 2.4 mmol) was added as powder in one portion. To the reaction mixture was added saturated ammonium chloride (75 mL), water (25 mL) and ethyl acetate (100 mL) after stirring for 90 m at −78° C. The reaction mixture was warmed to room temperature. The organic layer was separated, washed with brine (1×75 mL), filtered through 1PS filter paper and concentrated under reduced pressure to give 11.5 g of a green residue. The residue was triturated with 10% EtOAc in hexane (50 mL). The insoluble material was filtered and filtrate concentrated under reduced pressure to give 6.5 g of a green residue. The residue was flash chromatographed repeatedly over silica gel with anhydrous sodium sulfate on top; the columns were eluted with either EtOAc:hexanes and/or hexanes:CH$_2$Cl$_2$ to give 2.9 g (57%) of Intermediate 9 as colorless oil.

$^1$H NMR (CDCl$_3$) δ 7.75 (s, 1H), 7.2-7.4 (m, 6H), 7.15 (t, 1H), 6.95 (d, 1H), 6.45 (t, 1H), 6.0 (s, 1H), 4.15 (t, 2H), 2.7 (t, 2H), 1.95 (m, 2H), 1.75 (m, 2H), 1.6 (m, 2H), 1.35 (d, 12H).

Example 15

Intermediate 10

3-(5-fluorothiophen-2-yl)-4-((5-phenylpentyl)oxy)benzaldehyde

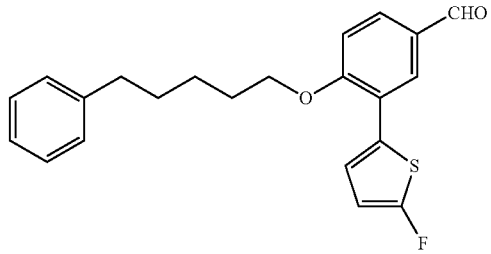 [SMILES: O=Cc1ccc(OCCCCCc2ccccc2)c(-c2ccc(F)s2)c1]

A solution of Intermediate 9 (2.01 g, 4.3 mmol) in tetrahydrofuran (50 mL) and 3 M HCl (50 mL) was stirred at rt, overnight. To the reaction mixture was diluted with ethyl acetate (50 mL) and water (50 mL). The organic layer was separated, washed with brine (1×50 mL), filtered through 1PS filter paper and concentrated under reduced pressure to give 1.6 g of an oil. The oil was dissolved in boiling hexane (20 mL) and after standing for 2 h, a white crystalline solid was collected; and dried under vacuum to give 1.15 g (73%) of Intermediate 10

$^{19}$F NMR showed a quartet at −131.201, −131.209, −131.215 and −131.223

Example 16

Intermediate 54

1-(4-((5-phenylpentyl)oxy)-3-(thiophen-2-yl)phenyl)ethanol

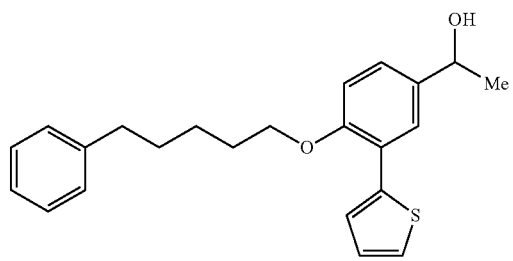 [SMILES: CC(O)c1ccc(OCCCCCc2ccccc2)c(-c2cccs2)c1]

A solution of Intermediate 7 (1.4 g, 4.0 mmol) in THF (40 mL) was reacted with methyl magnesium bromide (4.7 mL, 3.0 M in diethyl ether) at −78° C. for 40 m. The mixture was quenched with methanol and solvent removed under vacuum. The residue was poured onto ammonium chloride (sat) and the organic material was extracted with ethyl acetate. The combined layers were dried over MgSO$_4$, filtered and concentrated onto silica gel. Auto column with hexane:ethyl acetate gave 1-(4-((5-phenylpentyl)oxy)-3-(thiophen-2-yl)phenyl)ethanol Intermediate 54 1.0 g (68%).

Example 17

Intermediate 55

1-(4-((5-phenylpentyl)oxy)-3-(thiophen-2-yl)phenyl)ethanone

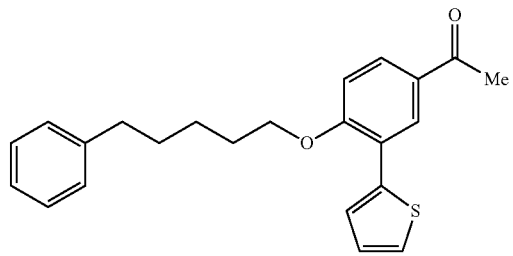 [SMILES: CC(=O)c1ccc(OCCCCCc2ccccc2)c(-c2cccs2)c1]

A mixture of Intermediate 54 (1.0 g, 2.73 mmol) and MnO$_2$ (85%, 16.4 mmol) in dioxane (10 mL) was heated to 100° C. for 2.5 h. The mixture was filtered, and washed with ethyl acetate. The solution was concentrated onto silica gel and purified by auto-column with hexane:ethyl acetate to give a white solid 0.85 g (85%).

(300 MHz, CDCl$_3$) δ: 7.65 (d, J=2.1 Hz, 1H), 7.50 (d, J=1.2 Hz, 1H), 7.30-7.19 (ser of m, 7H), 7.09-7.07 (m, 1H), 7.94-

6.91 (m, 1H), 4.90-4.95 (m, 1H), 4.07 (t, J=6.6 Hz, 2H), 2.64 (t, J=6.6 Hz, 2H), 2.04 (s, 2H), 2.95-1.55 (ser of m, 6H), 1.51 (d, J=6.6 Hz, 3H).

Example 18

Intermediate 56

3-(2-Bromoacetyl)-4-((5-phenylpentyl)oxy)benzaldehyde

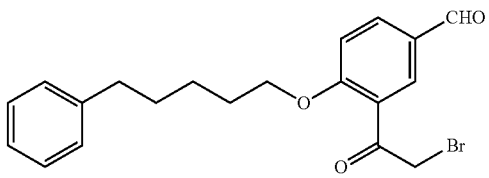 [SMILES: O=Cc1ccc(OCCCCCc2ccccc2)c(C(=O)CBr)c1]

Intermediate 53 (0.50 g, 1.48 mmol) in THF (5 mL) and water (1 mL) was treated with NBS [128-08-5] (0.30 g, 1.68 mmol) at rt for 10 m. The solvent was removed, the mixture was diluted with water and extracted with hexanes:ethyl acetate (1:1, 200 mL). The organic mixture was dried over $MgSO_4$, filtered and concentrated onto silica gel. Auto-column with ethyl acetate gave Intermediate 56 as a pure oil 0.59 g (~99%).

Example 19

Intermediate 57

3-(Oxazol-4-yl)-4-((5-phenylpentyl)oxy)benzaldehyde

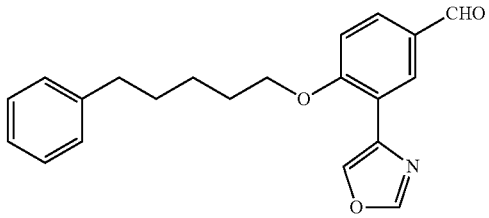 [SMILES: O=Cc1ccc(OCCCCCc2ccccc2)c(-c2cocn2)c1]

Intermediate 56 (0.59 g, 1.52 mmol) in formamide (4 mL) was heated under microwave irradiation 100° C. for 5 m. The mixture was treated to an aqueous work-up and purification by auto-column with ethyl acetate:hexanes gave 0.06 g of Intermediate 57

(300 MHz, $CDCl_3$) δ: 9.99 (s, 1H), 8.66 (d, J=2.4 Hz, 1H), 8.16 (d, J=1.0 Hz, 1H), 7.96 (d, J=1.0 Hz, 1H), 7.86 (dd, J=8.4, 2.1 Hz, 1H), 7.31-7.05 (m, 6H), 4.21 (t, J=6.3 Hz, 2H), 2.67 (t, J=7.8 Hz, 2H), 2.04-1.52 (ser. of m, 6H).

Example 20

Intermediate 58

4-((5-phenylpentyl)oxy)-3-(1H-pyrazol-1-yl)benzaldehyde

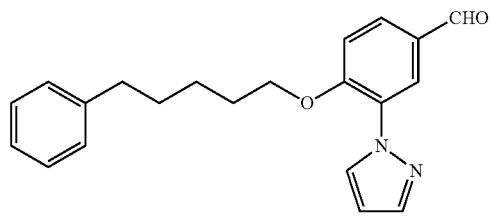 [SMILES: O=Cc1ccc(OCCCCCc2ccccc2)c(-n2cccn2)c1]

A mixture of Intermediate 1 (1.0 g, 2.88 mmol), CuI (0.56 g, 2.94 mmol), potassium carbonate (1.20 g, 8.68 mmol), 1H-pyrazole [288-13-1] (0.44 g, 6.33 mmol) N,N'-dimethyl-1,2-ethanediamine [110-70-3] (0.15 mL, 1.39 mmol) was heated at 160° C. for ~18 h. The mixture was cooled to rt, diluted with hexane:ethyl acetate (200 mL 1:1), washed with water (3×) dried over $MgSO_4$, filtered and concentrated onto silica gel. Auto-column with ethyl acetate:hexanes gave Intermediate 58, 0.42 g (44%).

(300 MHz, $CDCl_3$) δ: 9.94 (s, 1H), 8.31 (d, J=2.1 Hz, 1H), 8.05 (d, J=14.4 Hz, 1H), 7.82 (dd, J=8.4, 1.8 Hz, 1H), 7.72 (d, J=1.2 Hz, 1H), 7.30-7.11 (m, 6H), 6.42 (dd, J=2.11, 2.7 Hz, 1H), 4.14 (t, J=6.3 Hz, 2H), 2.63 (t, J=7.8 Hz, 2H), 1.89-1.46 (series of m, 6H).

Intermediate 59 was prepared from the corresponding benzaldehyde in a similar manner to the procedure described in Example 20 for Intermediate 58. The reagents used and the results are described below in Table 3.

TABLE 3

| Interm. No. | IUPAC name Structure | Starting materials | $^1$H NMR δ (ppm) for Intermediate |
|---|---|---|---|
| 59 | 4-((5-phenylpentyl)oxy)-3-(1H-pyrrol-1-yl)benzaldehyde | Intermediate 1 pyrrole | (300 MHz, $CDCl_3$) δ: 9.91 (s, 1H), 7.82 (d, J = 2.1 Hz, 1H), 7.77 (dd, J = 8.4, 2.1 Hz, 1H), 7.30-7.09 (series of m, 6H), 7.01 (t, J = 2.4 Hz, 2H), 6.31 (t, J = 2.4 Hz, 2H), 4.10 (t, J = 6.6 Hz, 2H), 2.62 (t, J = 7.5 Hz, 2H), 1.89-1.44 (ser of m, 6H). |

Example 21

Compound 1

[3-({3-(2-furyl)-4-[(5-phenylpentyl)oxy]benzyl}amino)propyl]phosphonic acid

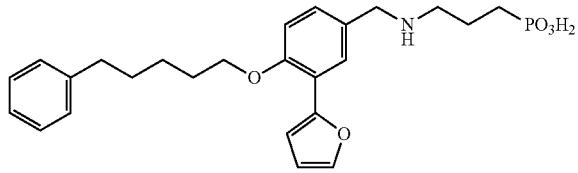

3-Aminopropylphosphonic acid [CAS 13138-33-5] (225 mg, 1.57 mmol) in MeOH (15 mL) followed by tetrabutylammonium hydroxide (TBAH) (12.8 mL, ~12.8 mmol, 1.0M in MeOH) at 50° C. for ~1 h. Intermediate 2 (440 mg, 1.31 mmol) in THF (3 mL) and MeOH (6 mL) was added, and after 30 m at 50° C. the mixture was cooled to rt. Sodium borohydride (120 mg, 3.17 mmol) was added and the reaction was continued until complete (1-2 h). [Alternative procedure: use of tetrabutylammonium hydroxide (3 eqv.) following with sodium borohydride (1.5 eqv.) at rt for ~16-18 h.] The solvent was removed under vacuum and water was added, followed by HCl (2M) until pH 2-4. The aqueous layer was extracted (two times) with chloroform: isopropanol (~3:1). The organic layers were dried over $MgSO_4$, filtered and concentrated onto amine-silica gel (ISCO). Auto-column (amine-silica gel column) (70% MeOH, 29.5% $CH_2Cl_2$, 0.5 AcOH) gave the title compound as a white solid. 310 mg, (52%)

$^1$H NMR (600 MHz, $CF_3CO_2D$): δ 7.83-7.82 (m, 1H), 7.38-7.30 (m, 2H), 7.20-7.17 (m, 3H), 7.13 (d, J=7.8 Hz, 2H), 7.08 (t, J=6.6 Hz, 1H), 7.00 (dd, J=2.4, 8.4 Hz, 1H), 6.41 (d, J=3.0 Hz, 1H), 4.30 (s, 2H), 4.14-4.11 (m, 2H), 3.40 (brs, 2H), 2.62 (t, J=7.8 Hz, 2H), 2.24-2.19 (m, 2H), 2.14-2.09 (m, 2H), 1.95-1.90 (m, 2H), 1.73-1.69 (m, 2H), 1.57-1.55 (m, 2H).

Compounds 2 through 51 were prepared from the corresponding benzaldehyde and 3-aminopropylphosphonic acid (or appropriate amine, see starting material) in a similar manner to the procedure described in Example 21 for Compound 1. The reagents used and the results are described below in Table 4.

Note: for Compounds 2 through 13, and 14 through 17, the benzaldehyde was prepared according to similar procedures as described above with reagents listed as Starting Material below in Table 4.

TABLE 4

| Comp No. | IUPAC name | Starting materials | $^1$H NMR δ (ppm) for Compound |
|---|---|---|---|
| 2 | [3-({3-(1,3-oxazol-2-yl)-4-[(5-phenylpentyl)oxy]benzyl}amino)propyl]phosphonic acid | Intermediate 1 2-(tributylstannyl)oxazole [CAS 145214-05-07] | (600 MHz, $CF_3CO_2D$): δ 8.10 (d, J = 1.8 Hz, 1H), 7.94 (d, J = 1.8 Hz, 1H), 7.72 (d, J = 9.0 Hz, 1H), 7.47 (d, J = 1.8 Hz, 1H), 7.16 (d, J = 9.0 Hz, 1H), 7.01-6.98 (m, 2H), 6.93-6.90 (m, 3H), 4.26-4.24 (m, 4H), 3.30 (brs, 2H), 2.44 (t, J = 7.2 Hz, 2H), 2.11-2.07 (m, 2H), 1.98-1.94 (m, 2H), 1.81-1.76 (m, 2H), 1.56-1.51 (m, 2H), 1.31-1.27 (m, 2H). |
| 3 | [3-({4-[(5-phenylpentyl)oxy]-3-(1,3-thiazol-2-yl)benzyl}amino)propyl]phosphonic acid | Intermediate 1 2-(tributylstannyl)thiazole [CAS 121359-48-6] | (600 MHz, $CF_3CO_2D$): δ 8.38 (brs, 1H), 8.19 (q, J = 1.8 Hz, 1H), 8.01-7.99 (m, 2H), 7.51 (dd, J = 1.8, 9.0 Hz, 1H), 7.41-7.38 (m, 2H), 7.34 (d, J = 7.8 Hz, 2H), 7.32-7.29 (m, 1H), 4.62 (brs, 2H), 4.58 (t, J = 6.0 Hz, 2H), 3.67 (brs, 2H), 2.86 (t, J = 6.61 Hz, 2H), 2.50-2.46 (m, 2H), 2.38-2.33 (m, 2H), 2.23-2.19 (m, 2H), 1.99-1.94 (m, 2H), 1.79-1.74 (m, 2H). |
| 4 | [3-({3-(3-furyl)-4-[(5-phenylpentyl)oxy]benzyl}amino)propyl]phosphonic acid | Intermediate 3 | (600 MHz, $CF_3CO_2D$): δ 7.66 (d, J = 1.8 Hz, 1H), 7.56-7.50 (m, 2H), 7.40-7.35 (m, 3H), 7.30 (d, J = 7.8 Hz, 2H), 7.25 (t, J = 7.2 Hz, 1H), 7.20 (d, J = 8.4 Hz, 1H), 6.85-6.83 (m, 1H), 4.47 (brs, 2H), 4.28 (t, J = 6.6 Hz, 2H), 3.56 (brs, 2H), 2.79 (t, J = 7.2 Hz, 1H), 2.42-2.36 (m, 2H), 2.31-2.25 (m, 2H), 2.09-2.05 (m, 2H), 1.88-1.84 (m, 2H), 1.71-1.68 (m, 2H). |

TABLE 4-continued

| Comp No. | IUPAC name | Starting materials | $^1$H NMR δ (ppm) for Compound |
|---|---|---|---|
| 5 | [3-({4-[(5-phenylpentyl)oxy]-3-(3-thienyl)benzyl}amino)propyl] phosphonic acid | Intermediate 1 thiophen-3-yl boronic acid [CAS 5552-70-0] | (600 MHz, CF$_3$CO$_2$D): δ 7.58 (d, J = 1.8 Hz, 1H), 7.45 (brs, 2H), 7.39 (dd, J = 1.8, 8.4 Hz, 1H), 7.36 (s, 1H), 7.31 (t, J = 7.2 Hz, 2H), 7.23 (d, J = 8.4 Hz, 2H), 7.19 (d, J = 8.4 Hz, 2H), 4.41 (t, J = 5.4 Hz, 2H), 4.20 (t, J = 6.0 HZ, 2H), 3.54-3.48 (m, 2H), 2.70 (t, J = 7.2 Hz, 2H), 2.35-2.30 (m, 2H), 2.25-2.20 (m, 2H), 1.94-1.91 (m, 2H), 1.77-1.74 (m, 2H), 1.58-1.55 (m, 2H). |
| 6 | [3-({4-[(5-phenylpentyl)oxy]-3-(2-thienyl)benzyl}amino)propyl] phosphonic acid | Intermediate 7 | (300 MHz, CD$_3$OD): δ 7.83 (s, 1H), 7.59-7.56 (m, 1H), 7.40-7.35 (m, 2H), 7.26-7.20 (m, 2H), 7.17-7.05 (m, 5H), 4.14-4.10 (m, 4H), 3.10 (t, J = 6.6 Hz, 2H), 2.63 (t, J = 7.8 Hz, 2H), 2.06-1.88 (m, 4H), 1.76-1.56 (m, 6H). |
| 7 | [3-({4-[3-(4-isobutylphenyl)propoxy]-3-(2-thienyl)benzyl}amino)propyl] phosphonic acid | 4-(2-methylpropyl)-benzene-propanol] [147598-21-8] 3-bromo-4-hydroxy-benzaldehyde [CAS 2973-78-6] thiophen-2-yl boronic acid [13331-23-2] | (300 MHz, CD$_3$OD): δ 7.84 (d, J = 1.8 Hz, 1H), 7.64 (dd, J = 0.9, 3.6 Hz, 1H), 7.43 (d, J = 4.8 Hz, 1H), 7.35 (dd, J = 2.1, 8.4 Hz, 1H), 7.11-7.00 (m, 6H), 4.07-4.00 (m, 4H), 3.03 (t, J = 6.3 Hz, 2H), 2.81 (t, J = 7.8 Hz, 2H), 2.41 (d, J = 6.9 Hz, 2H), 2.18-2.10 (m, 2H), 2.10-2.19 (m, 2H), 1.85-1.75 (m, 1H), 1.71-1.61 (m, 2H), 0.87 (d, J = 6.6 Hz, 6H). |
| 8 | [3-({3-cyclopent-1-en-1-yl-4-[(5-phenylpentyl)oxy]benzyl}amino) propyl]phosphonic acid | Intermediate 1 cyclopentyl boronic acid [850036-28-1] | MS (M + H)$^+$ 457.35 |
| 9 | 2-({4-[(5-phenylpentyl)oxy]-3-(2-thienyl)benzyl}amino)ethyl dihydrogen phosphate | Intermediate 7 2-aminoethyl dihydrogen phosphate [1071-23-4] | (600 MHz, CF$_3$COOD): δ 7.70 (d, J = 2.4 Hz, 1H), 7.41 (brs, 2H), 7.33 (dd, J = 1.8, 8.4 Hz, 1H), 7.22-7.20 (m, 2H), 7.15 (d, J = 7.2 Hz, 2H), 7.12-7.09 (m, 2H), 7.03 (s, 1H), 4.51-4.48 (m, 2H), 4.40 (d, J = 4.2 Hz, 2H), 4.16 (t, J = 6.6 Hz, 2H), 3.58-3.52 (m, 2H), 2.63 (t, J = 7.8 Hz, 2H), 1.95-1.92 (m, 2H), 1.712-1.58 (m, 2H), 1.59-1.55 (m, 2H). |

TABLE 4-continued

| Comp No. | IUPAC name | Starting materials | $^1$H NMR δ (ppm) for Compound |
|---|---|---|---|
| 10 | 3-({4-[(5-phenylpentyl)oxy]-3-(2-thienyl)benzyl}amino)propane-1-sulfonic acid | Intermediate 7 3-aminopropane-1-sulfonic acid [3687-18-1] | (600 MHz, CF$_3$COOD): δ 7.65 (brs, 1H), 7.36 (brs, 2H), 7.25 (d, J = 7.8 Hz, 1H), 7.20-7.18 (m, 2H), 7.13-7.12 (m, 2H), 7.10-7.05 (m, 2H), 7.01 (s, 1H), 4.30 (t, J = 5.4 Hz, 2H), 4.13 (t, J = 6.6 Hz, 2H), 3.52-3.50 (m, 2H), 3.42 (t, J = 6.6 Hz, 2H), 2.61 (t, J = 7.8 Hz, 2H), 2.46-2.40 (m, 2H), 1.84-1.89 (m, 2H), 1.72-1.67 (m, 2H), 1.58-1.53 (m, 2H). |
| 11 | methyl[3-({4-[(5-phenylpentyl)oxy]-3-(2-thienyl)benzyl}amino)propyl] phosphonic acid | Intermediate 7 (3-aminopropyl) (methyl) phosphonic acid [127729-35-5] | (600 MHz, CF$_3$COOD): δ 7.67 (d, J = 2.4 Hz, 1H), 7.45 (brs, 2H), 7.28 (dd, J = 2.4, 8.4 Hz, 1H), 7.23-7.21 (m, 2H), 7.16-7.15 (m, 2H), 7.13-7.08 (m, 2H), 7.04 (s, 1H), 4.26-4.33 (m, 2H), 4.17 (t, J = 6.0 Hz, 2H), 3.46-3.39 (m, 2H), 2.64 (t, J = 7.2 Hz, 2H), 3.00-2.24 (m, 2H), 2.13-2.08 (m, 2H), 1.97-1.92 (m, 2H), 1.75-1.69 (m, 5H), 1.61-1.56 (m, 2H). |
| 12 | 2-({4-[(5-phenylpentyl)oxy]-3-(2-thienyl)benzyl}amino)propan-1-ol | Intermediate 7 2-aminopropan-1-ol [6168-72-5] | (600 MHz, CDCl$_3$): δ 7.60 (d, J = 1.8 Hz, 1H), 7.50 (dd, J = 1.2, 4.2 Hz, 1H), 7.31 (dd, J = 1.2, 5.4 Hz, 1H), 7.27 (t, J = 7.8 Hz, 2H), 7.20-7.17 (m, 4H), 7.07 (dd, J = 3.6, 4.8 Hz, 1H), 6.91 (d, J = 8.4 Hz, 1H), 4.06 (t, J = 6.6 Hz, 2H), 3.86 (d, J = 12.6 Hz, 1H), 3.72 (d, J = 12.6 Hz, 1H), 3.63-3.61 (m, 1H), 3.49 (s, 2H), 3.31-3.28 (m, 1H), 2.89-2.86 (m, 1H), 2.65 (t, J = 7.8 Hz, 2H), 1.94-1.89 (m, 2H), 1.74-1.69 (m, 2H), 1.60-1.55 (m, 2H), 1.11 (d, J = 6.6 Hz, 3H). |
| 13 | 2-({4-[(5-phenylpentyl)oxy]-3-(2-thienyl)benzyl}amino)propane-1,3-diol | Intermediate 7 2-aminopropane-1,3-diol [534-03-2] | (600 MHz, CDCl$_3$): δ 7.62 (d, J = 2.1 Hz, 1H), 7.51 (dd, J = 1.2, 3.6 Hz, 1H), 7.31 (dd, J = 1.2, 5.4 Hz, 1H), 7.28-7.25 (m, 2H), 7.22-7.17 (m, 4H), 7.07 (dd, J = 3.6, 5.1 Hz, 1H), 6.91 (d, J = 8.1 Hz, 1H), 4.06 (t, J = 6.3 Hz, 2H), 3.84 (s, 2H), 3.78-3.73 (m, 2H), 3.65-3.60 (m, 2H), 2.88-2.83 (m, 1H), 2.65 (t, J = 7.2 Hz, 2H), 2.19 (brs, 3H), 1.96-1.87 (m, 2H), 1.75-1.66 (m, 2H), 1.62-1.54 (m, 2H). |

TABLE 4-continued

| Comp No. | IUPAC name | Starting materials | $^1$H NMR δ (ppm) for Compound |
|---|---|---|---|
| 14 | {3-[({6-(3-furyl)-5-[(5-phenylpentyl)oxy]pyridin-2-yl}methyl)amino]propyl}phosphonic acid | Intermediate 6 | (600 MHz, CF$_3$CO$_2$D): δ 8.57 (s, 1H), 8.60-8.30 (m, 2H), 7.73 (s, 1H), 7.30 (t, J = 7.2 Hz, 2H), 7.21-7.18 (m, 2H), 4.95 (s, 2H), 4.46 (t, J = 6.0 Hz, 2H), 3.68 (t, J = 6.6 Hz, 2H), 2.75 (t, J = 7.8 Hz, 2H), 2.45-2.40 (m, 2H), 2.31-2.27 (m, 2H), 2.15-2.12 (m, 2H), 1.87-1.84 (m, 2H), 1.69-1.65 (m, 2H). |
| 15 | {3-[({5-[(5-phenylpentyl)oxy]-6-(2-thienyl)pyridin-2-yl}methyl)amino]propyl}phosphonic acid | Intermediate 5 tributyl(thiophen-2-yl)stannane [54663-78-4] | (600 MHz, CF$_3$CO$_2$D): δ 8.29 (d, J = 3.6 Hz, 1H), 8.14-8.09 (m, 3H), 7.50 (t, J = 4.81 Hz, 1H), 7.42-7.38 (m, 2H), 7.35-7.30 (m, 3H), 5.06 (s, 2H), 4.57 (t, J = 6.0 Hz, 2H), 3.79 (t, 6.6 Hz, 2H), 2.86 t(, J = 6.6 Hz, 2H), 2.55-2.50 (m, 2H), 2.41-2.36 (m, 2H), 2.55-2.23 (m, 2H), 1.98-1.94 (m, 2H), 1.70-1.60 (m, 2H). |
| 16 | (3-{[4-(nonyloxy)-3-(2-thienyl)benzyl]amino}propyl)phosphonic acid | 3-bromo-4-hydroxybenzaldehyde [2973-78-6] 1-bromononane [693-58-3] tributyl(thiophen-2-yl)stannane [54663-78-4] | (600 MHz, CF$_3$CO$_2$D): δ 7.68 (s, 1H), 7.51-7.38 (m, 2H), 7.29 (d, J = 3.9 Hz, 1H), 7.13 (dd, J = 1.2, 8.4 Hz, 1H), 7.07 (d, J = 1.8 Hz, 1H), 4.35 (s, 2H), 4.20-4.18 (m, 2H), 3.44 (s, 2H), 2.30-2.22 (m, 2H), 2.20-2.10 (m, 2H), 1.93 (t, J = 6.0 Hz, 2H), 1.56-1.53 (m, 2H), 1.40-1.29 (m, 10H), 0.87-0.85 (m, 3H). |
| 17 | (3-{[4-(decyloxy)-3-(2-thienyl)benzyl]amino}propyl)phosphonic acid | 3-bromo-4-hydroxybenzaldehyde [2973-78-6] 1-bromodecane [112-29-8] tributyl(thiophen-2-yl)stannane [54663-78-4] | (600 MHz, CF$_3$CO$_2$D): δ 7.74 (s, 1H), 7.35 (d, J = 8.4 Hz, 1H), 7.19 (d, J = 8.4 Hz, 1H), 7.13 (s, 1H), 4.40 (s, 2H), 4.25 (t, J = 6.6 Hz, 2H), 3.49 (t, J = 6.6 Hz, 2H), 2.35-2.29 (m, 2H), 2.23-2.18 (m, 2H), 2.01-1.97 (m, 2H), 1.62-1.58 (m, 2H), 1.47-1.34 (m, 2H), 0.92 (t, J = 7.2 Hz, 3H). |
| 18 | 3-({3-(5-fluoro-2-thienyl)-4-[(5-phenylpentyl)oxy]benzyl}amino)propyl]phosphonic acid | Intermediate 10 | (600 MHz, CF$_3$CO$_2$D): δ 7.57 (d, J = 1.8 Hz, 1H), 7.23-7.18 (m, 3H), 7.14 (d, J = 6.6 Hz, 2H), 7.08 (t, J = 7.2 Hz, 1H), 7.03-7.01 (m, 2H), 6.38-6.37 (m, 1H), 4.30 (t, J = 5.4 Hz, 2H), 4.13 (t, J = 6.6 Hz, 2H), 3.44-3.36 (m, 2H), 2.63 (t, J = 7.8 Hz, 2H), 2.25-2.22 (m, 2H), 2.15-2.10 (m, 2H), 1.95-1.92 (m, 2H), 1.74-1.68 (m, 2H), 1.58-1.55 (m, 2H). |

| Comp No. | IUPAC name | Starting materials | $^1$H NMR δ (ppm) for Compound |
|---|---|---|---|
| 19 | (3-{[4-{[5-(3-methoxyphenyl)pentyl]oxy}-3-(2-thienyl)benzyl]amino}propyl) phosphonic acid | Intermediate 29 | (600 MHz, $CF_3CO_2D$) δ: 7.63 (s, 1 H), 7.34 (br. s., 2 H), 7.27-7.21 (m, 1 H), 7.17 (d, J = 3.8 Hz, 1 H), 7.05 (dd, J = 3.2, 8.2 Hz, 1 H), 6.99 (d, J = 3.8 Hz, 1 H), 6.89-6.85 (m, 1 H), 6.82 (br. s., 1 H), 6.79 (d, J = 7.3 Hz, 1 H), 4.30 (br. s., 2 H), 4.14 (t, J = 1.0 Hz, 2 H), 3.90 (s, 3 H), 3.40 (br. s., 2 H), 2.62 (t, J = 1.0 Hz, 2 H), 2.28-2.17 (m, 2 H), 2.15-2.04 (m, 2 H), 1.96-1.86 (m, 2 H), 1.73-1.65 (m, 2 H), 1.60-1.51 (m, 2 H). |
| 20 | (3-{[4-{[5-(4-methoxyphenyl)pentyl]oxy}-3-(2-thienyl)benzyl]amino}propyl) phosphonic acid | Intermediate 36 | (600 MHz, $CF_3CO_2D$) δ: 7.68 (s, 1 H), 7.39 (br. s., 2 H), 7.29 (d, J = 8.2 Hz, 1 H), 7.14 (d, J = 8.2 Hz, 2 H), 7.10 (d, J = 8.8 Hz, 1 H), 7.05 (s, 1 H), 6.92 (d, J = 8.5 Hz, 2 H), 4.35 (br. s., 2 H), 4.18 (t, J = 6.0 Hz, 2 H), 3.96 (s, 3 H), 3.45 (br. s., 2 H), 2.63 (t, J = 7.3 Hz, 2 H), 2.31-2.23 (m, 2 H), 2.20-2.11 (m, 2 H), 1.98-1.91 (m, 2 H), 1.75-1.68 (m, 2 H), 1.62-1.54 (m, 2 H). |
| 21 | (3-{[4-{[5-(4-fluorophenyl)pentyl]oxy}-3-(2-thienyl)benzyl]amino}propyl) phosphonic acid | Intermediate 28 | (600 MHz, $CF_3CO_2D$) δ: 7.69 (s, 1 H), 7.40 (br. s., 2 H), 7.30 (d, J = 8.5 Hz, 1 H), 7.13-7.09 (m, 3 H), 7.07 (s, 1 H), 6.88 (t, J = 8.7 Hz, 2 H), 4.37 (t, J = 5.1 Hz, 2 H), 4.19 (t, J = 6.3 Hz, 2 H), 3.46 (d, J = 6.7 Hz, 2 H), 2.64 (t, J = 7.3 Hz, 2 H), 2.35-2.25 (m, 2 H), 2.25-2.11 (m, 2 H), 2.01-1.90 (m, 2 H), 1.78-1.67 (m, 2 H), 1.64-1.54 (m, 2 H). |
| 22 | (3-{[3-(2-furyl)-4-({5-[3-(trifluoromethyl)phenyl]pentyl}oxy) benzyl]amino}propyl)phosphonic acid | Intermediate 37 | (600 MHz, $CF_3CO_2D$) δ: 7.83 (s, 1 H), 7.41-7.27 (m, 6 H), 7.20 (d, J = 8.5 Hz, 1 H), 7.01 (d, J = 8.5 Hz, 1 H), 6.41 (s, 1 H), 4.32 (br. s., 2 H), 4.14 (t, J = 6.3 Hz, 2 H), 3.41 (br. s, 2 H), 2.70 (t, J = 7.6 Hz, 2 H), 2.29-2.18 (m, 2 H), 2.17-2.07 (m, 2 H), 1.99-1.91 (m, 2 H), 1.79-1.71 (m, 2 H), 1.62-1.54 (m, 2 H). |

TABLE 4-continued

| Comp No. | IUPAC name | Starting materials | $^1$H NMR δ (ppm) for Compound |
|---|---|---|---|
| 23 | (3-{[3-(2-furyl)-4-{[5-(3-methoxyphenyl)pentyl]oxy}benzyl]amino}propyl)phosphonic acid | Intermediate 30 | (600 MHz, CF$_3$CO$_2$D) δ: 7.84 (d, J = 2.3 Hz, 1 H), 7.34 (br. s., 2 H), 7.23-7.16 (m, 2 H), 7.01 (d, J = 1.0 Hz, 1 H), 6.89 (d, J = 7.3 Hz, 1 H), 6.85-6.82 (m, 1 H), 6.79 (d, J = 1.2 Hz, 1 H), 6.41 (s, 1 H), 4.32 (br. s., 2 H), 4.14 (t, J = 6.3 Hz, 2 H), 3.92 (s, 3 H), 3.41 (d, J = 6.2 Hz, 2 H), 2.67-2.62 (m, 2 H), 2.29-2.20 (m, 2 H), 2.16-2.07 (m, 2 H), 1.98-1.91 (m, 2 H), 1.77-1.69 (m, 2 H), 1.62-1.54 (m, 2 H). |
| 24 | (3-{[4-{[5-(4-fluorophenyl)pentyl]oxy}-3-(2-furyl)benzyl]amino}propyl)phosphonic acid | Intermediate 31 | (600 MHz, CF$_3$CO$_2$D) δ: 7.82 (d, J = 2.3 Hz, 1 H), 7.32 (br. s., 2 H), 7.18 (dd, J = 2.3, 8.5 Hz, 1 H), 7.09-7.02 (m, 2 H), 6.99 (d, J = 1.0 Hz, 1 H), 6.81 (t, J = 9.0 Hz, 2 H), 6.40 (s, 1 H), 4.33-4.26 (m, 2 H), 4.11 (t, J = 6.3 Hz, 2 H), 3.43-3.35 (m, 2 H), 2.59 (t, J = 7.5 Hz, 2 H), 2.27-2.19 (m, 2 H), 2.15-2.05 (m, 2 H), 1.95-1.87 (m, 2 H), 1.73-1.63 (m, 2 H), 1.57-1.50 (m, 2 H). |
| 25 | [3-({4-[4-(4-fluorophenyl)butoxy]-3-(2-thienyl)benzyl}amino)propyl]phosphonic acid | Intermediate 38 | (600 MHz, CF$_3$CO$_2$D) δ: 7.63 (s, 1 H), 7.34 (br. s, 2 H), 7.23 (d, J = 8.5 Hz, 1 H), 7.06 (dd, J = 5.9, 7.9 Hz, 2 H), 7.04-7.00 (m, 2 H), 6.83 (t, J = 8.8 Hz, 2 H), 4.30 (br. s., 2 H), 4.13 (t, J = 6.0 Hz, 2 H), 3.39 (br. s, 2 H), 2.62 (t, J = 7.3 Hz, 2 H), 2.28-2.17 (m, 2 H), 2.16-2.04 (m, 2 H), 1.92-1.86 (m, 2 H), 1.86-1.79 (m, 2 H). |
| 26 | [3-({4-[4-(4-fluorophenyl)butoxy]-3-(2-furyl)benzyl}amino)propyl]phosphonic acid | Intermediate 39 | (600 MHz, CF$_3$CO$_2$D) δ: 7.82 (s, 1 H), 7.33 (d, J = 8.2 Hz, 2 H), 7.18 (d, J = 8.5 Hz, 1 H), 7.12-7.04 (m, 2 H), 6.97 (d, J = 8.5 Hz, 1 H), 6.84 (t, J = 8.8 Hz, 2 H), 6.42 (s, 1 H), 4.30 (br. s, 2 H), 4.12 (t, J = 6.2 Hz, 2 H), 3.39 (s, 2 H), 2.65 (t, J = 7.2 Hz, 2 H), 2.28-2.17 (m, 2 H), 2.16-2.05 (m, 2 H), 1.95-1.88 (m, 2 H), 1.87-1.80 (m, 2 H). |

TABLE 4-continued

| Comp No. | IUPAC name | Starting materials | $^1$H NMR δ (ppm) for Compound |
|---|---|---|---|
| 27 | (3-{[4-{[5-(3-fluoro-4-methoxyphenyl)pentyl]oxy}-3-(2-furyl)benzyl]amino}propyl)phosphonic acid | Intermediate 42 | (600 MHz, CF$_3$CO$_2$D) δ: 7.64 (s, 1 H), 7.34 (br. s., 2 H), 7.25 (d, J = 8.2 Hz, 1 H), 7.06 (d, J = 8.5 Hz, 1 H), 7.02 (s, 1 H), 6.97-6.92 (m, 1 H), 6.91-6.84 (m, 2 H), 4.32 (br. s., 2 H), 4.15 (t, J = 6.3 Hz, 2 H), 3.95 (s, 3 H), 3.46-3.37 (m, 2 H), 2.59 (t, J = 7.3 Hz, 2 H), 2.29-2.19 (m, 2 H), 2.16-2.07 (m, 2 H), 1.95-1.87 (m, 2 H), 1.68 (quin, J = 7.4 Hz, 2 H), 1.59-1.50 (m, 2 H). |
| 28 | (3-{[4-{[5-(3-fluoro-4-methoxyphenyl)pentyl]oxy}-3-(2-thienyl)benzyl]amino}propyl)phosphonic acid | Intermediate 34 | (600 MHz, CF$_3$CO$_2$D) δ: 7.64 (s, 1 H), 7.34 (br. s., 2 H), 7.25 (d, J = 8.2 Hz, 1 H), 7.06 (d, J = 8.5 Hz, 1 H), 7.02 (s, 1 H), 6.97-6.91 (m, 1 H), 6.90-6.85 (m, 2 H), 4.32 (br. s., 2 H), 4.15 (t, J = 6.3 Hz, 2 H), 3.95 (s, 3 H), 3.46-3.36 (m, 2 H), 2.59 (t, J = 7.3 Hz, 2 H), 2.29-2.20 (m, 2 H), 2.16-2.06 (m, 2 H), 1.95-1.88 (m, 2 H), 1.68 (quin, J = 7.4 Hz, 2 H), 1.59-1.50 (m, 2 H). |
| 29 | (3-{[4-{[5-(4-chlorophenyl)pentyl]oxy}-3-(2-furyl)benzyl]amino}propyl)phosphonic acid | Intermediate 32 | (600 MHz, CF$_3$CO$_2$D) δ: 7.82 (s, 1 H), 7.33 (br. s., 2 H), 7.19 (d, J = 8.2 Hz, 1 H), 7.11 (d, J = 8.2 Hz, 2 H), 7.03 (d, J = 7.9 Hz, 2 H), 6.99 (d, J = 8.5 Hz, 1 H), 6.41 (s, 1 H), 4.30 (s, 2 H), 4.12 (s, 2 H), 3.40 (s, 2 H), 2.65-2.55 (m, 2 H), 2.29-2.20 (m, 2 H), 2.16-2.06 (m, 2 H), 1.95-1.87 (m, 2 H), 1.75-1.64 (m, 2 H), 1.58-1.49 (m, 2 H). |
| 30 | (3-{[4-{[5-(4-chlorophenyl)pentyl]oxy}-3-(2-thienyl)benzyl]amino}propyl)phosphonic acid | Intermediate 43 | (600 MHz, CF$_3$CO$_2$D) δ: 7.64 (d, J = 2.1 Hz, 1 H), 7.34 (br. s., 2 H), 7.28-7.22 (m, 1 H), 7.11 (d, J = 8.5 Hz, 2 H), 7.07-6.99 (m, 4 H), 4.32 (br. s., 2 H), 4.13 (t, J = 6.0 Hz, 2 H), 3.41 (br. s., 2 H), 2.61-2.56 (m, 2 H), 2.28-2.20 (m, 2 H), 2.16-2.06 (m, 2 H), 1.93-1.86 (m, 2 H), 1.72-1.63 (m, 2 H), 1.57-1.49 (m, 2 H). |

TABLE 4-continued

| Comp No. | IUPAC name | Starting materials | ¹H NMR δ (ppm) for Compound |
|---|---|---|---|
| 31 | (3-{[4-{[5-(3-chloro-4-methoxyphenyl)pentyl]oxy}-3-(2-furyl)benzyl]amino}propyl)phosphonic acid | Intermediate 33 | (600 MHz, CF$_3$CO$_2$D) δ: 7.83 (d, J = 2.3 Hz, 1 H), 7.34 (br. s., 2 H), 7.20 (dd, J = 2.3, 8.5 Hz, 1 H), 7.16 (d, J = 1.8 Hz, 1 H), 7.05-6.99 (m, 2 H), 6.95 (d, J = 8.2 Hz, 1 H), 6.42 (s, 1 H), 4.31 (br. s., 2 H), 4.14 (t, J = 6.2 Hz, 2 H), 3.93 (s, 3 H), 3.42 (br. s., 2 H), 2.59 (t, J = 7.3 Hz, 2 H), 2.31-2.20 (m, 2 H), 2.18-2.08 (m, 2 H), 1.98-1.89 (m, 2 H), 1.75-1.66 (m, 2 H), 1.56 (s, 2 H). |
| 32 | (3-{[4-{[5-(3-chloro-4-methoxyphenyl)pentyl]oxy}-3-(2-thienyl)benzyl]amino}propyl)phosphonic acid | Intermediate 35 | (600 MHz, CF$_3$CO$_2$D) δ: 7.64 (s, 1 H), 7.35 (br. s., 2 H), 7.25 (d, J = 8.5 Hz, 1 H), 7.16 (s, 1 H), 7.07-6.99 (m, 3 H), 6.94 (d, J = 8.5 Hz, 1 H), 4.31 (br. s., 2 H), 4.14 (t, J = 6.2 Hz, 2 H), 3.93 (s, 3 H), 3.41 (br. s., 2 H), 2.58 (t, J = 7.3 Hz, 2 H), 2.27-2.19 (m, 2 H), 2.16-2.06 (m, 2 H), 1.95-1.88 (m, 2 H), 1.72-1.64 (m, 2 H), 1.59-1.51 (m, 2 H). |
| 33 | (3-{[3-(2-furyl)-4-{[5-(4-methoxyphenyl)pentyl]oxy}benzyl]amino}propyl)phosphonic acid | Intermediate 40 | (600 MHz, CF$_3$CO$_2$D) δ: 7.82 (s, 1 H), 7.32 (br. s., 2 H), 7.19 (d, J = 8.5 Hz, 1 H), 7.10 (d, J = 8.5 Hz, 2 H), 7.00 (d, J = 8.5 Hz, 1 H), 6.88 (d, J = 8.5 Hz, 2 H), 6.40 (s, 1 H), 4.30 (t, J = 5.6 Hz, 2 H), 4.13 (t, J = 6.3 Hz, 2 H), 3.91 (s, 3 H), 3.41 (br. s., 2 H), 2.60 (t, J = 7.2 Hz, 2 H), 2.28-2.18 (m, 2 H), 2.16-2.06 (m, 2 H), 1.97-1.89 (m, 2 H), 1.73-1.65 (m, 2 H), 1.59-1.51 (m, 2 H). |
| 34 | (3-{[3-(3-furyl)-4-{[5-(3-methoxyphenyl)pentyl]oxy}benzyl]amino}propyl)phosphonic acid | Intermediate 41 | (600 MHz, CF$_3$CO$_2$D) δ: 7.84 (d, J = 2.3 Hz, 1 H), 7.34 (br. s., 2 H), 7.23-7.16 (m, 2 H), 7.01 (d, J = 1.0 Hz, 1 H), 6.89 (d, J = 7.3 Hz, 1 H), 6.85-6.82 (m, 1 H), 6.79 (d, J = 1.2 Hz, 1 H), 6.41 (s, 1 H), 4.32 (br. s., 2 H), 4.14 (t, J = 6.3 Hz, 2 H), 3.92 (s, 3 H), 3.41 (d, J = 6.2 Hz, 2 H), 2.67-2.62 (m, 2 H), 2.29-2.20 (m, 2 H), 2.16-2.07 (m, 2 H), 1.98-1.91 (m, 2 H), 1.77-1.69 (m, 2 H), 1.62-1.54 (m, 2 H). |

TABLE 4-continued

| Comp No. | IUPAC name | Starting materials | $^1$H NMR δ (ppm) for Compound |
|---|---|---|---|
| 35 | [3-({3-(1,3-oxazol-4-yl)-4-[(5-phenylpentyl)oxy]benzyl}amino)propyl] phosphonic acid | Intermediate 57 | (600 MHz, CF$_3$CO$_2$D) δ: 9.41 (d, J = 3.6 Hz, 1H), 8.40 (d, J = 4.2 Hz, 1H), 7.81 (s, 1H), 7.61 (d, J = 9.0 Hz, 1H), 7.21-7.16 (m, 3H), 7.16-7.11 (m, 3H), 4.37 (s, 2H), 4.22 (t, J = 6.0 Hz, 2H), 3.45 (bs, 2H), 2.63 (t, J = 7.8 Hz, 2H), 2.32-2.22 (m, 2H), 2.17-2.11 (m, 2H), 1.97-1.90 (m, 2H), 1.73-1.70 (m, 2H), 1.54-1.45 (m, 2H). |
| 36 | [3-({3-(2-furyl)-4-[(5-phenylpentyl)oxy]benzyl}amino)-1-methylpropyl] phosphonic acid | Intermediate 2 (4-aminobutan-2-yl) phosphonic acid [79782-59-5] | (600 MHz, CD$_3$OD) δ: 7.92 (s, 1H), 7.53 (s, 1H), 7.35 (d, J = 6.6 Hz, 1H), 7.24-7.21 (m, 2H), 7.16-7.11 (m, 3H), 7.05 (d, J = 8.4 Hz, 1H), 6.92 (d, J = 3.6 Hz, 1H), 6.49 (dd, J = 3.6, 1.8 Hz, 1H), 4.16-4.06 (m, 4H), 3.16 (br s, 1H), 3.05 (br s, 1H), 2.63 (t, J = 7.2 Hz, 2H), 1.92-1.83 (m, 4H), 1.73-1.68 (m, 3H), 1.57-1.52 (m, 2H), 1.18-1.15 (m, 3H). |
| 37 | [3-({4-[(5-phenylpentyl)oxy]-3-(2-thienyl)benzyl}amino)propyl] phosphonic acid | Intermediate 7 | (600 MHz, CD$_3$OD—CDCl$_3$) δ: 7.74 (d, J = 2.4 Hz, 1H), 7.53 (dd, J = 3.6, 0.6 Hz, 1H), P—H 7.03 (d, J = 504.6 Hz, 1H), 7.32 (dd, J = 5.4, 1.2 Hz, 1H), 7.27 (dd, J = 8.4, 2.4 Hz, 1H), 7.21 (t, J = 7.2 Hz, 2H), 7.13-7.10 (m, 3H), 7.04 (dd, J = 4.8, 3.6 Hz, 1H), 6.99 (dd, J = 8.4 Hz, 1H), 4.06 (t, J = 6.6 Hz, 2H), 3.99 (s, 2H), 2.95 (t, J = 6.0 Hz, 2H), 2.60 (t, J = 7.2 Hz, 2H), 1.92-1.86 (m, 4H), 1.70-1.65 (m, 2H), 1.60-1.53 (m, 4H). |
| 38 | [3-({3-(5-fluoro-2-furyl)-4-[(5-phenylpentyl)oxy]benzyl}amino) propyl]phosphonic acid | Intermediate 45 | (600 MHz, CD$_3$OD—CDCl$_3$) δ: 7.73 (d, J = 1.8 Hz, 1H), 7.32 (dd, J = 8.4, 1.8 Hz, 1H), 7.26 (t, J = 7.8 Hz, 2H), 7.18-7.15 (m, 3H), 7.03 (d, J = 8.4 Hz, 1H), 6.83 (t, J = 3.0 Hz, 1H), 5.55 (dd, J = 6.6, 3.0 Hz, 1H), 4.12 (t, J = 6.6 Hz, 2H), 4.07 (s, 1H), 3.05 (t, J = 5.4 Hz, 2H), 2.67 (t, J = 7.2 Hz, 2H), 1.99-1.92 (m, 4H), 1.76-1.69 (m, 4H), 1.59-1.55 (m, 2H). |

TABLE 4-continued

| Comp No. | IUPAC name | Starting materials | $^1$H NMR δ (ppm) for Compound |
|---|---|---|---|
| 39 | (3-{[4-{[5-(3-chlorophenyl)pentyl]oxy}-3-(2-furyl)benzyl]amino}propyl) phosphonic acid | Intermediate 46 | (600 MHz, DMSO-d$_6$-CF$_3$CO$_2$D) δ: 7.96 (d, J = 2.4 Hz, 1H), 7.73 (dd, J = 1.8, 0.9 Hz, 1H), 7.37 (dd, J = 8.4, 2.4 Hz, 1H), 7.31-7.26 (m, 2H), 7.24-7.14 (m, 3H), 6.93 (dd, J = 3.3, 0.6 Hz, 1H), 6.58 (dd, J = 3.3, 1.8 Hz, 1H), 4.18-4.12 (m, 4H), 3.05 (t, J = 7.2 Hz, 2H), 2.64 (t, J = 7.5 Hz, 2H), 1.94-1.86 (m, 4H), 1.79-1.64 (m, 4H), 1.56-1.48 (m, 2H). |
| 40 | (3-{[3-(2-furyl)-4-{[5-(3-methylphenyl)pentyl]oxy}benzyl]amino} propyl)phosphonic acid | Intermediate 51 | (600 MHz, DMSO-d$_6$-CF$_3$CO$_2$D—CDCl$_3$) δ: 7.89-7.88 (m, 2H), 7.69-7.68 (m, 1H), 7.33-7.29 (m, 1H), 7.13-7.08 (m, 2H), 6.96-6.88 (m, 4H), 6.54-6.53 (m, 1H), 4.11-4.07 (m, 4H), 3.01-2.96 (m, 2H), 2.54 (t, J = 7.5 Hz, 2H), 2.23 (s, 3H), 1.88-1.80 (m, 4H), 1.69-1.58 (m, 4H), 1.52-1.44 (m, 2H). |
| 41 | [1,1-difluoro-3-({3-(5-fluoro-2-furyl)-4-[(5-phenylpentyl)oxy]benzyl} amino)propyl]phosphonic acid | Intermediate 45 Intermediate 26 | (600 MHz, DMSO-d$_6$) δ: 7.68 (d, J = 2.4 Hz, 1H), 7.33 (dd, J = 9.0, 2.4 Hz, 1H), 7.25-7.22 (m, 2H), 7.17-7.11 (m, 4H), 6.78 (t, J = 3.6 Hz, 1H), 5.85 (dd, J =7.2, 3.6 Hz, 1H), 4.09 (t, J = 6.0 Hz, 2H), 4.01 (s, 2H), 2.99 (t, J = 5.4 Hz, 2H), 2.58 (t, J = 7.8 Hz, 2H), 2.06-2.04 (m, 2H), 1.84-1.80 (m, 2H), 1.65-1.62 (m, 2H), 1.46-1.44 (m, 2H). |
| 42 | {3-[(1-{4-[(5-phenylpentyl)oxy]-3-(2-thienyl)phenyl}ethyl)amino]propyl} phosphonic acid | Intermediate 55 | (600 MHz, CD$_3$OD—CDCl$_3$) δ: 7.75 (d, J = 2.4 Hz, 1H), 7.58 (d, J = 2.4 Hz, 1H), 7.38 (d, J = 5.4 Hz, 1H), 7.32 (dd, J = 8.4, 2.4 Hz, 1H), 7.32 (dd, J = 8.4, 2.4 Hz, 1H), 7.25 (t, J = 7.2 Hz, 2H), 7.18-7.14 (m, 3H), 7.10-7.08 (m, 2H), 4.24 (q, J = 7.2 Hz, 1H), 4.14 (t, J = 6.6 Hz, 2H), 2.96-2.93 (m, 1H), 2.85-2.82 (m, 1H), 2.66 (t, J = 7.2 Hz, 2H), 1.97-1.92 (m, 4H), 1.76-1.59 (m, 9H). |
| 43 | [3-({4-[(5-phenylpentyl)oxy]-3-(1H-pyrazol-1-yl)benzyl}amino) propyl]phosphonic acid | Intermediate 58 | (600 MHz, CF$_3$CO$_2$D) δ: 8.08 (d, J = 2.4 Hz, 1H), 8.02 (d, J = 9.0 Hz, 1H), 7.70 (s, 1H), 7.30-7.26 (m, 3H), 7.20 (t, J = 7.2 Hz, 1H), 7.16 (d, J = 7.2 Hz, 2H), 6.81 (t, J = 3.0 Hz, 1H), 4.44 (brs, 2H), 4.18-4.16 (m, 2H), 3.51 (brs, 2H), 2.63-2.61 (m, 2H), 2.33-2.17 (m, 4H), 1.82-1.79 (m, 2H), 1.65-1.62 (m, 2H), 1.39-1.37 (m, 2H). |

TABLE 4-continued

| Comp No. | IUPAC name | Starting materials | $^1$H NMR δ (ppm) for Compound |
|---|---|---|---|
| 44 | [3-({4-[(5-phenylpentyl)oxy]-3-(1H-pyrrol-1-yl)benzyl}amino)propyl] phosphonic acid | Intermediate 59 | (600 MHz, CF$_3$CO$_2$D) δ: 7.81 (brs, 1H), 7.75 (d, J = 7.8 Hz, 1H), 7.72 (s, 1H), 7.32-7.29 (m, 3H), 7.23-7.19 (m, 3H), 6.88 (brs, 1H), 4.44 (d, J = 3.0 hz, 2H), 4.25 (t, J = 6.0 Hz, 2H), 3.53 (d, J = 4.2 Hz, 2H), 2.68 (t, J = 7.2 Hz, 2H), 2.38-2.30 (m, 2H), 2.24-2.16 (m, 2H), 1.92-1.90 (m, 2H), 1.75-1.70 (m, 2H), 1.50-1.46 (m, 2H). |
| 45 | [3-({3-(2-furyl)-4-[(5-phenylpentyl)oxy]benzyl}amino)propyl]phosphonic acid-d_2_ | Intermediate 27 | (600 MHz, CF$_3$CO$_2$D) δ: 7.87 (s, 1H), 7.42-7.36 (m, 2H), 7.25-7.22 (m, 3H), 7.18 (d, J = 7.2 Hz, 2H), 7.13 (t, J = 7.2 Hz, 2H), 7.05 (d, J = 8.4 Hz, 1H), 6.46 (s, 1H), 4.35 (t, J = 5.4 Hz, 2H), 3.46-3.43 (m, 2H), 2.67 (t, J = 7.8 Hz, 2H), 2.30-2.24 (m, 2H), 2.23-2.13 (m, 2H), 1.98-1.95 (m, 2H), 1.78-.174 (m, 2H), 1.62-1.58 (m, 2H). |
| 46 | [3-({3-(2-furyl)-4-[(5-phenylpentyl)amino]benzyl}amino)propyl] phosphonic acid | Intermediate 47 | (300 MHz, DMSO-d$_6$-CF$_3$CO$_2$D) δ: 8.00 (dd. J = 1.8, 0.6 Hz, 1H), 7.96-7.93 (m, 1H), 7.58 (d, J = 8.1 Hz, 1H), 7.50-7.45 (m, 2H), 7.40-7.34 (m, 3H), 7.30-7.24 (m, 1H), 7.07-7.04 (m, 1H), 6.87 (dd, J = 3.0, 1.5 Hz, 1H), 4.32 (s, 2H), 3.44 (t, J = 7.2 Hz, 2H), 3.25 (t, J = 6.9 Hz, 2H), 2.80 (t, J = 7.8 Hz, 2H), 2.18-2.04 (m, 2H), 1.99-1.79 (m, 6H), 1.68-1.58 (m, 2H). |
| 47 | [3-({3-(1,3-oxazol-2-yl)-4-[(5-phenylpentyl)amino]benzyl}amino) propyl]phosphonic acid | Intermediate 48 | (300 MHz, DMSO-d$_6$-CF$_3$CO$_2$D) δ: 8.15 (d, J = 0.9 Hz, 1H), 7.97 (d, J = 2.1 Hz, 1H), 7.39-7.36 (m, 2H), 7.25-7.20 (m, 2H), 7.17-7.10 (m, 3H), 6.83 (d, J = 9.0 Hz, 1H), 4.05 (s, 2H), 3.25 (t, J = 7.2 Hz, 2H), 2.99 (t, J = 7.5 Hz, 2H), 2.57 (t, J = 7.5 Hz, 2H), 1.90-1.80 (m, 2H), 1.72-1.62 (m, 6H), 1.46-1.38 (m, 2H). |

TABLE 4-continued

| Comp No. | IUPAC name | Starting materials | $^1$H NMR δ (ppm) for Compound |
|---|---|---|---|
| 48 | [3-({4-[(5-phenylpentyl)amino]-3-(1,3-thiazol-2-yl)benzyl}amino)propyl] phosphonic acid | Intermediate 49 | (300 MHz, DMSO-d$_6$-CF$_3$CO$_2$D) δ: 7.85 (d, J = 3.6 Hz, 1H), 7.81 (d, J = 2.1 Hz, 1H), 7.68 (d, J = 3.3 Hz, 1H), 7.34 (dd, J = 8.7, 1.8 Hz, 1H), 7.26-7.20 (m, 2H), 7.17-7.10 (m, 3H), 6.84 (d, J = 8.7 Hz, 1H), 4.06 (s, 2H), 3.24 (t, J = 7.2 Hz, 2H), 3.01 (t, J = 7.2 Hz, 2H), 2.57 (t, J = 7.5 Hz, 2H), 1.90-1.81 (m, 2H), 1.73-1.57 (m, 6H), 1.46-1.38 (m, 2H). |
| 49 | (3-{[4-{[5-(2-fluorophenyl)pentyl]oxy}-3-(2-furyl)benzyl]amino} propyl)phosphonic acid | Intermediate 63 | (600 MHz, TFA) δ: 7.91 (d, J = 2.1 Hz, 1 H), 7.70 (d, J = 1.8 Hz, 1 H), 7.33 (d, J = 8.5 Hz, 1 H), 7.27-7.22 (m, 1 H), 7.21-7.16 (m, 1 H), 7.13 (d, J = 8.5 Hz, 1 H), 7.09-7.03 (m, 2 H), 6.90 (d, J = 3.2 Hz, 1 H), 6.55 (dd, J = 1.8, 3.2 Hz, 1 H), 4.14-4.08 (m, 4 H), 3.05-2.96 (m, 2 H), 2.63 (t, J = 7.8 Hz, 2 H), 1.91-1.80 (m, 4 H), 1.73-1.61 (m, 4 H), 1.55-1.44 (m, 2 H). |
| 50 | (3-{[4-{[5-(2-fluorophenyl)pentyl]oxy}-3-(3-furyl)benzyl]amino}propyl) phosphonic acid | Intermediate 64 | (600 MHz, DMSO-d$_6$, few drops of TFA) δ: 8.05 (br. s., 1 H), 7.72 (d, J = 2.3 Hz, 1 H), 7.70-7.68 (m, 1 H), 7.32 (dd, J = 2.1, 8.2 Hz, 1 H), 7.27-7.23 (m, 1 H), 7.21-7.17 (m, 1 H), 7.12-7.04 (m, 3 H), 6.93-6.91 (m, 1 H), 4.11-4.07 (m, 4 H), 3.04-2.99 (m, 2 H), 2.65-2.60 (m, 2 H), 1.90-1.82 (m, 4 H), 1.73-1.61 (m, 4 H), 1.51-1.44 (m, 2 H). |
| 51 | [3-({2-fluoro-5-(2-furyl)-4-[(5-phenylpentyl)oxy]benzyl}amino)propyl] phosphonic acid | Intermediate 66 | (600 MHz, DMSO-d$_6$, few drops of TFA) δ: 7.97 (d, J = 9.0 Hz, 1H), 7.71 (dd, J = 1.2, 1.8 Hz, 1H), 7.24 (td, J = 7.8, 1.8 Hz, 2H), 7.17 (dd, J = 1.2, 7.8 Hz, 2H), 7.15-7.12 (m, 1H), 7.09 (d, J = 12 Hz, 1H), 6.84 (dd, J = 0.6, 3.6 Hz, 1H), 6.55 (dd, J = 1.8, 3.6 Hz, 1H), 4.17 (s, 2H), 4.12 (t, J = 6.0 Hz, 2H), 3.04 (t, J = 7.8 Hz, 2H), 2.60 (t, J = 7.2 Hz, 3H), 1.88-1.83 (m, 4H), 1.70-1.64 (m, 4H), 1.50-1.46 (m, 2H). |

Compounds 52 through 118 are prepared according to similar procedures described above. The compounds are tabulated below in Table 5.

TABLE 5

| Comp. No. | Compound name<br>Structure |
|---|---|
| 52 | (3-((4-((3-(3-bromo-4-isopropoxyphenyl)propyl)amino)-3-(furan-3-yl)benzyl)amino)propyl)phosphonic acid |
| 53 | (3-((4-((3-(3-chloro-4-isobutylphenyl)propyl)amino)-3-(furan-3-yl)benzyl)amino)propyl)phosphonic acid |
| 54 | (3-((4-((3-(3-chloro-4-isopropoxyphenyl)propyl)amino)-3-(furan-3-yl)benzyl)amino)propyl)phosphonic acid |
| 55 | (3-((2-fluoro-4-((5-(4-fluorophenyl)pentyl)oxy)-5-(furan-2-yl)benzyl)amino)propyl)phosphonic acid |
| 56 | (3-((2-fluoro-4-((5-(2-fluorophenyl)pentyl)oxy)-5-(furan-2-yl)benzyl)amino)propyl)phosphonic acid |

TABLE 5-continued

| Comp. No. | Compound name / Structure |
|---|---|
| 57 | (3-((2-fluoro-4-((5-(4-fluorophenyl)pentyl)oxy)-5-(furan-3-yl)benzyl)amino)propyl)phosphonic acid 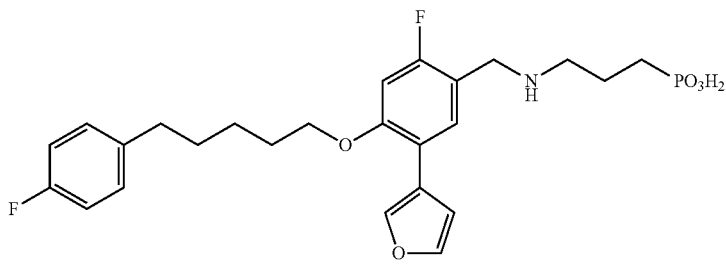 |
| 58 | (3-((2-fluoro-4-((5-(2-fluorophenyl)pentyl)oxy)-5-(furan-3-yl)benzyl)amino)propyl)phosphonic acid 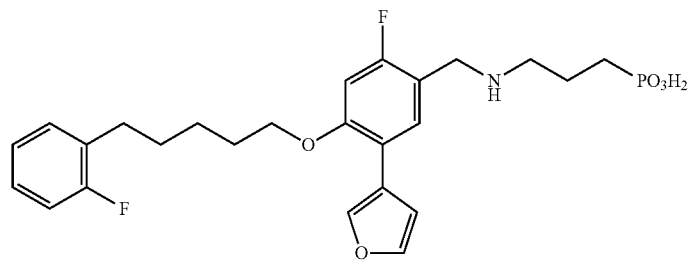 |
| 59 | (3-((2-fluoro-4-((5-(4-fluorophenyl)pentyl)amino)-5-(furan-2-yl)benzyl)amino)propyl)phosphonic acid 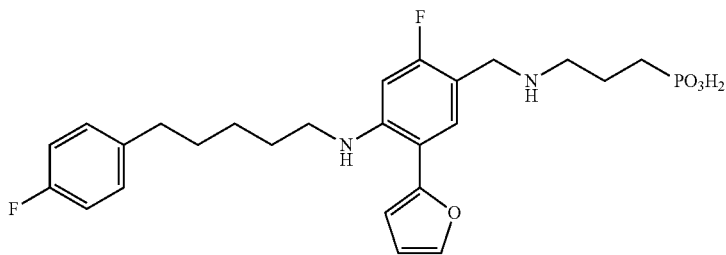 |
| 60 | (3-((2-fluoro-4-((5-(2-fluorophenyl)pentyl)amino)-5-(furan-2-yl)benzyl)amino)propyl)phosphonic acid 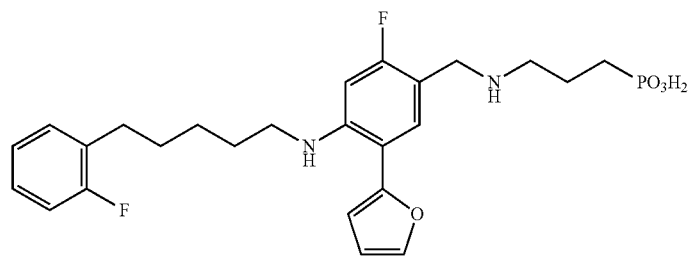 |

TABLE 5-continued

| Comp. No. | Compound name<br>Structure |
|---|---|
| 61 | (3-((2-fluoro-4-((5-(4-fluorophenyl)pentyl)amino)-5-(furan-3-yl)benzyl)amino)propyl)phosphonic acid |
| 62 | (3-((2-fluoro-4-((5-(2-fluorophenyl)pentyl)amino)-5-(furan-3-yl)benzyl)amino)propyl)phosphonic acid |
| 63 | (3-((3-(furan-2-yl)-4-(3-(4-isobutylphenyl)propoxy)benzyl)amino)propyl)phosphonic acid |
| 64 | (3-((3-(furan-2-yl)-4-(3-(4-isobutyl-3-(trifluoromethyl)phenyl)propoxy)benzyl)amino)propyl)phosphonic acid |
| 65 | (3-((4-(3-(4-isobutyl-3-(trifluoromethyl)phenyl)propoxy)-3-(thiophen-2-yl)benzyl)amino)propyl)phosphonic acid |

TABLE 5-continued

| Comp. No. | Compound name<br>Structure |
|---|---|
| 66 | (3-((4-(3-(4-isopropoxy-3-(trifluoromethyl)phenyl)propoxy)-3-(thiophen-2-yl)benzyl)amino)propyl)phosphonic acid |
| 67 | (3-((4-(3-(3-bromo-4-isobutylphenyl)propoxy)-3-(furan-2-yl)benzyl)amino)propyl)phosphonic acid |
| 68 | (3-((4-(3-(3-bromo-4-isopropoxyphenyl)propoxy)-3-(furan-2-yl)benzyl)amino)propyl)phosphonic acid |
| 69 | (3-((4-(3-(3-bromo-4-isobutylphenyl)propoxy)-3-(thiophen-2-yl)benzyl)amino)propyl)phosphonic acid |
| 70 | (3-((4-(3-(3-bromo-4-isopropoxyphenyl)propoxy)-3-(thiophen-2-yl)benzyl)amino)propyl)phosphonic acid |

TABLE 5-continued

| Comp. No. | Compound name / Structure |
|---|---|
| 71 | (3-((4-(3-chloro-4-isobutylphenyl)propoxy)-3-(furan-2-yl)benzyl)amino)propyl)phosphonic acid |
| 72 | (3-((4-(3-(3-chloro-4-isopropoxyphenyl)propoxy)-3-(furan-2-yl)benzyl)amino)propyl)phosphonic acid |
| 73 | (3-((4-(3-(3-chloro-4-isobutylphenyl)propoxy)-3-(thiophen-2-yl)benzyl)amino)propyl)phosphonic acid |
| 74 | (3-((4-(3-(3-chloro-4-isopropoxyphenyl)propoxy)-3-(thiophen-2-yl)benzyl)amino)propyl)phosphonic acid |
| 75 | (3-((4-(3-(3-fluoro-4-isobutylphenyl)propoxy)-3-(furan-2-yl)benzyl)amino)propyl)phosphonic acid |

TABLE 5-continued

| Comp. No. | Compound name Structure |
|---|---|
| 76 | (3-((4-(3-(3-fluoro-4-isopropoxyphenyl)propoxy)-3-(furan-2-yl)benzyl)amino)propyl)phosphonic acid |
| 77 | (3-((4-(3-(3-fluoro-4-isobutylphenyl)propoxy)-3-(thiophen-2-yl)benzyl)amino)propyl)phosphonic acid |
| 78 | (3-((4-(3-(3-fluoro-4-isopropoxyphenyl)propoxy)-3-(thiophen-2-yl)benzyl)amino)propyl)phosphonic acid |
| 79 | (3-((4-(3-(3-cyano-4-isobutylphenyl)propoxy)-3-(furan-2-yl)benzyl)amino)propyl)phosphonic acid |
| 80 | (3-((4-(3-(3-cyano-4-isopropoxyphenyl)propoxy)-3-(furan-2-yl)benzyl)amino)propyl)phosphonic acid |

TABLE 5-continued

| Comp. No. | Compound name Structure |
|---|---|
| 81 | (3-((4-(3-(3-cyano-4-isobutylphenyl)propoxy)-3-(thiophen-2-yl)benzyl)amino)propyl)phosphonic acid |
| 82 | (3-((4-(3-(3-cyano-4-isopropoxyphenyl)propoxy)-3-(thiophen-2-yl)benzyl)amino)propyl)phosphonic acid |
| 83 | (3-((3-(furan-3-yl)-4-(3-(4-isobutyl-3-(trifluoromethyl)phenyl)propoxy)benzyl)amino)propyl)phosphonic acid |
| 84 | (3-((3-(furan-3-yl)-4-(3-(4-isopropoxy-3-(trifluoromethyl)phenyl)propoxy)benzyl)amino)propyl)phosphonic acid |
| 85 | (3-((4-(3-(3-bromo-4-isobutylphenyl)propoxy)-3-(furan-3-yl)benzyl)amino)propyl)phosphonic acid |

TABLE 5-continued

| Comp. No. | Compound name / Structure |
|---|---|
| 86 | (3-((4-(3-(3-bromo-4-isopropoxyphenyl)propoxy)-3-(furan-3-yl)benzyl)amino)propyl)phosphonic acid |
| 87 | (3-((4-(3-(3-chloro-4-isobutylphenyl)propoxy)-3-(furan-3-yl)benzyl)amino)propyl)phosphonic acid |
| 88 | (3-((4-(3-(3-chloro-4-isopropoxyphenyl)propoxy)-3-(furan-3-yl)benzyl)amino)propyl)phosphonic acid |
| 89 | (3-((4-(3-(3-fluoro-4-isobutylphenyl)propoxy)-3-(furan-3-yl)benzyl)amino)propyl)phosphonic acid |
| 90 | (3-((4-(3-(3-fluoro-4-isopropoxyphenyl)propoxy)-3-(furan-3-yl)benzyl)amino)propyl)phosphonic acid |

TABLE 5-continued

| Comp. No. | Compound name  Structure |
|---|---|
| 91 | (3-((4-(3-(3-cyano-4-isobutylphenyl)propoxy)-3-(furan-3-yl)benzyl)amino)propyl)phosphonic acid |
| 92 | (3-((4-(3-(3-cyano-4-isopropoxyphenyl)propoxy)-3-(furan-3-yl)benzyl)amino)propyl)phosphonic acid |
| 93 | (3-((3-(furan-2-yl)-4-((3-(4-isobutylphenyl)propyl)amino)benzyl)amino)propyl)phosphonic acid |
| 94 | (3-((3-(furan-2-yl)-4-((3-(4-isopropoxyphenyl)propyl)amino)benzyl)amino)propyl)phosphonic acid |
| 95 | (3-((4-((3-(3-fluoro-4-isobutylphenyl)propyl)amino)-3-(furan-2-yl)benzyl)amino)propyl)phosphonic acid |

TABLE 5-continued

| Comp. No. | Compound name Structure |
|---|---|
| 96 | (3-((4-((3-(3-fluoro-4-isopropoxyphenyl)propyl)amino)-3-(furan-2-yl)benzyl)amino)propyl)phosphonic acid |
| 97 | (3-((4-((3-(3-cyano-4-isobutylphenyl)propyl)amino)-3-(furan-2-yl)benzyl)amino)propyl)phosphonic acid |
| 98 | (3-((4-((3-(3-cyano-4-isopropoxyphenyl)propyl)amino)-3-(furan-2-yl)benzyl)amino)propyl)phosphonic acid |
| 99 | (3-((3-(furan-2-yl)-4-((3-(4-isobutyl-3-(trifluoromethyl)phenyl)propyl)amino)benzyl)amino)propyl)phosphonic acid |
| 100 | (3-((3-(furan-2-yl)-4-((3-(4-isopropoxy-3-(trifluoromethyl)phenyl)propyl)amino)benzyl)amino)propyl)phosphonic acid |

TABLE 5-continued

| Comp. No. | Compound name<br>Structure |
|---|---|
| 101 | (3-((4-((3-(3-bromo-4-isobutylphenyl)propyl)amino)-3-(furan-2-yl)benzyl)amino)propyl)phosphonic acid |
| 102 | (3-((4-((3-(3-bromo-4-isopropoxyphenyl)propyl)amino)-3-(furan-2-yl)benzyl)amino)propyl)phosphonic acid |
| 103 | (3-((4-((3-(3-chloro-4-isobutylphenyl)propyl)amino)-3-(furan-2-yl)benzyl)amino)propyl)phosphonic acid |
| 104 | (3-((4-((3-(3-chloro-4-isopropoxyphenyl)propyl)amino)-3-(furan-2-yl)benzyl)amino)propyl)phosphonic acid |
| 105 | (3-((3-(furan-3-yl)-4-((3-(4-isobutylphenyl)propyl)amino)benzyl)amino)propyl)phosphonic acid |

TABLE 5-continued

| Comp. No. | Compound name Structure |
|---|---|
| 106 | (3-((3-furan-3-yl)-4-((3-(4-isopropoxyphenyl)propyl)amino)benzyl)amino)propyl)phosphonic acid |
| 107 | (3-((4-((3-(3-fluoro-4-isobutylphenyl)propyl)amino)-3-(furan-3-yl)benzyl)amino)propyl)phosphonic acid |
| 108 | (3-((4-((3-(3-fluoro-4-isopropoxyphenyl)propyl)amino)-3-(furan-3-yl)benzyl)amino)propyl)phosphonic acid |
| 109 | (3-((4-((3-(3-cyano-4-isobutylphenyl)propyl)amino)-3-(furan-3-yl)benzyl)amino)propyl)phosphonic acid |
| 110 | (3-((4-((3-(3-cyano-4-isopropoxyphenyl)propyl)amino)-3-(furan-3-yl)benzyl)amino)propyl)phosphonic acid |

TABLE 5-continued

| Comp. No. | Compound name<br>Structure |
|---|---|
| 111 | (3-((3-(furan-3-yl)-4-((3-(4-isobutyl-3-(trifluoromethyl)phenyl)propyl)amino)benzyl)amino)propyl)phosphonic acid |
| 112 | (3-((3-(furan-3-yl)-4-((3-(4-isopropoxy-3-(trifluoromethyl)phenyl)propyl)amino)benzyl)amino)propyl)phosphonic acid |
| 113 | (3-((4-((3-(3-bromo-4-isobutylphenyl)propyl)amino)-3-(furan-3-yl)benzyl)amino)propyl)phosphonic acid |
| 114 | (3-((3-(furan-2-yl)-4-(6-phenylhexyl)benzyl)amino)propyl)phosphonic acid |
| 115 | (3-((2-fluoro-4-(6-(4-fluorophenyl)hexyl)-5-(furan-2-yl)benzyl)amino)propyl)phosphonic acid |

TABLE 5-continued

| Comp. No. | Compound name Structure |
|---|---|
| 116 | (3-((2-fluoro-4-(6-(4-fluorophenyl)hexyl)-5-(furan-3-yl)benzyl)amino)propyl)phosphonic acid |
| 117 | (3-((2-fluoro-4-(6-(2-fluorophenyl)hexyl)-5-(furan-2-yl)benzyl)amino)propyl)phosphonic acid |
| 118 | (3-((2-fluoro-4-(6-(2-fluorophenyl)hexyl)-5-(furan-3-yl)benzyl)amino)propyl)phosphonic acid |

Biological Examples

In Vitro Assay

Compounds were tested for S1P1 activity using the GTP $\gamma^{35}$S binding assay. These compounds may be assessed for their ability to activate or block activation of the human S1P1 receptor in cells stably expressing the S1P1 receptor.

GTP $\gamma^{35}$S binding was measured in the medium containing (mM) HEPES 25, pH 7.4, MgCl$_2$ 10, NaCl 100, dithitothreitol 0.5, digitonin 0.003%, 0.2 nM GTP $\gamma^{35}$S, and 5 µg membrane protein in a volume of 150 µl. Test compounds were included in the concentration range from 0.08 to 5,000 nM unless indicated otherwise. Membranes were incubated with 100 µM 5'-adenylylimmidodiphosphate for 30 min, and subsequently with 10 µM GDP for 10 min on ice. Drug solutions and membrane were mixed, and then reactions were initiated by adding GTP $\gamma^{35}$S and continued for 30 min at 25° C. Reaction mixtures were filtered over Whatman GF/B filters under vacuum, and washed three times with 3 mL of ice-cold buffer (HEPES 25, pH7.4, MgCl$_2$ 10 and NaCl 100). Filters were dried and mixed with scintillant, and counted for $^{35}$S activity using a β-counter. Agonist-induced GTP $\gamma^{35}$S binding was obtained by subtracting that in the absence of agonist. Binding data were analyzed using a non-linear regression method. In case of antagonist assay, the reaction mixture contained 10 nM S1P in the presence of test antagonist at concentrations ranging from 0.08 to 5000 nM.

Table 6: Activity potency: S1P1 receptor from GTP $\gamma^{35}$S: nM, (EC$_{50}$)

TABLE 6

| Compound number | IUPAC name | S1P1 EC$_{50}$ (nM) |
|---|---|---|
| 1 | [3-({3-(2-furyl)-4-[(5-phenylpentyl)oxy]benzyl}amino)propyl]phosphonic acid | 0.9 |
| 2 | [3-({3-(1,3-oxazol-2-yl)-4-[(5-phenylpentyl)oxy]benzyl}amino)propyl]phosphonic acid | 11.9 |
| 3 | [3-({4-[(5-phenylpentyl)oxy]-3-(1,3-thiazol-2-yl)benzyl}amino)propyl]phosphonic acid | 2.0 |
| 4 | [3-({3-(3-furyl)-4-[(5-phenylpentyl)oxy]benzyl}amino)propyl]phosphonic acid | 0.6 |
| 5 | [3-({4-[(5-phenylpentyl)oxy]-3-(3-thienyl)benzyl}amino)propyl]phosphonic acid | 3.3 |

TABLE 6-continued

| Compound number | IUPAC name | S1P1 EC$_{50}$ (nM) |
|---|---|---|
| 6 | [3-({4-[(5-phenylpentyl)oxy]-3-(2-thienyl)benzyl}amino)propyl]phosphonic acid | 1.3 |
| 7 | [3-({4-[3-(4-isobutylphenyl)propoxy]-3-(2-thienyl)benzyl}amino)propyl]phosphonic acid | 14.9 |
| 8 | [3-({3-cyclopent-1-en-1-yl-4-[(5-phenylpentyl)oxy]benzyl}amino)propyl]phosphonic acid | 3.4 |
| 9 | 2-({4-[(5-phenylpentyl)oxy]-3-(2-thienyl)benzyl}amino)ethyl dihydrogen phosphate | 1.5 |
| 10 | 3-({4-[(5-phenylpentyl)oxy]-3-(2-thienyl)benzyl}amino)propane-1-sulfonic acid | 10.1 |
| 11 | methyl[3-({4-[(5-phenylpentyl)oxy]-3-(2-thienyl)benzyl}amino)propyl]phosphinic acid | 23 |
| 12 | 2-({4-[(5-phenylpentyl)oxy]-3-(2-thienyl)benzyl}amino)propan-1-ol | 241 |
| 13 | 2-({4-[(5-phenylpentyl)oxy]-3-(2-thienyl)benzyl}amino)propane-1,3-diol | 714 |
| 14 | {3-[({6-(3-furyl)-5-[(5-phenylpentyl)oxy]pyridin-2-yl}methyl)amino]propyl}phosphonic acid | 1.0 |
| 15 | {3-[({5-[(5-phenylpentyl)oxy]-6-(2-thienyl)pyridin-2-yl}methyl)amino]propyl}phosphonic acid | 0.77 |
| 16 | (3-{[4-(nonyloxy)-3-(2-thienyl)benzyl]amino}propyl)phosphonic acid | 517.4 |
| 17 | (3-{[4-(decyloxy)-3-(2-thienyl)benzyl]amino}propyl)phosphonic acid | 293.7 |
| 18 | 3-({3-(5-fluoro-2-thienyl)-4-[(5-phenylpentyl)oxy]benzyl}amino)propyl]phosphonic acid | 2.0 |
| 19 | (3-{[4-{[5-(3-methoxyphenyl)pentyl]oxy}-3-(2-thienyl)benzyl]amino}propyl)phosphonic acid | 1120 |
| 20 | (3-{[4-{[5-(4-methoxyphenyl)pentyl]oxy}-3-(2-thienyl)benzyl]amino}propyl)phosphonic acid | 48.6 |
| 21 | (3-{[4{[5-(4-fluorophenyl)pentyl]oxy}-3-(2-thienyl)benzyl]amino}propyl)phosphonic acid | 19.7 |
| 22 | (3-{[3-(2-furyl)-4-({5-[3-(trifluoromethyl)phenyl]pentyl}oxy)benzyl]amino}propyl)phosphonic acid | 65.7 |
| 23 | (3-{[3-(2-furyl)-4-{[5-(3-methoxyphenyl)pentyl]oxy}benzyl]amino}propyl)phosphonic acid | 240.3 |
| 24 | (3-{[4-{[5-(4-fluorophenyl)pentyl]oxy}-3-(2-furyl)benzyl]amino}propyl)phosphonic acid | 0.98 |
| 25 | [3-({4-[4-(4-fluorophenyl)butoxy]-3-(2-thienyl)benzyl}amino)propyl]phosphonic acid | 67.5 |
| 26 | [3-({4-[4-(4-fluorophenyl)butoxy]-3-(2-furyl)benzyl}amino)propyl]phosphonic acid | 98.9 |
| 27 | (3-{[4-{[5-(3-fluoro-4-methoxyphenyl)pentyl]oxy}-3-(2-furyl)benzyl]amino}propyl)phosphonic acid | 7.0 |
| 28 | (3-{[4-{[5-(3-fluoro-4-methoxyphenyl)pentyl]oxy}-3-(2-thienyl)benzyl]amino}propyl)phosphonic acid | 1.9 |
| 29 | (3-{[4-{[5-(4-chlorophenyl)pentyl]oxy}-3-(2-furyl)benzyl]amino}propyl)phosphonic acid | 5.7 |
| 30 | (3-{[4-{[5-(4-chlorophenyl)pentyl]oxy}-3-(2-thienyl)benzyl]amino}propyl)phosphonic acid | 8.0 |
| 31 | (3-{[4-{[5-(3-chloro-4-methoxyphenyl)pentyl]oxy}-3-(2-furyl)benzyl]amino}propyl)phosphonic acid | 8.4 |
| 32 | (3-{[4-{[5-(3-chloro-4-methoxyphenyl)pentyl]oxy}-3-(2-thienyl)benzyl]amino}propyl)phosphonic acid | 6.5 |
| 33 | (3-{[3-(2-furyl)-4-{[5-(4-methoxyphenyl)pentyl]oxy}benzyl]amino}propyl)phosphonic acid | 7.1 |
| 34 | (3-{[3-(3-furyl)-4-{[5-(3-methoxyphenyl)pentyl]oxy}benzyl]amino}propyl)phosphonic acid | 12.5 |
| 35 | [3-({3-(1,3-oxazol-4-yl)-4-[(5-phenylpentyl)oxy]benzyl}amino)propyl]phosphonic acid | 54.1 |
| 36 | [3-({3-(2-furyl))-4-[(5-phenylpentyl)oxy]benzyl}amino)-1-methylpropyl]phosphonic acid | 18.5 |
| 37 | [3-({4-[(5-phenylpentyl)oxy]-3-(2-thienyl)benzyl}amino)propyl]phosphinic acid | 52.6 |
| 38 | [3-({3-(5-fluoro-2-furyl)-4-[(5-phenylpentyl)oxy]benzyl}amino)propyl]phosphonic acid | 1.9 |
| 39 | (3-{[4-{[5-(3-chlorophenyl)pentyl]oxy}-3-(2-furyl)benzyl]amino}propyl)phosphonic acid | 32.8 |
| 40 | (3-{[3-(2-furyl)-4-{[5-(3-methylphenyl)pentyl]oxy}benzyl]amino}propyl)phosphonic acid | 34.9 |
| 41 | [1,1-difluoro-3-({3-(5-fluoro-2-furyl)-4-[(5-phenylpentyl)oxy]benzyl}amino)propyl]phosphonic acid | 53.6 |
| 42 | {3-[(1-{4-[(5-phenylpentyl)oxy]-3-(2-thienyl)phenyl}ethyl)amino]propyl}phosphonic acid | 16.4 |
| 43 | [3-({4-[(5-phenylpentyl)oxy]-3-(1H-pyrazol-1-yl)benzyl}amino)propyl]phosphonic acid | 8.5 |
| 44 | [3-({4-[(5-phenylpentyl)oxy]-3-(1H-pyrrol-1-yl)benzyl}amino)propyl]phosphonic acid | 3.4 |
| 45 | [3-({3-(2-furyl)-4-[(5-phenylpentyl)oxy]benzyl}amino)propyl]phosphonic acid-d_2_ | 1.7 |
| 46 | [3-({3-(2-furyl)-4-[(5-phenylpentyl)amino]benzyl}amino)propyl]phosphonic acid | 1.5 |
| 47 | [3-({3-(1,3-oxazol-2-yl)-4-[(5-phenylpentyl)amino]benzyl}amino)propyl]phosphonic acid | 15.6 |
| 48 | [3-({4-[(5-phenylpentyl)amino]-3-(1,3-thiazol-2-yl)benzyl}amino)propyl]phosphonic acid | 17.4 |
| 49 | (3-{[4-{[5-(2-fluorophenyl)pentyl]oxy}-3-(2-furyl)benzyl]amino}propyl)phosphonic acid | 1.0 |
| 50 | (3-{[4-{[5-(2-fluorophenyl)pentyl]oxy}-3-(3-furyl)benzyl]amino}propyl)phosphonic acid | <25 |
| 51 | [3-({2-fluoro-5-(2-furyl)-4-[(5-phenylpentyl)oxy]benzyl}amino)propyl]phosphonic acid | 1.0 |

In Vivo Assay: Lymphopenia Assay in Mice
Detailed Description

A lymphopenia assay in mice; as previously described, was employed to measure the in vivo blood lymphocyte depletion after dosing with the test compound: [3-({4-[(5-phenylpentyl)oxy]-3-(2-thienyl)benzyl}amino)propyl]phosphonic acid Compound 6. This S1P1 modulator, [3-({4-[(5-phenylpentyl)oxy]-3-(2-thienyl)benzyl}amino)propyl]phosphonic acid Compound 6 is useful for S1P-related diseases and exemplified by the lymphopenia in vivo response.

Test drugs, were prepared in a solution containing 3% (w/v) 2-hydroxy propyl β-cyclodextrin (HPBCD) and 1% DMSO to a final concentration of 1 mg/ml, and subcutaneously injected to female C57BL6 mice (CHARLES RIVERS) weighing 20-25 g at the dose of 10 mg/Kg. Blood samples were obtained by puncturing the submandibular skin with a Goldenrod animal lancet at different time intervals such as: 24, 48, 72 (and 96 h) post drug application. Blood was collected into microvettes (SARSTEDT) containing EDTA tripotassium salt. Lymphocytes in blood samples were counted using a HEMAVET Multispecies Hematology System, HEMAVET HV950FS (Drew Scientific Inc.). (Hale, J. et al Bioorg. & Med. Chem. Lett. 14 (2004) 3351

Results are shown in FIG. 1 that depicts lowered lymphocyte count after 24 hours (<1 number of lymphocytes $10^3/\mu L$ blood). The positive control, [3-({4-[(5-phenylpentyl)oxy]-3-(2-thienyl)benzyl}amino)propyl]phosphonic acid Compound 6 is an S1P1 modulator.

What is claimed is:

1. A method of treating an immunosuppressant disorder associated with the sphingosine-1-phosphate receptor modulation, wherein the immunosuppressant disorder is selected from: rheumatoid arthritis, psoriasis, atherosclerosis, autoimmune uveitis, dry eye, inflammatory bowel diseases, atopic allergy, atopic dermatitis, contact dermatitis, multiple sclerosis, Sjogren's syndrome and organ transplant rejection, in a mammal in need thereof, which comprises administering to a mammal in need thereof, a pharmaceutical composition comprising a therapeutically effective amount of at least one compound represented by Formula I or a pharmaceutically acceptable salt thereof:

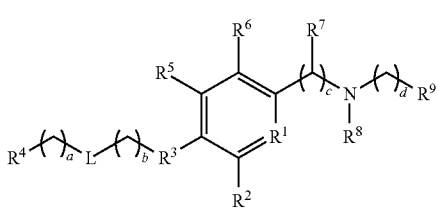

Formula I wherein:
$R^1$ is N or C—$R^{10}$;
$R^2$ is optionally substituted aromatic heterocycle, optionally substituted non-aromatic heterocycle, optionally substituted cycloalkyl, or optionally substituted cycloalkenyl;
$R^3$ is O, N—$R^{11}$, CH—$R^{12}$ or S;
$R^4$ is H or optionally substituted aryl;
$R^5$ is H, halogen, hydroxyl, —$OC_{1-3}$ alkyl, or optionally substituted $C_{1-3}$ alkyl;
$R^6$ is H, optionally substituted $C_{1-3}$ alkyl, halogen, hydroxyl or —$OC_{1-3}$ alkyl;
$R^7$ is H or optionally substituted $C_{1-6}$ alkyl;
$R^8$ is H or optionally substituted $C_{1-6}$ alkyl;
$R^9$ is —$OPO_3H_2$, —$P(O)(OH)_2$, —$S(O)_2OH$, —P(O)MeOH, —P(O)(H)OH or —$OR^{15}$;
$R^{10}$ is H, optionally substituted $C_{1-6}$ alkyl, halogen, hydroxyl or —$OC_{1-3}$ alkyl;
$R^{11}$ is H or optionally substituted $C_{1-3}$ alkyl;
$R^{12}$ is H, optionally substituted $C_{1-3}$ alkyl, halogen, hydroxyl, —$OC_{1-3}$alkyl or amino;
$R^{13}$ is H or optionally substituted $C_{1-3}$ alkyl;
$R^{14}$ is H or optionally substituted $C_{1-3}$ alkyl;
$R^{15}$ is H or optionally substituted $C_{1-3}$ alkyl;
L is $CHR^{16}$;
a is 0, 1, 2, 3, 4 or 5;
b is 0, 1, 2, 3, 4 or 5;
c is 0 or 1;
d is 0, 1, 2 or 3;
$R^{16}$ is H, optionally substituted $C_{1-3}$ alkyl, —$OC_{1-3}$ alkyl, halogen, hydroxyl or amino, and
$R^{17}$ is H or optionally substituted $C_{1-3}$ alkyl;
with the provisos:
a). when $R^9$ is —$OPO_3H_2$, —$P(O)(OH)_2$, —$S(O)_2OH$, —P(O)MeOH or —P(O)(H)OH then d is not 0; and
b). when $R^9$ is $OR^{15}$ then d is not 0 or 1.

2. The method according to claim 1, wherein said compound is represented by Formula I wherein:
$R^2$ is optionally substituted 5-member aromatic heterocycle or cycloalkenyl.

3. The method according to claim 1, wherein said compound is represented by Formula I wherein:
$R^2$ is cyclopentane, cyclopentene, pyrazolidine, pyrroline, pyrrolidine, imidazoline, pyrazoline, thiazoline, oxazoline, thiophene, dihydrothiophene, furan, dihydrofuran, pyrrole, oxazole, thiazole, thiazole, imidazole, pyrazole, isoxazole, isothiazole, tetrazole, oxadiazole, 1,2,5-oxadiazole, thiadiazole, 1,2,3-triazole, 1,2,4-triazole, imidazoline, pyrrolidinone, pyrrol-2(3H)-one, imidazolidin-2-one, or 1,2,4-triazol-5(4H)-one;
c is 1; and
d is 1, 2 or 3.

4. The method according to claim 1, wherein said compound is represented by Formula I wherein:

$R^2$ is optionally substituted 5-member aromatic heterocycle, optionally substituted non-aromatic 5-member heterocycle or cycloalkenyl;
$R^9$ is —$OPO_3H_2$, or —$OR^{15}$;
$R^{10}$ is H, $C_{1-6}$ alkyl, halogen, hydroxyl or —$OC_{1-3}$ alkyl;
$R^{11}$ is H or $C_{1-3}$ alkyl;
$R^{12}$ is H, $C_{1-3}$ alkyl, halogen, hydroxyl, —$OC_{1-3}$alkyl or amino;
$R^{13}$ is H or $C_{1-3}$ alkyl;
$R^{14}$ is H or $C_{1-3}$ alkyl;
$R^{15}$ is H or $C_{1-3}$ alkyl;
L is $CHR^{16}$;
a is 1, 2, 3, 4 or 5;
b is 1, 2, 3, 4 or 5;
c is 1;
d is 1, 2 or 3; and
with the proviso:
when $R^9$ is —$OR^{15}$ then d is not 1.

5. The method according to claim 1, wherein said compound is represented by Formula I wherein:
$R^2$ is optionally substituted 5-member aromatic heterocycle, optionally substituted non-aromatic 5-member heterocycle or optionally substituted cycloalkenyl;
$R^8$ is H;
$R^9$ is —$P(O)(OH)_2$, —$S(O)_2OH$, —P(O)(H)OH or —P(O)MeOH;
$R^{10}$ is H;
$R^{11}$ is H;
$R^{12}$ is H;
L is $CHR^{18}$;
a is 2, 3, 4 or 5;
b is 1, 2, 3, 4 or 5;
c is 1;
d is 1, 2 or 3;
$R^{16}$ is H.

6. The method according to claim 1, wherein said compound is represented by Formula I wherein:
$R^3$ is O.

7. The method according to claim 1, wherein said compound is represented by Formula I wherein:
$R^3$ is N—$R^{11}$; and
$R^{11}$ is H.

8. The method according to claim 1, wherein said compound is represented by Formula I wherein:
$R^3$ is CH—$R^{12}$; and
$R^{12}$ is H.

9. The method according to claim 1, wherein said compound is represented by Formula I wherein:
$R^9$ is $P(O)(OH)_2$.

10. The method according to claim 1, wherein said compound is represented by Formula I wherein:
$R^4$ is optionally substituted aryl.

11. The method according to claim 1, wherein said compound is represented by Formula I wherein:
$R^2$ is optionally substituted 5-member aromatic heterocycle or optionally substituted 5-member non-aromatic heterocycle.

12. The method according to claim 1, wherein said compound is represented by Formula I wherein:
(3-{[4-{[5-(3-methoxyphenyl)pentyl]oxy}-3-(2-thienyl)benzyl]amino}propyl)phosphonic acid;
(3-{[4-{[5-(4-methoxyphenyl)pentyl]oxy}-3-(2-thienyl)benzyl]amino}propyl)phosphonic acid;
(3-{[4-{[5-(4-fluorophenyl)pentyl]oxy}-3-(2-thienyl)benzyl]amino}propyl)phosphonic acid;
(3-{[3-(2-furyl)-4-({5-[3-(trifluoromethyl)phenyl]pentyl}oxy)benzyl]amino}propyl)phosphonic acid;

(3-{[3-(2-furyl)-4-{[5-(3-methoxyphenyl)pentyl]oxy}benzyl]amino}propyl)phosphonic acid
(3-{[4-{[5-(4-fluorophenyl)pentyl]oxy}-3-(2-furyl)benzyl]amino}propyl)phosphonic acid;
[3-({4-[4-(4-fluorophenyl)butoxy]-3-(2-thienyl)benzyl}amino)propyl]phosphonic acid;
[3-({4-[4-(4-fluorophenyl)butoxy]-3-(2-furyl)benzyl}amino)propyl]phosphonic acid;
(3-{[4-{[5-(3-fluoro-4-methoxyphenyl)pentyl]oxy}-3-(2-furyl)benzyl]amino}propyl)phosphonic acid;
(3-{[4-{[5-(3-fluoro-4-methoxyphenyl)pentyl]oxy}-3-(2-thienyl)benzyl]amino}propyl)phosphonic acid;
(3-{[4-{[5-(4-chlorophenyl)pentyl]oxy}-3-(2-furyl)benzyl]amino}propyl)phosphonic acid;
(3-{[4-{[5-(4-chlorophenyl)pentyl]oxy}-3-(2-thienyl)benzyl]amino}propyl)phosphonic acid;
(3-{[4-{[5-(3-chloro-4-methoxyphenyl)pentyl]oxy}-3-(2-furyl)benzyl]amino}propyl)phosphonic acid;
(3-{[4-{[5-(3-chloro-4-methoxyphenyl)pentyl]oxy}-3-(2-thienyl)benzyl]amino}propyl)phosphonic acid;
(3-{[3-(2-furyl)-4-{[5-(4-methoxyphenyl)pentyl]oxy}benzyl]amino}propyl)phosphonic acid;
(3-{[3-(3-furyl)-4-{[5-(3-methoxyphenyl)pentyl]oxy}benzyl]amino}propyl)phosphonic acid;
[3-({3-(1,3-oxazol-4-yl)-4-[(5-phenylpentyl)oxy]benzyl}amino)propyl]phosphonic acid;
[3-({3-(2-furyl)-4-[(5-phenylpentyl)oxy]benzyl}amino)-1-methylpropyl]phosphonic acid;
[3-({4-[(5-phenylpentyl)oxy]-3-(2-thienyl)benzyl}amino)propyl]phosphinic acid;
[3-({3-(5-fluoro-2-furyl)-4-[(5-phenylpentyl)oxy]benzyl}amino)propyl]phosphonic acid;
(3-{[4-{[5-(3-chlorophenyl)pentyl]oxy}-3-(2-furyl)benzyl]amino}propyl)phosphonic acid;
(3-{[3-(2-furyl)-4-{[5-(3-methylphenyl)pentyl]oxy}benzyl]amino}propyl)phosphonic acid;
[1,1-difluoro-3-({3-(5-fluoro-2-furyl)-4-[(5-phenylpentyl)oxy]benzyl}amino)propyl]phosphonic acid;
{3-[(1-{4-[(5-phenylpentyl)oxy]-3-(2-thienyl)phenyl}ethyl)amino]propyl}phosphonic acid;
[3-({4-[(5-phenylpentyl)oxy]-3-(1H-pyrazol-1-yl)benzyl}amino)propyl]phosphonic acid;
[3-({4-[(5-phenylpentyl)oxy]-3-(1H-pyrrol-1-yl)benzyl}amino)propyl]phosphonic acid;
[3-({3-(2-furyl)-4-[(5-phenylpentyl)oxy]benzyl}amino)propyl]phosphonic acid;
[3-({3-(2-furyl)-4-[(5-phenylpentyl)amino]benzyl}amino)propyl]phosphonic acid;
[3-({3-(1,3-oxazol-2-yl)-4-[(5-phenylpentyl)amino]benzyl}amino)propyl]phosphonic acid;
[3-({4-[(5-phenylpentyl)amino]-3-(1,3-thiazol-2-yl)benzyl}amino)propyl]phosphonic acid;
(3-{[4-{[5-(2-fluorophenyl)pentyl]oxy}-3-(2-furyl)benzyl]amino}propyl)phosphonic acid;
(3-{[4-{[5-(2-fluorophenyl)pentyl]oxy}-3-(3-furyl)benzyl]amino}propyl)phosphonic acid;
[3-({2-fluoro-5-(2-furyl)-4-[(5-phenylpentyl)oxy]benzyl}amino)propyl]phosphonic acid;
(3-((4-((3-(3-bromo-4-isopropoxyphenyl)propyl)amino)-3-(furan-3-yl)benzyl)amino) propyl)phosphonic acid;
(3-((4-((3-(3-chloro-4-isobutylphenyl)propyl)amino)-3-(furan-3-yl)benzyl)amino)propyl)phosphonic acid;
(3-((4-((3-(3-chloro-4-isopropoxyphenyl)propyl)amino)-3-(furan-3-yl)benzyl)amino) propyl)phosphonic acid;
(3-((2-fluoro-4-((5-(4-fluorophenyl)pentyl)oxy)-5-(furan-2-yl)benzyl)amino) propyl)phosphonic acid;
(3-((2-fluoro-4-((5-(2-fluorophenyl)pentyl)oxy)-5-(furan-2-yl)benzyl)amino) propyl)phosphonic acid;
(3-((2-fluoro-4-((5-(4-fluorophenyl)pentyl)oxy)-5-(furan-3-yl)benzyl)amino) propyl)phosphonic acid;
(3-((2-fluoro-4-((5-(2-fluorophenyl)pentyl)oxy)-5-(furan-3-yl)benzyl)amino) propyl)phosphonic acid;
(3-((2-fluoro-4-((5-(4-fluorophenyl)pentyl)amino)-5-(furan-2-yl)benzyl)amino) propyl)phosphonic acid;
(3-((2-fluoro-4-((5-(2-fluorophenyl)pentyl)amino)-5-(furan-2-yl)benzyl)amino) propyl)phosphonic acid;
(3-((2-fluoro-4-((5-(4-fluorophenyl)pentyl)amino)-5-(furan-3-yl)benzyl)amino)propyl)phosphonic acid;
(3-((2-fluoro-4-((5-(2-fluorophenyl)pentyl)amino)-5-(furan-3-yl)benzyl)amino) propyl)phosphonic acid;
(3-((3-(furan-2-yl)-4-(3-(4-isobutylphenyl)propoxy)benzyl)amino)propyl)phosphonic acid;
(3-((4-(3-(3-cyano-4-isobutylphenyl)propoxy)-3-(furan-2-yl)benzyl)amino) propyl)phosphonic acid;
(3-((4-(3-(3-cyano-4-isopropoxyphenyl)propoxy)-3-(furan-2-yl)benzyl)amino) propyl)phosphonic acid;
(3-((4-(3-(3-cyano-4-isobutylphenyl)propoxy)-3-(thiophen-2-yl)benzyl)amino) propyl)phosphonic acid;
(3-((4-(3-(3-cyano-4-isopropoxyphenyl)propoxy)-3-(thiophen-2-yl)benzyl)amino) propyl)phosphonic acid;
(3-((3-(furan-3-yl)-4-(3-(4-isobutyl-3-(trifluoromethyl)phenyl)propoxy)benzyl)amino)propyl)phosphonic acid;
(3-((3-(furan-3-yl)-4-(3-(4-isopropoxy-3-(trifluoromethyl)phenyl)propoxy)benzyl)amino)propyl)phosphonic acid;
(3-((4-(3-(3-bromo-4-isobutylphenyl)propoxy)-3-(furan-3-yl)benzyl)amino)propyl)phosphonic acid;
(3-((4-(3-(3-bromo-4-isopropoxyphenyl)propoxy)-3-(furan-3-yl)benzyl)amino)propyl)phosphonic acid;
(3-((4-(3-(3-chloro-4-isobutylphenyl)propoxy)-3-(furan-3-yl)benzyl)amino)propyl)phosphonic acid;
(3-((4-(3-(3-chloro-4-isopropoxyphenyl)propoxy)-3-(furan-3-yl)benzyl)amino)propyl)phosphonic acid;
(3-((4-(3-(3-fluoro-4-isobutylphenyl)propoxy)-3-(furan-3-yl)benzyl)amino)propyl)phosphonic acid;
(3-((4-(3-(3-fluoro-4-isopropoxyphenyl)propoxy)-3-(furan-3-yl)benzyl)amino)propyl)phosphonic acid;
(3-((4-(3-(3-cyano-4-isobutylphenyl)propoxy)-3-(furan-3-yl)benzyl)amino)propyl)phosphonic acid;
(3-((4-(3-(3-cyano-4-isopropoxyphenyl)propoxy)-3-(furan-3-yl)benzyl)amino)propyl)phosphonic acid;
(3-((3-(furan-2-yl)-4-((3-(4-isobutylphenyl)propyl)amino)benzyl)amino)propyl)phosphonic acid;
(3-((3-(furan-2-yl)-4-((3-(4-isopropoxyphenyl)propyl)amino)benzyl)amino)propyl)phosphonic acid;
(3-((4-((3-(3-fluoro-4-isobutylphenyl)propyl)amino)-3-(furan-2-yl)benzyl)amino)propyl)phosphonic acid;
(3-((4-(3-(3-fluoro-4-isopropoxyphenyl)propoxy)-3-(thiophen-2-yl)benzyl)amino)propyl)phosphonic acid;
(3-((4-((3-(3-fluoro-4-isopropoxyphenyl)propyl)amino)-3-(furan-2-yl)benzyl)amino) propyl)phosphonic acid;
(3-((3-(furan-2-yl)-4-(3-(4-isobutyl-3-(trifluoromethyl)phenyl)propoxy)benzyl)amino)propyl)phosphonic acid;
(3-((4-(3-(4-isobutyl-3-(trifluoromethyl)phenyl)propoxy)-3-(thiophen-2-yl)benzyl)amino) propyl)phosphonic acid;
(3-((4-(3-(4-isopropoxy-3-(trifluoromethyl)phenyl)propoxy)-3-(thiophen-2-yl)benzyl)amino)propyl)phosphonic acid;
(3-((4-(3-(3-bromo-4-isobutylphenyl)propoxy)-3-(furan-2-yl)benzyl)amino)propyl)phosphonic acid;

(3-((4-(3-(3-bromo-4-isopropoxyphenyl)propoxy)-3-(furan-2-yl)benzyl)amino)propyl)phosphonic acid;
(3-((4-(3-(3-bromo-4-isobutylphenyl)propoxy)-3-(thiophen-2-yl)benzyl)amino)propyl)phosphonic acid;
(3-((4-(3-(3-bromo-4-isopropoxyphenyl)propoxy)-3-(thiophen-2-yl)benzyl)amino)propyl)phosphonic acid;
(3-((4-(3-(3-chloro-4-isobutylphenyl)propoxy)-3-(furan-2-yl)benzyl)amino)propyl)phosphonic acid;
(3-((4-(3-(3-chloro-4-isopropoxyphenyl)propoxy)-3-(furan-2-yl)benzyl)amino)propyl)phosphonic acid;
(3-((4-(3-(3-chloro-4-isobutylphenyl)propoxy)-3-(thiophen-2-yl)benzyl)amino)propyl)phosphonic acid;
(3-((4-(3-(3-chloro-4-isopropoxyphenyl)propoxy)-3-(thiophen-2-yl)benzyl)amino)propyl)phosphonic acid;
(3-((4-(3-(3-fluoro-4-isobutylphenyl)propoxy)-3-(furan-2-yl)benzyl)amino)propyl)phosphonic acid;
(3-((4-(3-(3-fluoro-4-isopropoxyphenyl)propoxy)-3-(furan-2-yl)benzyl)amino)propyl)phosphonic acid;
(3-((4-(3-(3-fluoro-4-isobutylphenyl)propoxy)-3-(thiophen-2-yl)benzyl)amino)propyl)phosphonic acid;
(3-((3-(furan-3-yl)-4-((3-(4-isopropoxy-3-(trifluoromethyl)phenyl)propyl)amino)benzyl)amino)propyl) phosphonic acid;
(3-((4-((3-(3-bromo-4-isobutylphenyl)propyl)amino)-3-(furan-3-yl)benzyl)amino)propyl)phosphonic acid;
(3-((3-(furan-3-yl)-4-((3-(4-isopropoxyphenyl)propyl)amino)benzyl)amino) propyl)phosphonic acid;
(3-((4-((3-(3-fluoro-4-isobutylphenyl)propyl)amino)-3-(furan-3-yl)benzyl)amino)propyl)phosphonic acid;
(3-((4-((3-(3-fluoro-4-isopropoxyphenyl)propyl)amino)-3-(furan-3-yl)benzyl)amino)propyl)phosphonic acid;
(3-((4-((3-(3-cyano-4-isobutylphenyl)propyl)amino)-3-(furan-3-yl)benzyl)amino)propyl)phosphonic acid;
(3-((4-((3-(3-cyano-4-isopropoxyphenyl)propyl)amino)-3-(furan-3-yl)benzyl)amino) propyl)phosphonic acid;
(3-((3-(furan-3-yl)-4-((3-(4-isobutyl-3-(trifluoromethyl)phenyl)propyl)amino)benzyl)amino)propyl)phosphonic acid;
(3-((4-((3-(3-cyano-4-isobutylphenyl)propyl)amino)-3-(furan-2-yl)benzyl)amino)propyl)phosphonic acid;
(3-((4-((3-(3-cyano-4-isopropoxyphenyl)propyl)amino)-3-(furan-2-yl)benzyl)amino) propyl)phosphonic acid;
(3-((3-(furan-2-yl)-4-((3-(4-isobutyl-3-(trifluoromethyl)phenyl)propyl)amino)benzyl)amino)propyl)phosphonic acid;
(3-((3-(furan-2-yl)-4-((3-(4-isopropoxy-3-(trifluoromethyl)phenyl)propyl)amino)benzyl)amino)propyl) phosphonic acid;
(3-((4-((3-(3-bromo-4-isobutylphenyl)propyl)amino)-3-(furan-2-yl)benzyl)amino) propyl)phosphonic acid;
(3-((4-((3-(3-bromo-4-isopropoxyphenyl)propyl)amino)-3-(furan-2-yl)benzyl)amino) propyl)phosphonic acid;
(3-((4-((3-(3-chloro-4-isobutylphenyl)propyl)amino)-3-(furan-2-yl)benzyl)amino) propyl)phosphonic acid;
(3-((4-((3-(3-chloro-4-isopropoxyphenyl)propyl)amino)-3-(furan-2-yl)benzyl)amino) propyl)phosphonic acid;
(3-((3-(furan-3-yl)-4-((3-(4-isobutylphenyl)propyl)amino)benzyl)amino)propyl)phosphonic acid;
(3-((2-fluoro-4-(6-(2-fluorophenyl)hexyl)-5-(furan-3-yl)benzyl)amino)propyl)phosphonic acid;
(3-((2-fluoro-4-(6-(2-fluorophenyl)hexyl)-5-(furan-2-yl)benzyl)amino)propyl)phosphonic acid;
(3-((2-fluoro-4-(6-(4-fluorophenyl)hexyl)-5-(furan-3-yl)benzyl)amino)propyl)phosphonic acid;
(3-((2-fluoro-4-(6-(4-fluorophenyl)hexyl)-5-(furan-2-yl)benzyl)amino)propyl)phosphonic acid; and
(3-((3-(furan-2-yl)-4-(6-phenylhexyl)benzyl)amino)propyl)phosphonic acid.

\* \* \* \* \*